United States Patent [19]
Bonnert et al.

[11] Patent Number: 5,763,465
[45] Date of Patent: Jun. 9, 1998

[54] 7-(2-AMINOETHYL) BENZOTHIAZOLONES

[75] Inventors: Roger V. Bonnert; Roger C. Brown, both of Leicestershire; David R. Cheshire, Nottingham; Francis Ince; John Dixon, both of Leicestershire, all of England

[73] Assignee: Astra Pharmaceuticals Limited, Hertfordshire, England

[21] Appl. No.: 740,622

[22] Filed: Oct. 31, 1996

Related U.S. Application Data

[60] Division of Ser. No. 348,154, Nov. 28, 1994, Pat. No. 5,596,010, which is a continuation-in-part of Ser. No. 63,781, May 19, 1993, abandoned, which is a continuation-in-part of PCT/GB93/01095, filed May 27, 1993, which is a continuation-in-part of PCT/GB91/02042, filed Nov. 19, 1991.

[30] Foreign Application Priority Data

| Nov. 20, 1990 | [GB] | United Kingdom | 9025176 |
| Nov. 20, 1990 | [GB] | United Kingdom | 9025178 |
| Nov. 20, 1990 | [GB] | United Kingdom | 9025180 |
| May 27, 1992 | [GB] | United Kingdom | 9211172 |
| May 19, 1992 | [GB] | United Kingdom | 9210632 |

[51] Int. Cl.$^6$ ............... A61K 31/425; A61K 31/16; C07D 277/62; C07C 233/02

[52] U.S. Cl. ............. 514/367; 514/393; 514/418; 514/387; 514/629; 548/165; 548/169; 548/171; 548/306.4; 548/480; 564/155; 564/158; 564/215; 564/218

[58] Field of Search ........................ 564/155, 158, 564/215, 218; 514/387, 367, 418, 629, 393; 548/165, 169, 171, 306.4, 480

[56] References Cited

U.S. PATENT DOCUMENTS 3,996,383  12/1976  Colella et al. ............... 424/330

OTHER PUBLICATIONS

Weinstock et al, "Synthesis and evaluation of non-catechol D-1 and D-2 dopamine receptor agonists: benzimidazol-2-one, benzoxazol-2-one, and the highly potent: benzothiazol-2-one 7-ethylamines"CA 107:77705, 1987.

DeMarinis et al, "Syntheses and in vitro evaluation of 4-2-aminoethyl-23H0-indolones and related compounds as peripheral prejunctional dopamine receptor agonists", CA 105:6379, 1986.

Dixon et al, "Phenylethylamines and compositions containing them", CA 104:5631, 1986.

Colella et al (I) "N,N'-bis[2-(4-hydroxyphenyl)ethyl]polymethylenediamines", CA 79:126069, 1973.

Jack et al, "Hypotensive phenylethylamine, derivatives", CA 75:35408, 1971.

CA 96:6373C, 1983.

*Primary Examiner*—Deborah Lambkin
*Attorney, Agent, or Firm*—Nixon & Vanderhye

[57] ABSTRACT

There are disclosed compounds of formula I.

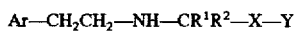

Ar—CH$_2$CH$_2$—NH—CR$^1$R$^2$—X—Y    I in which
Ar represents a group,

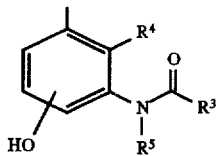

X represents a C$_{1-12}$ alkylene chain optionally interrupted or terminated by one or more groups selected from —S(O)$_n$—, —O—, —C(Z)—, CR$^6$R$^7$, phenylmethyne, —NR$^8$—, —CONH—, —NHCO— and —NHCONH—.

Y represents an optionally substituted aryl or cycloalkyl group,

Z represents O or S,

R$^1$, R$^2$, R$^5$ and R$^9$ each independently represent hydrogen or alkyl C$_{1-6}$.

R$^3$ and R$^4$ represent hydrogen, or R$^3$ and R$^4$ together form a group —S—, —NR$^9$— or —CH$_2$—.

R$^6$ and R$^7$ independently represent hydrogen, alkyl C$_{1-6}$; fluoro, cyano, or CF$_3$, provided that at least one of R$^6$ and R$^7$ is other than hydrogen, R$^8$ represents hydrogen or alkyl C$_{1-6}$, or when X is interrupted or terminated by more than one —NR$^8$— group may together with another R$^8$ group form the chain —CH$_2$—CH$_2$—, and n represents 0, 1 or 2, and pharmaceutically acceptable derivatives thereof.

Processes for their production and pharmaceutical compositions and methods of treatment involving their use are also described.

17 Claims, No Drawings

7-(2-AMINOETHYL) BENZOTHIAZOLONES

This is a Rule 60 Divisional of application Ser. No. 08/348,154, filed Nov. 28, 1994, U.S. Pat. No. 5,596,610, which is CIP of application Ser. No. 08/063,781, filed 19 May 1993, now abandoned, which is a CIP of PCT/GB93/01095, filed 27 May 1993, which is a CIP of PCT/GB91/02042, filed Nov. 19, 1991.

This invention relates to novel compounds, processes for their preparation, pharmaceutical compositions containing them and methods of treatment involving their use.

According to the invention there are provided compounds of formula I,

in which

Ar represents a group,

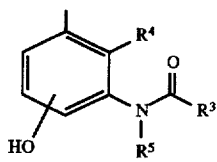

X represents a $C_{1-12}$ alkylene chain optionally interrupted or terminated by one or more groups selected from —S(O)$_n$—, —O—, —C(Z)—, $CR^6R^7$, phenylmethyne, —$NR^8$—, —CONH—, —NHCO— and —NHCONH—, Y represents an optionally substituted aryl or cycloalkyl group, Z represents O or S, $R^1$, $R^2$, $R^5$ and $R^9$ each independently represent hydrogen or alkyl $C_{1-6}$, and $R^3$ and $R^4$ represent hydrogen, or $R^3$ and $R^4$ together form a group —S—, —$NR^9$— or —$CH_2$—, $R^6$ and $R^7$ independently represent hydrogen, alkyl $C_{1-6}$, fluoro, cyano, or $CF_3$, provided that at least one of $R^6$ and $R^7$ is other than hydrogen, $R^8$ represents hydrogen or alkyl $C_{1-6}$, or when X is interrupted or terminated by more than one —$NR^8$— group may together with another $R^8$ group form the chain —$CH_2$—$CH_2$—, and n represents 0, 1 or 2, and pharmaceutically acceptable derivatives thereof.

According to the invention we also provide a process for the production of a compound of formula I, or a pharmaceutically acceptable derivative thereof, which comprises a) alkylation of a compound of formula II, or a derivative thereof,

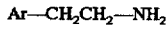

in which Ar is as defined above, with an alkylating agent of formula III,

L—$CR^1R^2$—X—Y    III in which $R^1$, $R^2$, X and Y are as defined above and L represents a leaving group, b) alkylation of a compound of formula II, as defined above, with a compound of formula IV,

O=$CR^1$—X—Y    IV in which $R^1$, X and Y are as defined above,
in the presence of a reducing agent, c) selective reduction of a compound of formula V,

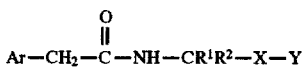

in which Ar, X, Y, $R^1$ and $R^2$ are as defined above, or for the production of compounds of formula I in which $R^1$ and $R^2$ represent hydrogen selective reduction of a compound of formula Va,

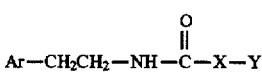

in which Ar, X and Y are as defined above, d) removal of a protecting group from a corresponding protected compound of formula I in which one or more of the functional groups is protected, and where desired or necessary converting the resulting compound of formula I to a pharmaceutically acceptable derivative thereof, or vice versa.

In process a) leaving groups which L may represent include halide, such as chloride, bromide and iodide, and alkyl or arylsulphonyloxy groups such as methanesulphonyloxy or p-toluenesulphonyloxy. The reaction is preferably carried out in the presence of a base, e.g. an inorganic base such as sodium or potassium carbonate, or an organic base such as triethylamine, N,N-diisopropylethylamine or pyridine. The reaction is conveniently performed in a solvent such as an ether, e.g. tetrahydrofuran or dioxan, a ketone, e.g. butanone or methyl isobutyl ketone, a substituted amide, e.g. dimethylformamide, or a chlorinated hydrocarbon, e.g. chloroform, at a temperature of between ambient temperature and the reflux temperature of the solvent.

The alkylating agent of formula III may be prepared from the corresponding alcohol (i.e. the compound in which L represents OH) by known methods. For example, the alcohol may be reacted with a halogenating agent to yield the compound of formula III in which L represents a halogen atom. Suitable halogenating agents include, for example, triphenylphosphine-tetrahalogenomethane adduct (conveniently formed in situ, e.g. by the reaction of triphenylphosphine and carbontetrabromide). The reaction may take place in the presence of a solvent such as acetonitrile, or a chlorinated hydrocarbon, e.g. dichloromethane, at a temperature in the range of 0°–30° C.

In process b) suitable reducing agents include hydrogen in the presence of a catalyst such as platinum, platinum oxide, palladium, palladium oxide, Raney nickel or rhodium, on a support such as charcoal, using an alcohol, e.g. ethanol, or an ester, e.g. ethyl acetate, or an ether, e.g. tetrahydrofuran, or water, as reaction solvent, or a mixture of solvents, at normal or elevated temperature and pressure. Alternatively the reducing agent may be a hydride such as diborane or a metal hydride such as sodium borohydride, sodium cyanoborohydride or lithium aluminium hydride. Suitable solvents for the reaction with these reducing agents will depend on the particular hydride used, but will include alcohols, such as methanol or ethanol, or ethers, such as diethyl ether or t-butyl methyl ether, or tetrahydrofuran.

Alkylation using the compound of formula IV may give rise to an intermediate imine, reduction of which under the conditions described yields the compound of formula I.

The compounds of formulae II and IV and the alcohols corresponding to formula III are either known or may be prepared by known techniques.

In process c) the reaction may be carried out using conventional reduction techniques. The reducing agent may be electrophilic, e.g. diborane, or nucleophilic, e.g. a complex metal hydride such as lithium aluminium hydride or sodium bis(2-methoxyethoxy)aluminium hydride. The solvent is preferably inert to the reaction conditions. Aprotic solvents are preferred, e.g. tetrahydrofuran, diethyl ether, or 1,2-dimethoxyethane. The reaction may be carried out at a temperature of from about 0° to 100° C.

The compounds of formulae V and Va may be prepared by coupling of an amine and an acid or acid chloride by conventional means. For example, the coupling may be performed in the presence of dicyclohexylcarbodiimide using the method of Sheehan and Hess, *J. Am. Chem. Soc.*, 1955, 77, 1067; or 1,1-dicarbonyldiimidazole as described by Staab, *Angew. Chem. Int. Ed. Engl.*, 1962, 1, 351. The amines required for the coupling reaction are either known or may be prepared by conventional methods, for example, compounds in which $R^3$ and $R^4$ together represent —S— may be prepared as described in *J. Med. Chem.*, 1987, 30, 1166.

The intermediates of formula Va are novel, thus according to a further aspect of the invention there are provided compounds of formula Va,

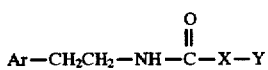

$$Ar-CH_2CH_2-NH-\overset{\overset{\displaystyle O}{\|}}{C}-X-Y \qquad Va$$

in which Ar, X and Y are as defined above.

Further preparative details for the compounds of formula I are given in the Examples.

In the above processes it may be necessary for any functional groups, e.g. hydroxy or amino groups, present in the starting materials to be protected, thus process d) may involve the removal of one or more protecting groups. Suitable protecting groups and methods for their removal are, for example, those described in "Protective Groups in Organic Synthesis" by T. W. Greene and P. G. M. Wuts, John Wiley and Sons Inc., 1991. Hydroxy groups may, for example, be protected by arylmethyl groups such as phenylmethyl, diphenylmethyl or triphenylmethyl, or as tetrahydropyranyl derivatives.

Suitable amino protecting groups include arylmethyl groups such as benzyl, (R,S)-α-phenylethyl, diphenylmethyl or triphenylmethyl, and acyl groups such as acetyl, trichloroacetyl or trifluoroacetyl. Conventional methods of deprotection may be used. Arylmethyl groups may, for example, be removed by hydrogenolysis in the presence of a metal catalyst e.g. palladium on charcoal. Tetrahydropyranyl groups may be cleaved by hydrolysis under acidic conditions. Acyl groups may be removed by hydrolysis with a base such as sodium hydroxide or potassium carbonate, or a group such as trichloroacetyl may be removed by reduction with, for example, zinc and acetic acid.

Pharmaceutically acceptable derivatives of the compound of formula I include pharmaceutically acceptable salts, esters and amides thereof.

Suitable pharmaceutically acceptable salts of the compounds of formula I include acid addition salts derived from inorganic and organic acids, such as hydrochlorides, hydrobromides, sulphates, phosphates, maleates, tartrates, citrates, benzoates, 4-methoxybenzoates, 2- or 4-hydroxybenzoates, 4-chlorobenzoates, benzenesulphonates, p-toluenesulphonates, naphthalenesulphonates, methanesulphonates, sulphamates, ascorbates, salicylates, acetates, diphenylacetates, triphenylacetates, adipates, fumarates, succinates, lactates, glutarates, gluconates, hydroxy-naphthalenecarboxylates, e.g. 1-hydroxy or 3-hydroxy-2-naphthalenecarboxylates, or oleates. The compounds may also form salts with suitable bases. Examples of such salts include alkali metal, e.g. sodium and potassium, and alkaline earth metal, e.g. calcium and magnesium, salts. The compound of formula I may be obtained in the form of a salt, conveniently a pharmaceutically acceptable salt. Where desired, such salts may be converted to the free bases using conventional methods. Pharmaceutically acceptable salts may be prepared by reacting the compound of formula I with an appropriate acid or base in the presence of a suitable solvent.

Suitable pharmaceutically acceptable esters of the compounds of formula I include alkyl $C_{1-6}$ esters, e.g. ethyl ester. The esters may be made by conventional techniques, e.g. esterification or transesterification.

Suitable amides include unsubstituted or mono- or di-substituted alkyl $C_{1-6}$ or phenyl amides, and may be made by conventional techniques, e.g. reaction of an ester of the corresponding acid with ammonia or an appropriate amine.

The compounds of formula I may exhibit tautomerism, they may also contain one or more asymmetric carbon atoms and may therefore exhibit optical and/or diastereoisomerism. Diastereoisomers may be separated using conventional techniques, e.g. chromatography or fractional crystallisation. The various optical isomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation.

By the term alkyl we mean straight, branched or cyclic saturated or unsaturated alkyl groups.

The term cycloalkyl includes $C_{3-12}$ cyclic groups. The cycloalkyl group may contain from 1 to 3 heteroatoms selected from N, O and S. The cycloalkyl group may be unsubstituted or substituted, for example, by one or more groups selected from —OH, halogen, alkyl $C_{1-6}$, alkoxy $C_{1-6}$, =O, —NH$_2$ or NO$_2$. Provided that such substituents do not interfere with the efficacy-of the compound. Particular cycloalkyl groups which may be mentioned include $C_5$ and $C_6$ cycloalkyl groups, e.g. cyclohexane.

The term aryl includes aromatic radicals having five or six atoms in a single ring is system, such groups may contain from 1 to 3 heteroatoms selected from N, O and S. The single ring system may be substituted to form a multiple fused ring system containing up to 10 atoms, for example, naphthyl, indenyl or benzothiazolyl. The aryl group may be unsubstituted or substituted, for example, by one or more groups selected from —OH, halogen, alkyl $C_{1-6}$, =O, —NH$_2$ or NO$_2$. Provided that such substituents do not interfere with the efficacy of the compound. Particular aryl groups which may be mentioned include 5- and 6-membered carbocyclic and heterocyclic aryl groups, for example, furanyl, pyridinyl and thienyl. However, we prefer compounds of formula I in which Y represents phenyl.

Halogens with which Y may be substituted include bromine, chlorine and fluorine.

We prefer compounds of formula I in which X represents a $C_{3-8}$, more preferably a $C_{4-7}$, and especially a $C_{5-6}$ alkylene chain.

Where the group X contains more than one group selected from —S(O)$_n$—, —O—, —C(Z)—, $CR^6R^7$, phenylmethyne, —NR$^8$—, —CONH—, —NHCO— and —NHCONH—, then those groups may be the same or different.

We prefer compounds in which X is interrupted or terminated by at least one group, and more preferably one to three groups, e.g. one or two groups, selected from —S(O)$_n$—, —O—, —C(Z)—, CR$^6$R$^7$, phenylmethyne, —NR$^8$—, —CONH—, —NHCO— and —NHCONH—.

When X is interrupted or terminated by —NR$^8$—, alkyl groups that R$^8$ may represent include alkyl C$_{1-3}$, e.g methyl.

Specific groups which X may represent include the following:
—(CH$_2$)$_2$—SO$_2$—(CH$_2$)$_2$—O—(CH$_2$)$_2$—
—CH$_2$—SO$_2$—(CH$_2$)$_3$—O—(CH$_2$)$_2$—
—(CH$_2$)$_5$—O—
—(CH$_2$)$_5$—O—CH$_2$—
—(CH$_2$)$_5$—O—(CH$_2$)$_2$—
—(CH$_2$)$_5$—O—(CH$_2$)$_3$—
—(CH$_2$)$_5$—O—(CH$_2$)$_4$—
—(CH$_2$)$_3$—O—(CH$_2$)$_2$—
—(CH$_2$)$_2$—SO$_2$—(CH$_2$)$_2$—NH—(CH$_2$)$_2$—
—(CH$_2$)$_4$—CONH—(CH$_2$)$_2$—
—CH$_2$—SO$_2$—(CH$_2$)$_2$—CONH—(CH$_2$)$_2$—
—(CH$_2$)$_5$—NH—CONH—(CH$_2$)$_2$—
—CHMe—(CH$_2$)$_4$—O—(CH$_2$)$_2$—
—CMe$_2$—(CH$_2$)$_4$—O—(CH$_2$)$_2$—
—(CH$_2$)$_5$—NH—CH$_2$—CF$_2$—
—CF$_2$—(CH$_2$)$_4$—O—(CH$_2$)$_2$—
—CH$_2$—CF$_2$—(CH$_2$)$_3$—O—(CH$_2$)$_2$—
—(CH$_2$)$_2$—C(CN)$_2$—(CH$_2$)$_2$—O—(CH$_2$)$_2$—
—CH$_2$—NMe—C(O)—(CH$_2$)$_2$—O—(CH$_2$)$_2$—

We prefer compounds of formula I in which R$^3$ and R$^4$ together represent the group —S—.

We prefer Ar groups in which the —OH is positioned ortho to the —NR$^5$—C(O)R$^3$ group.

When R$^1$ and R$^2$ are other than hydrogen, alkyl groups which they may represent include alkyl C$_{1-3}$, for example, methyl.

We prefer compounds of formula I in which R$^5$ represents hydrogen.

A particularly preferred group of compounds of formula I is that in which Ar represents the group:

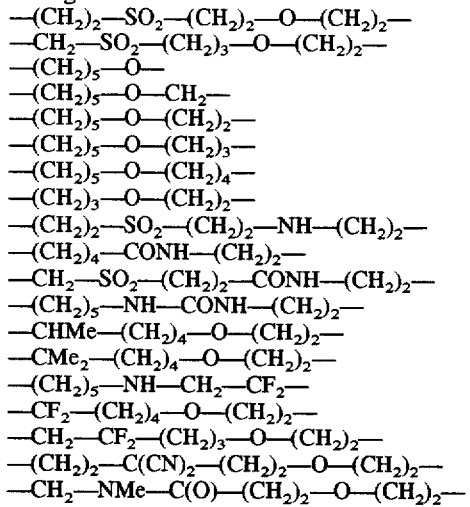

and —CR$^1$R$^2$—X—Y represents —(CH$_2$)$_p$—W—(CH$_2$)$_q$—Q—(CH$_2$)$_r$—R, wherein W and Q independently represent —S(O)$_n$— or —O—, n represents 0, 1 or 2, p, q and r independently represent 2 or 3, R represents phenyl optionally substituted by halogen, —OR$^1$, NO$_2$ or NR$^2$R$^3$; or a 5- or 6-membered N, O, or S containing heterocycle, and R$^1$, R$^2$ and R$^3$ independently represent hydrogen or alkyl C$_{1-6}$.

When R represents phenyl substituted by halogen, —OR$^1$, —NO$_2$ or —NR$^2$R$^3$ we prefer it to be substituted by only one such group. The phenyl may be substituted ortho, meta or para to the —(CH$_2$)$_p$—W—(CH$_2$)$_q$—Q—(CH$_2$)$_r$— group, however, we prefer compounds in which the phenyl is substituted ortho or para to the —(CH$_2$)$_p$—W—(CH$_2$)$_q$—Q—(CH$_2$)$_r$— group.

Particular 5- or 6-membered heterocyclic groups which R may represent include is furanyl, pyridinyl and thienyl. However, we prefer compounds in which R represents phenyl.

Halogens with which R may be substituted include bromine, chlorine and fluorine.

We prefer compounds of formula I in which at least one of W and Q represents —O—.

We prefer compounds of formula I in which r represents 2.

We prefer compounds of formula I in which p+q represents 5.

Specific groups which —(CH$_2$)$_p$—W—(CH$_2$)$_q$—Q—(CH$_2$)$_r$— may represent include the following:
—(CH$_2$)$_3$—S—(CH$_2$)$_2$—O—(CH$_2$)$_2$—
—(CH$_2$)$_3$—SO$_2$—(CH$_2$)$_2$—O—(CH$_2$)$_2$—
—(CH$_2$)$_3$—O—(CH$_2$)$_2$—O—(CH$_2$)$_2$—
—(CH$_2$)$_2$—O—(CH$_2$)$_3$—O—(CH$_2$)$_2$—
—(CH$_2$)$_2$—O—(CH$_2$)$_2$—O—(CH$_2$)$_2$—
—(CH$_2$)$_2$—SO$_2$—(CH$_2$)$_3$—O—(CH$_2$)$_2$—
—(CH$_2$)$_2$—S—(CH$_2$)$_3$—O—(CH$_2$)$_2$—

The compounds of formula I are useful in that they exhibit pharmacological activity in animals. In particular the compounds are $\beta_2$-adrenoreceptor agonists. The activity may be demonstrated in the isolated trachea of the guinea pig, as described by I. G. Dougall, D. Harper, D. M. Jackson, and P. Leff, Br. J. Pharmacol., 1991, 104, 1057. The compounds are also dopamine DA$_2$-agonists. The binding affinities of the test compounds for the DA$_2$ binding sites in bovine pituitary membranes may be determined from the displacement of [$^3$H]-N-n-propylnorapomorphine and of [$^3$H]-spiperone in the absence or presence of nonhydrolysable GTP analogue respectively, D. R. Sibley, A. DeLean and I. Creese, Anterior Pituitary Dopamine Receptors, Demonstration of Interconvertible High and Low Affinity States of the D-2 Dopamine Receptor, J. Biol. Chem., 1982, 257(11), 6351–6361. The DA$_2$ activity may also be demonstrated in a is functional screen, the rabbit isolated ear artery, as described by Brown and O'Connor, Br. J. Pharmacol., 1981, 73, 189P. The compounds also show advantageous DA$_2$:$\beta_2$ activity ratios.

The compounds of formula I are indicated for use in the treatment of the range of conditions known as reversible obstructive airways disease. The term "reversible obstructive airways disease" will be well understood by those skilled in the art to include conditions such as asthma, including bronchial asthma, allergic asthma, intrinsic asthma, extrinsic asthma and dust asthma, particularly chronic or inverterate asthma (for example late asthma and airway hyper-responsiveness); bronchitis and the like (see, for example, UK Patent No. 2022078 and Br. J. Pharmacol., 1987, 24, 4983). Of particular interest is asthma.

The term "treatment" as used herein includes prophylaxis as well as relieving the symptoms of disease.

According to another aspect of the invention there is therefore provided a method of treatment or prophylaxis of reversible obstructive airways disease, which method comprises administering a therapeutically effective quantity of a compound of formula I, or a pharmaceutically acceptable derivative thereof, to a patient suffering from or susceptible to such a condition.

The compounds of formula I are also indicated for use in the treatment of various other conditions, e.g. inflammatory and allergic skin disorders, congestive heart failure and glaucoma.

For the above mentioned uses the doses administered will, of course, vary with compound employed, the mode of administration and the treatment desired. However, in general, satisfactory results are obtained when the compound of formula I is administered at a daily dosage of from about 1 μg to about 20 mg per kg of animal body weight, preferably given in divided doses 1 to 4 times a day or in sustained release form. For man the total daily dose is in the range of from 70 µg to 1,400 mg and unit dosage forms suitable for administration comprise from 20 µg to 1,400 mg of the compound admixed with a solid or liquid pharmaceutical diluent or carrier.

The compounds of formula I may be used on their own or in the form of appropriate pharmaceutical compositions for topical, enteral or parenteral administration.

Compositions in a form suitable for topical administration to the lung include is aerosols, e.g. pressurised or non-pressurised powder compositions;

compositions in a form suitable for oesophageal administration include tablets, capsules and dragees;

compositions in a form suitable for administration to the skin include creams, e.g. oil-in-water emulsions or water-in-oil emulsions;

compositions in a form suitable for administration intravenously include injections and infusions; and compositions in a form suitable for administration to the eye include drops and ointments.

According to the invention there is also provided a pharmaceutical composition comprising, preferably less than 80% and more preferably less than 50% by weight of, a compound of formula I, or a pharmaceutically acceptable derivative thereof, in admixture with a pharmaceutically acceptable diluent or carrier.

Examples of such diluents and carriers are:

for tablets and dragees—lactose, starch, talc, stearic acid;

for capsules—tartaric acid or lactose; and for injectable solutions—water, alcohols, glycerin, vegetable oils.

When the compound of formula I is to be administered to the lung it may be inhaled as a powder which may be pressurised or non-pressurised. Pressurised powder compositions of the compounds of formula I may contain a liquified gas propellant or a compressed gas. In non-pressurised powder compositions the active ingredient in finely divided form may be used in admixture with a larger-sized pharmaceutically acceptable carrier comprising particles of up to, for example, 100 µm in diameter. Suitable inert carriers include, e.g. crystalline lactose.

The compounds of formula I have the advantage that they are less toxic, more efficacious, are longer acting, have a broader range of activity, are more potent, produce fewer side effects, are more easily absorbed or have other useful pharmacological properties, than compounds of a similar structure.

The invention is illustrated, but in no way limited, by the following Examples, in which temperatures are in degrees Celsius. The reactions were performed under an inert atmosphere of either nitrogen or argon. Preparative HPLC separations were generally performed using a DYNAMAX™ 60A C-18 reverse phase column.

EXAMPLE 1

7-[2-[6-[2-(2,3-Dihydro-1H-indenyloxy)]hexyl] aminoethyl]-4-hydroxy-1,3-benzthiazol-2(3H)-one hydrochloride a) N-[2-(4-Hydroxy-2-oxo-3H-1,3-benzothiazol-7-yl)ethyl]-6-[2-(2,3-dihydro-1H-indenyloxy)] hexanamide To a stirred solution of 7-(2-aminoethyl)-4-hydroxy-1,3-benzothiazol-2(3H)-one hydrobromide (1.50 g) and 6-[2-(2,3-dihydro-1H-indenyloxy)]hexanoic acid (1.41 g) in dimethylformamide (25 ml) was added triethylamine (0.72 ml), 1-hydroxybenzotriazole hydrate (1.905 g) and dicyclohexylcarbodiimide (1.38 g). The mixture was stirred for 40 hours at room temperature. Glacial acetic acid (0.4 ml) was added and stirring continued for 15 min. The dimethylformamide was removed under reduced pressure, the residue slurried with ethyl acetate (50 ml) and the suspended dicyclohexylurea removed by filtration. The filtrate was washed with saturated aqueous sodium bicarbonate and dried ($MgSO_4$). The solvent was removed under reduced pressure to yield a residue which was purified by column chromatography on silica using 5% ethanol in dichloromethane as eluant, to give the subtitled compound as a yellow oil.

$^1$H NMR ($D_6$-DMSO) δ:1.22 (m, 2H), 1.45 (brm, 4H), 2.00 (t, 2H), 2.58 (t, 2H), 2.80 (d, 1H), 2.85 (d, 1H), 3.06 (d, 1H), 3.10 (d, 1H), 3.22 (q, 2H), 3.4 (m, 2H+$H_2O$), 4.26 (m, 1H), 6.70 (d, 1H), 6.80 (d, 1H), 7.1–7.2 (m, 4H), 7.83 (t, 1H), 9.88 (brs, 1H), 11.61 (s, 1H).

b) 7-[2-[6-[2-(2,3-Dihydro-1H-indenyloxy)hexyl] aminoethyl]-4-hydroxy-1,3-benzthiazol-2(3H)-one hydrochloride Borane-tetrahydrofuran solution (1.0M in THF, 11 ml) was added dropwise to a stirred solution of the product from step a) (1.39 g) in dry tetrahydrofuran. The mixture was heated under reflux until thin layer chromatography indicated the reaction had gone to completion, about 3 hours. The reaction was cooled and methanol (2.5 ml) added, the mixture was then heated under reflux for a further 15 min. The solvent was removed under reduced pressure and the residue dissolved in methanol (25 ml) to which was added concentrated hydrochloric acid (sg. 1.18, 0.55 ml). The solution was heated under reflux for 30 min. Cooling and removal of the methanol under reduced pressure yielded an oily residue which when triturated with ether gave the title compound as an off white solid, which was further purified by reverse phase HPLC using methanol/0.1% aqueous trifluoroacetate as eluant.

mp 220°–223°;

Mass Spectrum: FAB 427 [(M+H)$^+$];

$^1$H NMR ($D_6$-DMSO) δ:1.23 (brs, 4H), 1.48 (brt, 2H), 1.59 (brm, 2H), 2.85 (brm, 6H), 3.10 (brm, 4H), 3.42 (t, 2H), 4.26 (m, 1H), 6.76 (d, 1H), 6.86 (d, 1H), 7.12 (m, 2H), 7.20 (m, 2H), 8.80 (brs, 2H), 10.13 (s, 1H), 11.77 (s, 1H);

Analysis: Found; C,61.94; H,6.91; N,6.15; S,6.52%.

$C_{24}H_3N_2O_3S$.HCl requires: C,62.25; H,6.75; N,6.05; S,6.92%.

EXAMPLE 2

The following compounds were prepared according to the method of Example 1, from the corresponding intermediate amides:

a) 4Hydroxy-7-[2-[6-(2-phenylethoxy)hexyl] aminoethyl]-1,3-benzothiazol-2(3H)-one hydrochloride i. N-[2-(4-Hydroxy-2-oxo-3H-1,3-benzothiazol-7-yl) ethyl]-6-(2-phenylethoxy)-hexanamide mp 139°;

Mass Spectrum: FAB 429 [(M+H)$^+$];

$^1$H NMR ($D_6$-DMSO) δ:1.20 (m, 2H), 1.45 (m, 4H), 2.00 (t, 2H), 2.77 (t, 2H), 3.23 (q, 2H), 3.34 (m, 4H+$H_2O$), 3.55 (t, 2H), 6.69 (d, 1H), 6.78 (d, 1H), 7.16–7.28 (m, 5H), 7.84 (t, 1H);

Analysis: Found; C,64.03; H,6.41; N,6.60; S,6.84%.

$C_{23}H_{28}N_2O_4S$ requires: C,64.46; H,6.58; N,6.54; S,7.48%.

ii. 4-Hydroxy-7-[2-[6-(2-phenylethoxy)hexyl] aminoethyl]-1,3-benzothiazol-2(3H)-one hydrochloride mp 219°–222° C. (decomposes);

Mass spectrum: FAB 415 [(M+H)$^+$];

$^1$H NMR (D$_6$-DMSO) δ:1.22–1.37 (m, 4H), 1.47 (t, 2H), 1.54–1.64 (m, 2H), 2.8–2.9 (m, 6H), 3.01–3.12 (brm, 2H), 3.34–3.47 (m, 2H), 3.55 (t, 2H), 6.76 (d, 1H), 6.88 (d, 1H), 7.06–7.32 (m, 5H), 8.87 (brs, 2H), 10.15 (s, 1H), 11.78 (s, 1H);

Analysis: Found; C,60.82; H,6.53; N,6.01; S,6.63; Cl,8.34%.

$C_{23}H_{30}N_2O_3S.HCl$ requires: C,61.25; H,6.93; N,6.21; S,7.11; Cl,7.86%.

b) 4-Hydroxy-7-[2-[5-(3-phenylpropoxy)pentyl] aminoethyl]-1,3-benzothiazol-2(3H)-one hydrochloride i. N-[2-(4-Hydroxy-2-oxo-3H-1,3-benzothiazol-7-yl) ethyl]-5-(3-phenylpropoxy)-pentanamide mp 141°–142°;

Mass Spectrum: FAB 429 [(M+H)$^+$];

$^1$H NMR (CDCl$_3$) δ:1.60 (m, 2H), 1.70 (m, 2H), 1.87 (m, 2H), 2.18 (t, 2H), 2.66 (t, 2H), 2.74 (t, 2H), 3.40 (m, 4H), 3.49 (q, 2H), 6.18 (t, 1H), 6.74 (d, 1H), 6.80 (d, 1H), 7.18 (m, 3H), 7.27 (m, 2H), 8.71 (brs, 4H), 10.07 (s, 1H);

Analysis: Found; C,64.14; H,6.57; N,6.77; S,7.45%.

$C_{23}H_{28}N_2O_4S$ requires: C,64.46; H,6.58; N,6.54; S,7.48%.

ii. 4-Hydroxy-7-[2-[5-(3-phenylpropoxy)pentyl] aminoethyl]-1,3-benzothiazol-2(3H)-one hydrochloride mp 211°–212°;

Mass Spectrum: FAB 415 [(M+H)$^+$];

$^1$H NMR (D$_6$-DMSO) δ:1.38 (m, 2H), 1.51 (m, 2H), 1.61 (m, 2H), 1.79 (m, 2H), 2.61 (t, 2H), 2.86 (m, 4H), 3.06 (brm, 2H), 3.35 (m, 4H), 6.76 (d, 1H), 6.86 (d, 1H), 7.17 (m, 3H), 7.27 (m, 2H), 8.81 (brs, 2H), 10.13 (s, 1H), 11.77 (s, 1H);

Analysis: Found; C,60.83; H,7.02; N,6.21; S,6.94; Cl,8.04%.

$C_{23}H_{30}N_2O_3S.HCl$ requires: C,61.25; H,6.93; N,6.21; S,7.11; Cl,7.88%.

c) 4-Hydroxy-7-[2-[5-[2-(5-methylfuranyl)]pentyl] aminoethyl]-1,3-benzothiazol-2(3H)-one trifluoroacetate i. N-[2-(4-Hydroxy-2-oxo-3H-1,3-benzothiazol-7-yl) ethyl]-5-(5-methylfuran-2-yl)pentanamide mp 153°–154°;

Mass Spectrum: FAB 375 [(M+H)$^+$];

$^1$H NMR (D$_6$-DMSO) δ:1.47–1.51 (m, 4H), 2.03–2.04 (m, 2H), 2.20 (s, 3H), 2.5 (2H+DMSO), 2.59 (t, 2H), 3.23 (q, 2H), 5.90–5.92 (m, 2H), 6.69 (d, 1H), 6.78 (d, 1H), 7.87 (t, 1H), 9.89 (s, 1H), 11.61 (s, 1H).

ii. 4-Hydroxy-7-[2-[5-[2-(5-methylfuranyl)] pentylaminoethyl]-1,3-benzothiazol-2(3H)-one trifluoroacetate mp 237°–239° (decomposes);

$^1$H NMR (D$_6$-DMSO) δ:1.30–1.38 (m, 2H), 1.53–1.64 (m, 4H), 2.20 (s, 3H), 2.54 (t, 2H), 2.81 (brt, 2H), 2.94 (t, 2H), 3.10 (t, 2H), 5.93 (m, 2H), 6.75 (d, 1H), 6.86 (d, 1H), 8.56 (brs, 2H), 10.17 (brs, 1H), 11.73 (brs, 1H);

Analysis: Found; C,53.27; H,5.46; N,6.00; S,6.66%.

$C_{19}H_{24}N_2O_3S.CF_3CO_2H.H_2O$ requires: C,53.04; H,5.51; N,5.89; S,6.80%.

d) 4-Hydroxy-7-[2-[7-(2-phenylethoxy)heptyl] aminoethyl]-1,3-benzothiazol-2(3H)-one hydrochloride i. N-[2-(4-Hydroxy-2-oxo-3H-1,3-benzothiazol-7-yl) ethyl]-7-(2-phenylethoxy)-heptanamide mp 140–142°;

$^1$H NMR (D$_6$-DMSO) δ: 1.17–1.24 (m, 4H), 1.43–1.48 (m, 4H), 2.00 (t, 2H), 2.58 (t, 2H), 2.79 (t, 2H), 3.23 (q, 2H), 3.33–3.67 (m, 2H), 3.54 (t, 2H), 6.69 (d, 1H), 6.78 (d, 1H), 7.16–7.29 (m, 5H), 7.48 (t, 1H), 9.89 (s, 1H), 11.61 (s, 1H);

ii. 4-Hydroxy-7-[2-[7-(2-phenylethoxy)heptyl] aminoethyl]-1,3-benzothiazol-2(3H)-one hydrochloride mp 225°–227°;

$^1$H NMR (D$_6$-DMSO) δ:1.26 (brs, 6H), 1.43–1.52 (m, 2H), 1.54–1.64 (m, 2H), 2.79 (t, 2H), 2.86–2.92 (m, 4H), 3.01–3.11 (m, 2H), 3.67 (t, 2H+H$_2$O), 3.56 (t, 2H), 6.78 (d, 1H), 6.87 (d, 1H), 7.16–7.30 (m, 5H), 8.98 (brs, 2H), 10.16 (s, 1H), 11.79 (s, 1H);

Analysis: Found; C,61.70; H,7.12; N,6.20; S,6.92%.

$C_{24}H_2N_2O_3S.HCl$ requires: C,61.98; H,7.15; N,6.02; S,6.89%.

e) 4-Hydroxy-7-[2-[4-(2-phenylethoxy)butyl] aminoethyl]-1,3-benzothiazol-2(3H)-one hydrochloride i. N-[2-(4-Hydroxy-2-oxo-3H-1,3-benzothiazol-7-yl) ethyl]-4-(2-phenylethoxy)-butanamide Mass Spectrum: FAB 401 [(M+H)$^+$];

$^1$H NMR (CDCl$_3$+D$_6$-DMSO) δ:1.67–1.81 (m, 2H), 2.09 (t, 2H), 2.61 (t, 2H), 2.77 (t, 2H), 3.30–3.36 (m, 4H), 3.53 (t, 2H), 6.40 (brs, 1H), 6.66 (d, 1H), 6.71 (d, 1H), 7.12–7.20 (m, 5H), 8.88 (brs, 1H), 10.49 (brs, 1H).

ii. 4-Hydroxy-7-[2-[4(2-phenylethoxy)butyl] aminoethyl]-1,3-benzothiazol-2(3H)-one hydrochloride mp 204°–205°;

$^1$H NMR (D$_6$-DMSO) δ:1.52–1.57 (m, 2H), 1.61–1.69 (m, 2H), 2.80 (t, 2H), 2.84–2.89 (m, 4H), 3.02 (brm, 2H), 3.40 (t, 2H), 3.57 (t, 2H), 6.78 (d, 1H), 6.87 (d, 1H), 7.15–7.29 (m, 5H), 8.96 (brs, 2H), 10.18 (s, 1H), 11.80 (s, 1H);

Analysis: Found; C,59.40; H,6.51; N,6.56; S,7.77; Cl,8.00%.

$C_{21}H_{26}N_2O_3S.HCl$ requires: C,59.64; H,6.20; N,6.62; S,7.58; Cl,8.30%.

f) 4-Hydroxy-7-[2-[5-(2-phenylethoxy)pentyl]
aminoethyl]-1,3-benzothiazol-2(3H)-one
hydrochloride i. N-[2-(4-Hydroxy-2-oxo-3H-1,3-benzothiazol-7-yl)
ethyl]-5-(2-phenylethoxy)-pentanamide Mass Spectrum: FAB 415 [(M+H)$^+$];

$^1$H NMR (CDCl3) δ:1.50–1.60 (m, 2H), 1.60–1.70 (m, 2H), 2.18 (brt, 2H), 2.67 (m, 2H), 2.86 (t, 2H), 3.44 (t, 2H), 3.45–3.53 (m, 2H), 3.66 (t, 2H), 6.30 (brs, 1H), 6.65 (d, 1H), 6.72 (d, 1H), 7.19–7.26 (m, 6H), 9.60 (s, 1H).

ii. 4-Hydroxy-7-[2-[5-(2-phenylethoxy)
pentylaminoethyl]-1,3-benzothiazol-2(3H)-one
hydrochloride mp 209°–210°;

$^1$H NMR (D$_6$-DMSO) δ:1.28–1.35 (m, 2H), 1.48–1.52 (m, 2H), 1.57–1.68 (m, 2H), 2.80 (t, 2H), 2.85–2.94 (m, 4H), 3.05 (brs, 2H), 3.38 (t, 2H+H$_2$O), 3.56 (t, 2H), 6.78 (d, 1H), 6.87 (d, 1H), 7.19–7.30 (m, 5H), 8.93 (brs, 2H), 10.16 (s, 1H), 11.79 (s, 1H);

Analysis: Found; C,60.09; H,6.45; N,6.36; Cl,9.30%.

C$_{22}$H$_{28}$N$_2$O$_3$S.HCl requires: C,60.47; H,6.69; N,6.41; Cl,8.11%.

g) -Hydroxy-7-[2-[6-(phenylmethoxy)hexyl]
aminoethyl]-1,3-benzothiazol-2(3H)-one
hydrochloride i. N-[2-(4-Hydroxy-2-oxo-3H-1,3-benzothiazol-7-yl)
ethyl]-6-(phenylmethoxy)-hexanamide mp 133°–134°;

Mass Spectrum: FAB 429 [(M+H)$^+$];

$^1$H NMR (D$_6$-DMSO) δ:1.2–1.3 (m, 2H), 1.4–1.55 (m, 4H), 2.01 (t, 2H), 2.57 (t, 2H), 3.2–3.3 (m, 2H), 3.3–3.4 (m, 2H), 4.44 (s, 2H), 6.69 (d, 1H), 6.78 (d, 1H), 7.24–7.37 (m, 5H), 7.85 (t, 1H), 9.91 (s, 1H), 11.61 (s, 1H).

ii. 4-Hydroxy-7-[2-[6-(phenylmethoxy)hexyl]
aminoethyl]-1,3-benzothiazol-2(3H)-one
hydrochloride mp 208°–211°;

$^1$H NMR (D$_6$-DMSO) δ:1.27–1.38 (m, 4H), 1.5–1.65 (m, 4H), 2.81–2.94 (m, 4H), 3.02–3.11 (m, 2H), 3.42 (t, 2H), 4.45 (s, 2H), 6.76 (d, 1H), 6.86 (d, 1H), 7.25–7.38 (m, 5H), 8.81 (brs, 2H), 10.13 (s, 1H), 11.77 (s, 1H);

Analysis: Found; C,59.42; H,6.85; N,6.37; S,7.25; Cl,9.44%.

C$_{22}$H$_{28}$N$_2$O$_3$S.HCl requires for 0.17 moles excess HCl: C,59.55; H,6.63; N,6.31; S,7.23; Cl,9.45%.

h) 4Hydroxy-7-[2-[4-(4-phenylbutoxy)butyl]
aminoethyl]-1,3-benzothiazol-2(3H)-one
hydrochloride i. N-[2-(4-Hydroxy-2-oxo-3H-1,3-benzothiazol-7-yl)
ethyl]-4-(4-phenylbutoxy)-butanamide mp 133°–135°;

Mass Spectrum: FAB 429 [(M+H)$^+$];

$^1$H NMR (CDCl$_3$) δ:1.06–1.23 (m, 4H), 1.36 (q, 2H), 1.73 (t, 2H), 2.11–2.17 (m, 4H), 2.23 (t, 2H), 2.91–2.94 (m, 4H), 6.25 (d, 1H), 6.31 (d, 1H), 6.66–6.81 (m, 6H), 8.67 (s, 1H), 10.42 (s, 1H).

ii. 4-Hydroxy-7-[2-[4-(4-phenylbutoxy)butyl]
aminoethyl]-1,3-benzothiazol-2(3H)-one
hydrochloride mp 208°;

$^1$H NMR (D$_6$-DMSO) δ:1.6 (brm, 8H), 2.58 (t, 2H), 2.88 (brm, 4H), 3.05 (t, 2H), 3.45 (m, 4H+H$_2$O), 6.77 (d, 1H), 6.86 (d, 1H), 7.18 (m, 3H), 7.26 (m, 2H), 8.91 (brs, 2H), 10.16 (s, 1H);

Analysis: Found; C,59.21; H,7.08; N,6.17; S,7.22; Cl,8.16%.

C$_{23}$H$_{30}$N$_2$O$_3$S.HCl.0.9H$_2$O requires: C,58.90; H,7.03; N,5.97; S,6.82; Cl,7.60%.

i) 4-Hydroxy-7-[2-(6-phenoxyhexyl)aminoethyl]-1,3-benzothiazol-2(3H)-one hydrochloride i. N-[2-(4-Hydroxy-2-oxo-3H-1,3-benzothiazol-7-yl)
ethyl]-6-phenoxyhexanamide mp 161.5°–162.5°;

Mass Spectrum: FAB 407 [(M+H)$^+$];

$^1$H NMR (D$_6$-DMSO) δ:1.30–1.39 (m, 2H), 1.48–1.57 (q, 2H), 1.64–1.72 (m, 2H), 2.03–2.06 (t, 2H), 2.57–2.61 (t, 2H), 3.21–3.26 (m, 2H), 3.90–3.94 (t, 2H), 6.68–6.80 (m, 2H), 6.88–6.91 (m, 3H), 7.24–7.29 (t, 2H), 7.85–7.89 (t, 1H).

ii. 4-Hydroxy-7-[2-(6-phenoxyhexyl)aminoethyl]-1,3-benzothiazol-2(3H)-one hydrochloride mp 213°–214°;

$^1$H NMR (D$_6$-DMSO) δ:1.26–1.50 (m, 4H), 1.55–1.65 (quin, 2H), 1.65–1.78 (quin, 2H), 2.80–2.85 (t, 2H), 2.90–2.94 (t, 2H), 3.06–3.09 (t, 2H), 3.94–3.97 (t, 2H), 6.74+6.87 (2×d, 2H), 6.90–6.93 (m, 3H), 7.25–7.29 (t, 2H), 8.59 (brs, 2H), 10.10 (brs, 2H);

Analysis: Found; C,58.93; H,6.49; N,6.71; S,6.94%.

C$_{21}$H$_{26}$N$_2$O$_3$S.HCl.0.36H$_2$O requires: C,58.74; H,6.50; N,6.52; S,7.47%.

j) 4-Hydroxy-7-[2-[6-(3-phenylpropoxy)hexyl]
aminoethyl]-1,3-benzothiazol-2(3H)-one oxalate i. N-[2-(4-Hydroxy-2-oxo-3H-1,3-benzothiazol-7-yl)
ethyl]-6-(3-phenylpropoxy)-hexanamide Mass Spectrum: FAB 443 [(M+H)$^+$].

ii. 4-Hydroxy-7-[2-[6-(3-phenylpropoxy)hexyl]
aminoethyl]-1,3-benzothiazol-2(3H)-one oxalate mp 238°–240° (decomposes);

$^1$H NMR (D$_6$-DMSO) δ:1.31 (brs, 4H), 1.42–1.67 (m, 4H), 1.74–1.81 (quin, 2H), 2.58–2.63 (t, 2H), 2.79–2.85 (brt, 2H), 2.89–2.93 (brt, 2H), 3.05–3.10 (brt, 2H), 3.92–3.55 (t, 4H), 6.74–6.76 (d, 1H), 6.84–6.86 (d, 1H), 7.15–7.29 (m, 5H), 8.4–9.2 (v.brs, not integrated);

Analysis: Found; C,59.30; H,6.49; N,5.17%.

C$_{24}$H$_{32}$N$_2$O$_3$S.1.6 C$_2$H$_2$O$_4$ requires: C,59.30; H,6.44; N,5.26%.

k) 4-Hydroxy-7-[2-[2-(4-methoxyphenyl)ethyl]
aminoethyl]-1,3-benzothiazol-2(3H)-one
hydrochloride i. N-[2-(4-Hydroxy-2-oxo-3H-1,3-benzothiazol-7-yl)
ethyl]-(4-methoxyphenyl)-acetamide Mass Spectrum: FAB 359 [(M+H)$^+$].

ii. 4-Hydroxy-7-[2-[2-(4-methoxyphenyl)ethyl]
aminoethyl]-1,3-benzothiazol-2(3H)-one
hydrochloride mp 275°–280°;

Mass Spectrum: FAB 345 [(M+H)$^+$];

$^1$H NMR (D$_6$-DMSO) δ:2.80–2.90 (m, 4H), 3.10–3.20 (brm, 4H), 3.73 (s, 3H), 6.77 (d, 1H), 6.86 (d, 1H), 6.90 (d, 2H), 7.18 (d, 2H), 9.00 (brs, 2H), 10.15 (s, 1H), 11.78 (s, 1H);

Analysis: Found; C,56.52; H,5.48; N,7.23%.

C$_{18}$H$_{20}$N$_2$O$_3$S.HCl requires: C,56.76; H,5.56; N,7.35 %.

1) 4-Hydroxy-7-[2-[2,2-dimethyl-6-(2-phenylethoxy)hexyl]aminoethyl[-1,3-benzothiazol-2(3H)-one hydrochloride i. N-[2-(4-Hydroxy-2-oxo-3H-1,3-benzothiazol-7-yl)ethyl]-2,2-dimethyl-6-(2-phenylethoxy)hexanamide mp 136°–138°;

Mass Spectrum: FAB 457 [(M+H)$^+$]; h $^1$H NMR (D$_6$-DMSO) δ:1.00 (s, 6H), 1.08–1.12 (m, 2H), 1.34–1.41 (m, 4H), 2.60 (t, 2H), 2.77 (t, 2H), 3.25 (q, 2H), 3.32 (t, 2H), 3.53 (t, 2H), 6.69 (d, 1H), 6.77 (d, 1H), 7.15–7.27 (m, 5H), 7.49 (t, 1H), 9.88 (brs, 1H), 11.61 (brs, 1H);

Analysis: Found; C,65.84; H,7.31; N,6.49; S,6.81%.

C$_{25}$H$_{32}$N$_2$O$_4$S requires: C,65.76; H,7.06; N,6.16; S,7.02%.

ii. 4-Hydroxy-7-[2-[2,2-dimethyl-6-(2-phenylethoxy)hexyl]aminoethyl]-1,3-benzothiazol-2(3H)-one hydrochloride mp 224°–225°;

Mass Spectrum: FAB 443 [(M+H)$^+$];

$^1$H NMR (D$_6$-DMSO) δ:0.96 (s, 6H), 1.21–1.30 (m, 4H), 1.45–1.48 (m, 2H), 2.78–2.82 (m, 4H), 2.95–2.99 (m, 2H), 3.02–3.12 (m, 2H), 3.39 (t, 2H), 3.57 (t, 2H), 6.78 (d, 1H), 6.87 (d, 1H), 7.16–7.29 (m, 5H), 8.58 (brs, 2H), 10.17 (s, 1H), 11.78 (s, 1H);

Analysis: Found; C,62.62; H,7.51; N,5.91; S,6.67; Cl,8.11%.

C$_{25}$H$_{34}$N$_2$O$_3$S.HCl requires: C,62.27; H,7.36; N,5.85; S,6.69; Cl,7.40%.

m) 4-Hydroxy-7-[2-[6-(2-phenylethylsulphonyl)hexyl]aminoethyl]-1,3-benzothiazol-2(3H)-one hydrochloride i. N-2-(4-Hydroxy-2-oxo-1,3-benzothiazol-7-yl)ethyl]-6-(2-phenylethylsulphonyl)-hexanamide mp 174°–188°;

Mass Spectrum: FAB 477 [(M+H)$^+$];

$^1$H NMR (D$_6$-DMSO) δ:1.27–1.33 (m, 2H), 1.44–1.52 (m, 2H), 1.61–1.70 (m, 2H), 2.01–2.05 (t, 2H), 2.57–2.61 (t, 2H), 2.98–3.07 (m, 4H), 3.20–3.26 (m, 2H), 3.37–3.43 (m, 2H), 6.69–6.86 (dd, 2H), 7.21–7.31 (m, 5H), 7.86–7.89 (t, 1H), 9.91 (s, 1H), 11.62 (s, 1H).

ii. 4-Hydroxy-7-[2-[6-(2-phenylethylsulphonyl)hexyl]aminoethyl]-1,3-benzothiazol-2(3H)-one hydrochloride mp 210°–211°;

Mass Spectrum: FAB 463 [(M+H)$^+$];

$^1$H NMR (D$_6$-DMSO) δ:1.35 (brs, 4H), 1.60 (brm, 2H), 1.68 (brm, 2H), 2.83–2.91 (m, 4H), 2.98–3.10 (m, 6H), 3.37–3.42 (m, 2H), 6.75–6.88 (dd, 2H), 7.23–7.26 (m, 1H), 7.31–7.32 (m, 4H), 8.7 (v.brs, 2H);

Analysis: Found; C,52.93; H,6.15; N,5.59; S,12.15%.

C$_{23}$H$_{30}$N$_2$O$_4$S.HCl.H$_2$O requires: C,53.40; H,6.43; N,5.41; S,12.39%.

n) N-[6-[2-(4-Hydroxy-2-oxo-3H-1,3-benzothiazol-7-yl)ethylamino]hexyl]-N'-phenyl urea hydrochloride i. N-[2-(4-Hydroxy-2-oxo-1,3-benzothiazol-7-yl)ethyl]-6-(phenylaminocarbonylamino)-hexanamide mp 186°–188°;

Mass Spectrum: 443 [(M+H)$^+$];

$^1$H NMR (D$_6$-DMSO) δ:1.23–1.27 (m, 2H), 1.36–1.52 (m, 4H), 2.01–2.05 (t, 2H), 2.56–2.60 (t, 2H), 2.60–3.05 (q, 2H), 3.23 (q, 2H), 6.09 (t, 2H), 6.68–6.79 (dd, 2H), 687 (t, 1H), 7.19 (t, 2H), 7.35–7.37 (d, 2H), 7.86 (t, 2H), 8.37 (s, 1H).

ii. N-[6-[2-(4-Hydroxy-2-oxo-3H-1,3-benzothiazol-7-yl)ethylamino]hexyl]-N'-phenyl urea hydrochloride mp 209°–210°;

Mass Spectrum: FAB 429 [(M+H)$^+$];

$^1$H NMR (D$_6$-DMSO) δ:1.25–1.65 (m, 8H), 2.75–3.15 (m, 8H), 6.18–6.21 (t, 1H), 6.73–6.76 (d, 1H), 6.85–6.89 (t, 2H), 7.18–7.22 (t, 2H), 7.36–7.38 (d, 2H), 8.45 (brs, 3H), 10.13 (s, 1H), 11.75 (s, 1H);

Analysis: Found; C,52.55; H,5.35; N,10.24; S,5.15%.

C$_{21}$H$_{29}$N$_4$O$_3$S.HCl.0.64 CF$_3$CO$_2$H requires: C,51.99; H,5.55; N,10.41; S,5.96%.

o) 4-Hydroxy-7-[2-[6-[2-(4-nitrophenyl)ethoxy]hexyl]aminoethyl]-1,3-benzothiazol-2(3H)-one hydrochloride Prepared by the method of Example 1b) using the amide of Example 11a).

mp 160°–163°;

Mass spectrum: FAB 460 [(M+H)$^+$];

$^1$H NMR (D$_6$-DMSO) δ:1.27 (m, 4H), 1.45 (m, 2H), 1.58 (m, 2H), 2.86 (m, 4H), 2.95 (t, 2H), 3.05 (brm, 2H), 3.38–3.62 (t, 2×2H), 6.76–6.86 (dd, 2H), 7.53–8.15 (dd, 4H), 8.88 (2H), 10.14 (s, 1H), 11.77 (s, 1H);

Analysis: Found; C,55.35; H,6.08; N,8.48; S,6.62; Cl,7.80%.

C$_{23}$H$_{29}$N$_3$O$_5$S.HCl requires: C,55.69; H,6.09; N,8.47; S,6.42; Cl,7.15%.

p) 4-Hydroxy-7-[2-[6-[2-(4-hydroxyphenyl)ethoxy]-2,2-dimethylhexyl]aminoethyl]-1,3-benzothiazol-2(3H)-one hydrochloride i. 6-[2-(4-Hydroxyphenyl)ethoxy]-N-[2-(4-hydroxy-2-oxo-3H-1,3-benzothiazol-7-yl)ethyl]-2,2-dimethylhexanamide Mass Spectrum: FAB 473 [(M+H)$^+$];

$^1$H NMR (D$_4$-MeOH) δ:0.98 (s)+1.00–1.05 (m) (8H), 1.29–1.37 (m, 4H), 2.60–2.65 (m, 4H), 3.25–3.47 (m, 6H+H$_2$O), 6.55–6.60 (m, 3H), 6.73–6.75 (d, 1H), 6.89–6.92 (dd, 2H).

ii. 4-Hydroxy-7-[2-[6-[2-(4-hydroxyphenyl)ethoxy]-2,2-dimethylhexyl]aminoethyl]-1,3-benzothiazol-2 (3H)-one hydrochloride mp 204°–205°;

Mass Spectrum: FAB 459 [(M+H)⁺];

¹H NMR (D₆-DMSO) δ:0.95 (s, 6H), 1.25 (brs, 4H), 1.45–1.48 (brt, 2H), 2.65–2.69 (t, 2H), 2.81 (brs, 2H), 2.90–2.95 (brm, 2H), 3.07 (brs, 2H), 3.37 (m, 2H+H₂O), 3.47–3.51 (t, 2H), 6.64–6.67 (d, 2H), 6.75–6.77 (d, 1H), 6.85–6.87 (d, 1H), 6.99–7.01 (d, 2H), 8.35 (brs, 2H), 9.2 (s, 1H), 10.1 (s, 1H), 11.8 (s, 1H);

Analysis: Found; C,58.07; H,7.29; N,5.42; S,6.19%.

C₂₅H₃₄N₂O₄S.HCl (1.22M H₂O) requires: C,58.07; H,7.41; N,5.46; S,5.84%.

q) 7-Hydroxy-4-[2-[6-[2-(1-naphthyl)ethoxy]hexyl]aminoethyl]-1,3-benzothiazol-2(3H)-one hydrochloride i. N-[2-(4-Hydroxy-2-oxo-3H-1,3-benzothiazol-7-yl)ethyl]-6-[2-(1-naphthyl)ethoxy]-hexanamide Mass Spectrum: FAB 479 [(M+H)⁺].

ii. 7-Hydroxy-4-[2-[6-[2-(1-naphthyl(ethoxy]hexyl]aminoethyl]-1,3-benzothiazol-2(3H)-one hydrochloride mp 194°–196°;

Mass Spectrum: FAB 465 [(M+H)⁺];

¹H NMR (D₆-DMSO) δ:1.27 (brs, 4H), 1.47 (brs, 2H), 1.57 (brs, 2H), 2.86 (brd, 4H), 3.04 (brs, 2H), 3.28 (t, 2H), 3.40 (t, 2H), 3.68 (t, 2H), 6.76 (d, 1H), 6.86 (d, 1H), 7.43 (m, 2H), 7.52 (m, 2H), 7.78 (d, 1H), 7.91 (d, 1H), 8.68 (d, 1H), 9.8 (brs, 2H), 10.13 (s, 1H), 11.77 (s, 1H);

Analysis: Found; C,64.47; H,6.69; N,5.71; S,6.19%.

C₂₇H₃₂N₂O₃S.HCl requires: C,64.71; H,6.64; N,5.59; S,6.40%.

r) 7-[2-[6-(2-Cyclohexylethoxy)hexyl]aminoethyl]-4-hydroxy-1,3-benzothiazol-2(3H)-one hydrochloride i. 6-(2-Cyclohexylethoxy)-N-[2-(4-hydroxy-2-oxo-3H-1,3-benzothiazol-7-yl)ethyl]-hexanamide Mass Spectrum: FAB 435 [(M+H)⁺];

¹H NMR (CDCl₃+D₆-DMSO) δ:0.85 (m, 2H), 1.0–1.7 (m, 17H), 2.1 (t, 2H), 2.6 (t, 2H), 3.3 (m, 6H), 6.7 (d, 1H), 6.5 (d, 1H), 6.9 (t, 1H), 10.7 (brs, 1H).

ii. 7-[2-[6-(2-Cyclohexylethoxy)hexyl]aminoethyl]-4-hydroxy-1,3-benzothiazol-2(3H)-one hydrochloride mp 224°–227°;

Mass Spectrum: FAB 421 [(M+H)⁺];

¹H NMR (D₆-DMSO) δ:0.88 (m, 2H), 1.0–1.25 (m, 3H), 1.25–1.40 (m, 7H), 1.40–1.55 (m, 2H), 1.55–1.7 (m, 7H), 2.83 (m, 2H), 2.90 (m, 2H), 3.05 (m, 2H), 3.0–3.4 (m, 4H+H₂O), 6.75 (d, 1H), 6.86 (d, 1H), 8.7 (brs, 2H), 10.11 (s, 1H), 11.76 (brs, 1H);

Analysis: Found; C,59.88; H,8.08; N,6.19; S,6.18; Cl,8.69%.

C₂₃H₃₆N₂O₃S.HCl requires: C,59.88; H,8.11; N,6.07; S,6.95; Cl,8.57%.

s) 7-[2-[6-[2-(4-Bromophenylethoxy]hexyl]aminoethyl]-4-hydroxy-1,3-benzothiazol-2(3H)-one hydrochloride i. 6-[2-(4-Bromophenyl)ethoxy]-N-[2-(4-hydroxy-2-oxo-3H-1,3-benzothiazol-7-yl)-ethyl]hexanamide mp 143°–145°;

Mass Spectrum: FAB 507/9 [(M+H)⁺];

¹H NMR (D₆-DMSO) δ:1.15–1.24 (m, 2H), 1.42–1.49 (m, 4H), 2.01 (t, 2H), 2.59 (t, 2H), 2.76 (t, 2H), 3.18–3.30 (m, 2H), 3.33 (t, 2H), 3.53 (t, 2H), 6.70 (d, 1H), 6.79 (d, 1H), 7.19 (d, 2H), 7.45 (d, 2H), 7.85 (t, 1H), 9.5–11.5 (vbrs, 2H);

Analysis: Found; C,54.39; H,5.30; N,5.63; S,5.14; Br,16.96%.

C₂₃H₂₇N₂O₄SBr requires: C,54.44; H,5.36; N,5.52; S,6.32; Br,15.74%.

ii. 7-[2-[6-[2-(4-Bromophenylethoxy]hexyl]aminoethyl]-4-hydroxy-1,3-benzothiazol-2(3H)-one hydrochloride mp 199°–200°;

Mass Spectrum: FAB 577/9 [(M+Rb)⁺];

¹H NMR (D₆-DMSO) δ:1.22–1.37 (m, 4H), 1.42–1.51 (m, 2H), 1.57–1.64 (m, 2H), 2.77 (t, 2H), 2.85–2.96 (m, 4H), 3.06 (t, 2H), 3.36 (t, 2H+H₂O), 3.55 (t, 2H), 6.78 (d, 1H), 6.87 (d, 1H), 7.20 (d, 2H), 7.46 (d, 2H), 9.1 (v.brs, 1H), 10.2 (v.brs, 1H);

Analysis: Found; C,51.98; H,5.68; N,5.39; S,5.94; Cl,7.02%.

C₂₃H₂₉N₂O₃SBr.HCl requires: C,52.13; H,5.71; N,5.29; S,6.05; Cl,6.69%.

t) 4-Hydroxy-7-[2-[6-[2-(2-thienyl)ethoxy]hexyl]aminoethyl]-1,3-benzothiazol-2(3H)-one hydrochloride I. N-[2-(4-Hydroxy-2-oxo-3H-1,3-benzothiazol-7-yl)ethyl]-6-[2-(2-thienyl)ethoxy]-hexanamide mp 130°–132°;

Mass Spectrum: FAB 435 [(M+H)⁺];

¹H NMR (D₆-DMSO) δ:1.16–1.29 (m, 2H), 1.40–1.57 (m, 4H), 2.01 (t, 2H), 2.59 (t, 2H), 3.00 (2H, t), 3.20–3.37 (m, 2H), 3.35–3.45 (m, 2H+H₂O), 3.56 (t, 2H), 6.70 (d, 1H), 6.79 (d, 1H), 6.89 (brs, 1H), 6.92–6.94 (m, 1H), 7.70 (d, 1H), 7.83–7.91 (m, 1H), 9.96 (brs, 1H), 11.58 (brs, 1H);

Analysis: Found; C,57.76; H,6.06; N,6.64; S,14.48%.

C₂₁H₂₆N₂O₄S₂ requires: C,58.04; H,6.03; N,6.45; S,14.48%.

ii. 4-Hydroxy-7-[2-[6-[2-(2-thienyl)ethoxy]hexyl]aminoethyl]-1,3-benzothiazol-2(3H)-one hydrochloride mp 216°–218°;

Mass Spectrum: FAB 421 [(M+H)⁺];

¹H NMR (D₆-DMSO) δ:1.31 (brs, 4H), 1.47–1.53 (m, 2H), 1.54–1.66 (m, 2H), 2.84–2.93 (m, 4H), 2.87 (t, 2H), 2.89 (brs, 2H), 3.40 (t, 2H), 3.57 (t, 2H), 6.77 (d, 1H), 6.87 (d, 1H), 6.89 (brs, 1H), 6.92–6.95 (m, 1H), 7.31 (dd, 1H), 9.01 (brs, 1H), 10.16 (s, 1H), 11.78 (s, 1H);

Analysis: Found; C,55.40; H,6.47; N,6.28; S,13.86; Cl,7.38%.

C₂₁H₂₈N₂O₃S₂.HCl requires: C,55.11; H,6.39; N,6.13; S,14.02; Cl,7.76%.

u) (R,S)-4-Hydroxy-7-[2-[2-methyl-6-(2-phenylethoxy)hexyl]aminoethyl]-1,3-benzothiazol-2(3H)-one hydrochloride i. N-[2-(4-Hydroxy-2-oxo-3H-1,3-benzothiazol-7-yl)ethyl]-2-methyl-6-(2-phenylethoxy)hexanamide Mass Spectrum: 443 [(M+H)⁺].

ii. (R,S)-4-Hydroxy-7-[2-[2-methyl-6-(2-phenylethoxy)hexyl]aminoethyl]-1,3-benzothiazol-2(3H)-one hydrochloride mp 211°–212°;

Mass Spectrum: FAB 429 [(M+H)⁺];

$^1$H NMR (D$_6$-DMSO) δ:0.94 (d, 3H), 1.11–1.51 (m, 6H), 1.80–1.85 (m, 1H), 2.70–2.93 (m, 6H), 3.01–3.11 (m, 2H), 3.38 (t, 2H), 3.56 (t,. 2H), 6.78 (d, 1H), 6.86 (d, 1H), 7.16–7.29 (m, 5H), 8.82 (brs, 2H), 10.15 (s, 1H), 11.78 (s, 1H);

Analysis: Found; C,61.31; H,7.31; N,6.11; S,6.78%,

C$_{24}$H$_{32}$N$_2$OS.HCl requires: C,61.98; H,7.15; N,6.02; S,6.98%.

v) 1,3-Dihydro-4-hydroxy-7-[2-6-(2-phenylethoxy)hexyl]aminoethyl]-2H-benzimidazol-2-one hydrochloride i. N-[2-(1,3-Dihydro-4-hydroxy-2-oxo-2H-1,3-benzimidazol-7-yl)ethyl]-6-(2-phenylethoxy)hexanamide Prepared by the method of Example 1a) from 7-(2-aminoethyl)-4-hydroxy-benzimidazol-2(3H)-one hydrobromide, which was prepared from N-[2-(3-amino-4-methoxyphenyl)ethyl]trifluoroacetamide using a procedure outlined in *J. Med. Chem.*, 1987, 30, 1166.

mp 205°–207°;

Mass Spectrum: FAB 412 [(M+H)⁺];

$^1$H NMR (D$_6$-DMSO) δ:1.18–1.24 (m, 2H), 1.43–1.49 (m, 4H), 2.01 (t, 2H), 2.65 (t, 2H), 2.79 (t, 2H), 3.21 (q, 2H), 3.34 (m, 2H+H$_2$O), 3.55˙(t, 2H), 6.36 (d, 1H), 6.53 (d, 1H), 7.16–7.29 (m, 5H), 7.30 (t, 1H), 9.30 (s, 1H), 10.32 (s, 1H), 10.53 (s, 1H);

Analysis: Found; C,64.34; H,7.14; N,9.92%,

C$_{23}$H$_{29}$N$_3$O$_4$.0.88 H$_2$O requires: C,64.65; H,7.25; N,9.83%.

ii. 1,3-Dihydro-4-hydroxy-7-[2-[6-(2-phenylethoxy)hexyl]aminoethyl]-2H-benzimidazol-2-one hydrochloride mp 222°–224°;

Mass Spectrum: FAB 398 [(M+H)⁺];

$^1$H NMR (D$_6$-DMSO) δ:1.22–1.33 (m, 4H), 1.43–1.51 (m, 2H), 1.53–1.65 (m, 2H), 2.79 (t, 2H), 2.81–2.92 (m, 4H), 3.01–3.09 (m, 2H), 3.38 (m, 2H+H$_2$O), 3.56 (t, 2H), 6.41 (d, 1H), 6.62 (d, 1H), 7.16–7.30 (m, 5H), 8.73 (brs, 2H), 9.54 (s, 1H), 10.48 (s, 1H), 10.65 (s, 1H);

Analysis: Found; C,63.30; H,7.52; N,6.67; Cl,8.11%,

C$_{23}$H$_{31}$N$_3$O$_3$.HCl requires: C,63.65; H,7.43; N,6.68; Cl,8.17%.

EXAMPLE 3

4-Hydroxy-7-[2-[6-[2-(4-hydroxyphenyl)ethoxy]hexyl]aminoethyl]-1,3-benzothiazol-2(3H)-one trifluoroacetate a) N-[2-(4-Hydroxy-2-oxo-3H-1,3-benzothiazol-7-yl)ethyl]-6-[2-(4-phenylmethoxy)-phenylethoxy]hexanamide The subtitled amide was prepared according to the method of Example 1a).

mp 148°–150°;

Mass Spectrum: FAB 535 [(M+H)⁺];

$^1$H NMR (D$_6$-DMSO) δ:1.25–1.67 (m, 2H), 1.41–1.50 (m, 4H), 2.01 (t, 2H), 2.59 (t, 2H), 2.72 (t, 2H), 3.24 (q, 2H), 3.33 (t, 2H), 3.49 (t, 2H), 5.05 (s, 2H), 6.69–6.80 (2×d, 2H), 6.89–7.14 (dd, 4H), 7.30–7.44 (m, 5H), 9.92 (s, 1H), 11.63 (s, 1H).

b) 4-Hydroxy-7-[2-[6-[2-(4-phenylmethoxy)phenylethoxy]hexyl]aminoethyl]-1,3-benzothiazol-2(3H)-one hydrochloride The subtitled compound was prepared according to the method of Example 1b), from the intermediate amide of step a).

mp 228°–230°;

$^1$H NMR (D$_6$-DMSO) δ:1.29 (brs, 4H), 1.41–1.49 (m, 2H), 1.61 (brs, 2H), 2.70–2.74 (t, 2H), 2.85–2.90 (m, 4H), 3.05 (brs, 2H), 3.34–3.38 (t, 2H), 3.48–3.52 (t, 2H), 5.06 (s, 2H), 6.77–6.88 (2×d, 2H), 6.90–6.93+7.13–7.15 (dd, 4H), 7.30–7.43 (m, 5H), 8.9–9.0 (brs, 2H), 10.18 (brs, 1H), 11.80 (s, 1H);

Analysis: Found; C,64.84; H,6.80; N,5.17; S,5.55%,

C$_{30}$H$_{36}$N$_2$O$_4$S.HCl requires: C,64.69; H,6.64; N,5.03; S,5.75%.

c) 4-Hydroxy-7-[2-[6-[2-(4-hydroxyphenyl)ethoxy]hexyl]aminoethyl]-1,3-benzothiazol-2(3H)-one trifluoroacetate A solution of the benzyl ether from step b) (0.79 g) in methanol (50 ml) was treated with conc. hydrochloric acid to pH 1 and hydrogenated over 10% palladium on carbon (0.50 g) for 8 days, the catalyst being replaced with a fresh portion after 7 days. The mixture was diluted with methanol (100 ml) boiled for 10 min and hot filtered. The filtrate was evaporated to give a yellow semi-solid. HPLC, using methanol:0.1% TFA in water (50:50) as eluant, gave the title salt as a white powder.

mp 192°–197°;

$^1$H NMR (D$_6$-DMSO) δ:1.29 (brs, 4H), 1.48–1.56 (brm, 4H), 2.65–2.67 (t, 2H), 2.80–2.82 (t, 2H), 2.90+3.08 (brs, 4H), 3.36–3.38 (t, 2H+H$_2$O), 3.46–3.50 (t, 2H), 6.66+7.00 (dd, 4H), 6.75+6.86 (2×d, 2H);

Analysis: Found; C,55.01; H,5.85; N,5.12; S,5.29%,

C$_{23}$H$_{30}$N$_2$O$_4$S.CF$_3$CO$_2$H requires: C,55.24; H,5.56; N,5.15; S,5.90%.

EXAMPLE 4

2,3-Dihydro-7-hydroxy-4-[2-[6-(phenylethoxy)hexyl]aminoethyl]-indol-2-one hydrochloride a) N-[2-(3-Nitro-4phenylmethoxy)phenyl]ethyl]-N-phenylmethyl-6-(2-phenylethoxy)-hexanamide A solution of N,O-bis-(phenylmethyl)-2-(4-hydroxy-3-nitrophenyl)ethylamine (7.5 g), 6-[2-phenylethyoxy]-hexanoic acid (5.38 g) and carbonyldiimidazole (3.69 g) in dichloromethane (120 ml) was stirred at room temperature for 20 hours. Aqueous 5% hydrochloric acid (50 ml) was added and the mixture filtered, the organic layer was separated, washed with brine, (NaHCO$_3$), and again with brine. After drying (MgSO$_4$) the solvent was removed under reduced pressure and the residue purified by chromatography (SiO$_2$) using ether/60°–80° petroleum ether as eluant, to give the subtitled compound as a yellow oil.

Mass Spectrum: FAB 581 [(M+H)$^+$].

b) N-[2-(3-Amino-4-phenylmethoxy)phenyl]ethyl-N-phenylmethyl-6-(2-phenylethoxy)-hexanamide The amide from step a) (7.0 g) was added to a suspension of iron powder (7.0 g) and ammonium chloride (7.0 g) in aqueous ethanol (90 ml ethanol:70 ml water). The suspension was stirred and heated to reflux for 2 hours. The hot reaction mixture was filtered (Hyflo Supergel) and the filtrate evaporated under reduced pressure. The residue was partitioned between dichloromethane and water, the organic layer was separated, dried (MgSO$_4$) and evaporated under reduced pressure to give the subtitled compound as a yellow gum which was used without further purification.

Mass Spectrum: FAB 551 [(M+H)$^+$];

$^1$H NMR (CDCl$_3$) δ:1.35 (m, 2H), 1.57–1.65 (m, 4H), 2.28 (m, 2H), 2.65–2.73 (m, 2H), 2.88 (m, 2H), 3.40 (m, 2H), 3.51 (t, 2H), 3.61 (m, 2H), 3.91 (brs, 2H), 4.35 (s, 1H), 4.59 (s, 1H), 5.04 (s, 2H), 6.42–6.57 (m, 2H), 6.75 (d, 1H), 7.10 (d, 1H), 7.21–7.41 (m, 14H).

c) 3-Amino-N-[6-(2-phenylethoxy)hexyl]-4-phenylmethoxy-N-phenylmethyl-2-benzeneethanamide Borane (1M in THF, 20 ml) was added to a stirred solution of the compound from step b) (6.27 g) in tetrahydrofuran. The solution was heated under reflux for 18 hours, cooled and methanol (5 ml) added. The solvent was removed under reduced pressure and the residue dissolved in methanol. Ethanolic HCl was added and the solution heated under reflux for 40 min, the solvent removed under reduced pressure, and the compound converted to the free base which was used in the next step without further purification.

Mass Spectrum: FAB 537 [(M+H)$^+$].

d) 1,3-Dihydro-3-methylthio-4-[2-[N-[6-(2-phenylethoxy)hexyl]-N-(phenylmethyl)-amino]ethyl]-7-phenylmethoxy-2H-indol-2-one Sulfuryl chloride (0.81 ml) in dichloromethane was added dropwise to a solution of ethyl methylthioacetate in dichloromethane (25 ml) at −74°. The solution was stirred for 45 min and a solution of the compound from step c) (4.35 g) and Proton Sponges (1.74 g) in dry dichloromethane (50 ml) added dropwise. The mixture was stirred at −74° for 4 hours then triethylamine (1.17 ml) added. The mixture was allowed to warm to room temperature and stirred overnight. Aqueous 5% hydrochloric acid (35 ml) was added and stirring continued for 1 hour. The organic layer was separated, dried (MgSO$_4$) and the solvent removed under reduced pressure. Chromatography (SiO$_2$) using methanol/dichloromethane as eluant gave the subtitled compound as a green oil.

Mass Spectrum: FAB 623 [(M+H)$^+$].

e) 1,3-Dihydro-4-[2-[N-[6-(2-phenylethoxy)hexyl]-N-(phenylmethyl)amino]ethyl]-7-phenylmethoxy-2H-indol-2-one Raney nickel (1.5 g) was added to a solution of the compound from step d) (2.1 g) in dry ethanol (60 ml). The mixture was heated to reflux for 1 hour, the catalyst was removed by filtration and the filtrate evaporated under reduced pressure. Trituration with ether gave an off-white solid which was purified by reverse phase HPLC (SiO$_2$) using methanol:chloroform as eluant. Recrystallisation from isopropyl alcohol gave the subtitled compound as a buff coloured solid.

mp 183°–185°;

Mass Spectrum: FAB 577 [(M+H)$^+$];

$^1$H NMR (CDCl$_3$) δ:1.34 (m, 4H), 1.55 (m, 2H), 1.90 (m, 2H), 2.87 (t, 2H), 2.8–3.2 (m, 6H), 3.3–3.5 (q, 4H), 3.61 (t, 2H), 4.22 (d, 2H), 5.07 (s, 2H), 6.77 (q, 1H), 7.20 (q, 3H), 7.29 (m, 3H), 7.38 (m, 5H), 7.47 (t, 3H), 7.61 (s, 1H), 7.66 (q, 2H).

f) 1,3-Dihydro-7-hydroxy-4-[2-[6-(phenylethoxy)hexyl]aminoethyl]-2H-indol-2-one hydrochloride 10 The compound from step e) (0.18 g) was dissolved in dry ethanol (50 ml) containing 2 drops of conc. hydrochloric acid (sg. 1.18). The mixture was hydrogenated at atmospheric pressure using 5% Pd/C (0.020 g) as catalyst. After 4 hours the catalyst was removed by filtration and the solvent evaporated under reduced pressure, recrystallisation from ethanol gave the title salt as a white solid.

mp 277°–278° (decomposes);

Mass Spectrum: TSP 397 [(M+H)$^+$];

$^1$H NMR (D$_6$-DMSO) δ:1.28 (m, 4H), 1.49 (t, 2H), 1.59 (t, 2H), 2.72–2.82 (m, 4H), 2.88 (t, 2H), 3.02 (t, 2H), 3.36 (2H+H$_2$O), 3.48 (s, 2H), 3.56 (t, 2H), 6.66 (q, 2H), 7.21–7.28 (m, 5H), 8.75 (brs, 2H), 9.45 (s, 1H), 10.22 (s, 1H);

Analysis: Found; C,65.96; H,7.67; N,6.58%.

C$_{23}$H$_{32}$N$_2$O$_3$.HCl requires: C,66.51; H,7.68; N,6.47%.

EXAMPLE 5

4-Hydroxy-7-[2-[3-[2-(2-phenylethyl)aminoethyl]-sulphonylpropyl]aminoethyl]-1,3-benzothiazol-2(3H)-one dihydrochloride a) 3-[2-Oxo-2-(2-phenylethyl)amino]ethylthiopropanoic acid A solution of 3-mercaptopropanoic acid (1.63 ml) in dimethylformamide (5 ml) was added gradually to a stirred suspension of sodium hydride (2 eq.) in dimethylformamide at room temperature. The suspension was stirred for 2 hours then cooled to 0° before gradually adding a solution of chloro-N-(2-phenylethyl)acetamide (3.7 g) in dimethylformamide and allowing the mixture to warm to room temperature. After stirring overnight the solvent was removed under reduced pressure and the residue taken up in ethyl acetate. The organic layer was washed with dilute aqueous hydrochloric acid and brine. Drying and evaporation of the solvent under reduced pressure gave a yellow oil which was purified by column chromatography (SiO$_2$).

Mass Spectrum: 339 (mono-TMS derivative);

$^1$H NMR (CDCl$_3$) δ:2.57 (t, 2H), 2.69 (t, 2H), 2.85 (m, 2H), 3.22 (s, 2H), 3.53–3.58 (q, 2H), 7.14–7.34 (m, 6H).

b) N-[2-(2,4-Dimethoxy-1,3-benzothiazol-7-yl)ethyl]-3-[2-oxo-2-(2-phenylethylamino)ethylthio]propanamide Carbonyldiimidazole (3.04 g) was added to a solution of the compound from step a) (4.55 g) in dichloromethane (30 ml) and the mixture stirred at room temperature for 90 min, 2-(2,4-dimethoxy-1,3-benzothiazol-7-yl)-ethylamine (4.06 g) in dichloromethane was added and the mixture stirred overnight. Water was then added and the aqueous phase extracted with dichloromethane. The organic extracts were washed (dilute HCl, NaHCO$_3$ and brine), dried (MgSO$_4$) and the solvent removed under reduced pressure to yield the subtitled compound as an orange oil which was used without further purification.

Mass Spectrum: FAB 488 [(M+H)$^+$].

c) N-[2-(4-Methoxy-2-oxo-3H-1,3-benzothiazol-7-yl)-ethyl]-3-[2-oxo-2-(2-phenylethylamino) ethylthio]propanamide Conc. hydrochloric acid (sg. 1.18, 1.5 ml) was added to the compound from step b) (3.3 g) in methanol (30 ml) and the mixture stirred at room temperature overnight. The solvent was evaporated under reduced pressure and the residue partitioned between chloroform and water. The organic layer was separated and the aqueous layer extracted with dichloromethane. The combined organic extracts were dried (MgSO$_4$) and the solvents removed under reduced pressure to give the subtitled compound as an orange oil.

Mass Spectrum: FAB 474 [(M+H)$^+$];

$^1$H NMR (CDCl$_3$) δ:2.38–3.77 (m, 14H), 3.82–3.92 (m, 3H), 6.27 (brs, 1H), 6.74 (d, 1H), 6.93 (d, 1H), 7.1 (brs, 1H), 7.15–7.33 (m, 5H), 9.05 (s, 1H).

d) N-[2-(4-Methoxy-2-oxo-3H-1,3-benzothiazol-7-yl)ethyl]-3-[2-oxo-2-(2-phenylethylamino) ethylsulphonyl]propanamide Potassium peroxymonosulphate (5.57 g) was gradually added to a solution of the compound from step c) (2.81 g) in methanol:water (6:4, 72 ml) cooled to 0°. The mixture was stirred for 4 hours, water added and the whole extracted with chloroform. A yellow solid precipitated from the aqueous layer and was removed by filtration, and washed (water and pentane) to give the subtitled compound.

Mass Spectrum: FAB 506 [(M+H)$^+$];

$^1$H NMR (D$_6$-DMSO) δ:2.60–2.78 (2×t, 4H), 3.24–3.39 (m, 4H), 3.45–3.55 (m, 4H), 3.84 (s, 3H), 4.08 (s, 2H), 6.92 (d, 1H), 6.96 (d, 1H), 7.18–7.32 (m, 5H), 8.18 (brt, 1H), 8.44 (brt, 1H), 11.86 (s, 1H).

e) 4-Methoxy-7-[2-N-[3-[2-N'-(2-phenylethyl) aminoethyl]sulphonylpropyl]-aminoethyl]-1,3-benzothiazol-2(3H)-one dihydrochloride Prepared according to the method of Example 1b).
Mass Spectrum: FAB 478 [(M+H)$^+$].

f) 4-Hydroxy-7-[2-[3-[2-(2-phenylethyl)aminoethyl] sulphonylpropyl]aminoethyl]-1,3-benzothiazol-2 (3H)-one dihydrochloride The compound from step e) (0.33 g) was dissolved in 48% aqueous hydrobromic acid (10 ml) to which hypophosphorous acid (2 drops) had been added and the mixture heated to reflux under argon for 3 hours. The hydrobromic acid was removed under is reduced pressure and the residue purified by reverse phase HPLC, using methanol/0.1% aqueous trifluoroacetic acid as eluant, to give the title salt.

mp 241°–244°;

$^1$H NMR (D$_6$-DMSO) δ:2.03–2.15 (m, 2H), 2.86 (t, 2H), 2.96 (t, 2H), 3.02–3.18 (brm, 4H), 3.22 (t, 2H), 3.40–3.45 (m, 4H), 3.62 (t, 2H), 6.76 (d, 1H), 6.86 (d, 1H), 7.23–7.39 (m, 5H), 8.93 (brs, 2H), 9.16 (brs, 2H), 10.11 (s, 1H), 11.76 (s, 1H);

Analysis: Found; C,43.99; H,5.27; N,6.74; S,10.30%.

C$_{22}$H$_{29}$N$_3$O$_4$S$_2$.1.8HCl requires: C,43.88; H,5.49; N,6.98; S,10.64%.

EXAMPLE 6

(R,S)-4-Hydroxy-7-[2-[7-(2-phenylethoxy)-hept-2-yl]aminoethyl]-1,3-benzothiazol-2(3H)-one hydrochloride Sodium cyanoborohydride (0.056 g), 6-(2-phenylethoxy-oxy)-heptan-2-one (1.450 g) and 6% aqueous acetic acid (20 drops) were added to a solution of 7-(2-aminoethyl)-4-hydroxy-1,3-benzothiazol-2(3H)-one hydrochloride (0.300 g) in methanol (30 ml). The mixture was stirred for 4 days at room temperature until HPLC, using methanol/0.1% aqueous trifluoroacetate as eluant, revealed that all the starting material had been consumed. Aqueous ammonium hydroxide (2 drops) was added and the solvent removed under reduced pressure. Purification by chromatography (SiO$_2$) using ethanol/dichloromethane as eluant followed by reverse phase HPLC, using methanol/0.1% aqueous trifluoroacetate as eluant, and formation of the hydrochloride salt gave the title salt as a white solid.

mp 166°–168°;

Mass Spectrum: FAB 429 [(M+H)$^+$];

$^1$H NMR (D$_6$-DMSO) δ:1.20–1.40 (m, 5H), 1.20 (d, 3H), 1.40–1.60 (m, 2H), 1.70 (brm, 1H), 2.79 (t, 2H), 2.88 (m, 2H), 3.00–3.20 (brm, 3H), 3.37 (t, 2H), 3.55 (t, 2H), 6.76 (d, 1H), 6.89 (d, 1H), 7.15–7.30 (m, 5H), 8.81 (brs, 1H), 8.90 (brs, 1H), 10.14 (s, 1H), 11.77 (s, 1H);

Analysis: Found; C,61.45; H,7.67; N,6.17; S,7.06%.

C$_{24}$H$_{32}$N$_2$O$_3$S.HCl requires: C,61.99; H,7.15; N,6.02; S,6.89%.

EXAMPLE 7

The following compound was prepared by the method of Example 6:

(R,S)-4-Hydroxy-7-[2-[3-(4-methoxyphenyl)propyl] aminoethyl]-1,3-benzothiazol-2(3H)-one hydrochloride mp 210°;

Mass Spectrum: FAB 359 [(M+H)$^+$];

$^1$H NMR (D$_6$-DMSO) δ:1.10 (d, 3H), 2.58 (q, 1H), 2.68 (brm, 2H), 3.4–3.5 (4H+H$_2$O), 3.73 (s, 3H), 6.76 (d, 1H), 6.90 (d, 3H), 7.16 (d, 2H), 8.89 (brs, 2H), 10.13 (s, 1H), 11.77 (s, 1H);

Analysis: Found; C,53.79; H,5.55; N,6.16%.

C$_9$H$_{22}$N$_2$O$_3$S.2HCl requires: C,53.03; H,5.39; N,6.51%.

EXAMPLE 8

6-[2-[(4-Hydroxy-2-oxo-3H-1,3-benzothiazol-7-yl) ethyl]amino]-N-(2-phenylethyl)hexanamide hydrochloride a) 6-[N'-(2-Chloro-4-methoxy-1,3-benzothiazol-7-yl)ethyl]-N'-[(2,2,2-trifluoroacetyl)amino]-N-(2-phenylethyl)hexanamide Sodium hydride (80% in oil, 0.244 g) was added to a stirred solution of N-[2-(2-chloro-4-hydroxy-1,3-benzothiazol-7-yl)ethyl]trifluoroacetamide (2.5 g) at room temperature. After stirring for 10 min the reaction was heated to 65° for 90 min. The mixture was cooled and a solution of 6-bromo-N-(2-phenylethyl)hexanamide (2.42 g) in dimethylformamide added, the mixture was stirred for 16 hours then heated to 70° for 3.5 hours. The solvent was evaporated under reduced pressure and the residue partitioned between dilute aqueous HCl and ethyl acetate. The organic layer was washed with brine, dried (MgSO$_4$) and the solvent removed under reduced pressure. Chromatography (SiO$_2$) using ethyl acetate/dichloromethane as eluant gave the subtitled compound as a pale yellow oil.

Mass Spectrum: FAB 556 [(M+H)$^+$];

$^1$H NMR (CDCl$_3$) δ:1.20–1.70 (m, 6H), 2.05–2.18 (m, 2H), 2.81 (t, 2H), 2.87–3.07 (m, 2H), 3.20+3.39 (2×t, 2H), 3.49–3.56 (q, 2H), 3.59–3.66 (m, 2H), 4.01+4.02 (2×s, 3H), 5.45 (brs, 1H), 6.89 (t, 1H), 7.15–7.34 (m, 6H).

b) 6-[2-[(2,4-Dimethoxybenzothiazol-7-yl)ethyl]amino]-N-(2-phenylethyl)hexanamide The compound from step a) (1.73 g) in methanol was added to a solution of sodium methoxide in methanol (Na metal 0.17 g in methanol 40 ml). The mixture was heated under reflux for 4.5 hours, water (6 ml) was added and the mixture heated under reflux for a further 18 hours. The solvent was removed under reduced pressure, water added and the residue acidified with glacial acetic acid then made basic with ammonium hydroxide solution. The solution was extracted with chloroform, the organic layers dried (Na$_2$SO$_4$) and the solvent removed under reduced pressure. Chromatography (SiO$_2$) using methanol/dichloromethane as eluant gave the subtitled compound as a pale yellow solid.

mp 112°–113°;

Mass Spectrum: FAB 456 [(M+H)$^+$];

$^1$H NMR (CDCl$_3$) δ:1.23–1.33 (m, 2H), 1.40–1.65 (m, 2H), 2.11 (t, 2H), 2.61 (t, 2H), 2.84 (t, 2H), 2.85–3.00 (m, 6H), 3.50–3.57 (q, 2H), 3.99 (s, 3H), 4.24 (s, 3H), 5.45 (brs, 1H), 6.82 (d, 1H), 7.02 (d, 1H), 7.17–7.3 (m, 5H);

Analysis: Found; C,66.25; H,7.38; N,9.39; S,6.82%,

C$_{25}$H$_{33}$N$_3$O$_3$S requires: C,65.90; H,7.30; N,9.22; S,7.04%.

c) 6-[2-(4-Hydroxy-2-oxo-3H-1,3-benzothiazol-7-yl)ethylamino]-N-(2-phenylethyl)-hexanamide hydrochloride Boron tribromide (1M in dichloromethane, 15 ml) was added dropwise to a solution of the compound from step b) (0.53 g) in dichloromethane (30 ml). The mixture was stirred at room temperature for 48 hours and a further portion of boron tribromide solution (7 ml) added. Stirring was continued for 24 hours, methanol added to destroy any remaining boron tribromide and the solvent removed under reduced pressure. A portion of toluene was added and then removed under reduced pressure. The residue was purified by reverse phase HPLC using methanol/0.1% aqueous trifluoroacetic acid as eluant. Conversion to the hydrochloride salt gave the title salt as a white solid.

mp 206°–208°;

Mass Spectrum: FAB 428 [(M+H)$^+$];

$^1$H NMR (D$_6$-DMSO) δ:1.20–1.30 (m, 2H), 1.42–1.53 (q, 2H), 1.50–1.65 (q, 2H), 2.05 (t, 2H), 2.70 (t, 2H), 2.80–2.95 (m, 4H), 3.00–3.12 (brm, 2H), 3.22–3.31 (q, 2H), 6.77 (d, 1H), 6.87 (d, 1H), 7.15–7.30 (m, 5H), 7.92 (t, 1H), 8.87 (brs, 2H), 10.15 (brs, 1H), 11.77 (s, 1H);

Analysis: Found; C,54.71; H,6.08; N,8.22; S,5.88; Cl,12.34%,

C$_{23}$H$_{29}$N$_3$O$_3$S.2HCl requires: C,55.19; H,6.24; N,8.40; S,6.41; Cl, 14.16%.

EXAMPLE 9

4-Hydroxy-7-[2-[6-(2-phenylethylthio)hexyl]aminoethyl]-1,3-benzothiazol-2(3H)-one hydrochloride a) 6-(2-Phenylthio)hexanoic acid 7-[2-[6-(2-phenylethylthio)hexanamido]ethyl]-1,3-benzothiazol-2(3H)-one ester Triethylamine (1 ml) was added to a suspension of 7-(2-aminoethyl)-4-hydroxy-1,3-benzothiazol-2(3H)-one hydrobromide (2.07 g) in chloroform (30 ml). Triethylamine (2 ml) followed by ethyl chloroformate (1.33 ml) were added to a solution of 6-(2-phenylethylthio)hexanoic acid (3.35 g) in chloroform (30 ml) and the mixture stirred for 30 min. The two solutions were then mixed and stirred for 72 hours at room temperature. Water was added and the aqueous layer extracted with dichloromethane, the organic layers were washed with brine, dried (MgSO$_4$) and the solvent removed under reduced pressure. Chromatography (SiO$_2$) using methanol/dichloromethane as eluant gave the subtitled compound as a white solid.

mp 178°–178.5°;

Mass Spectrum: FAB 679 [(M+H)$^+$];

$^1$H NMR (CDCl$_3$) δ:1.23–1.29 (m, 2H), 1.42–1.68 (m, 10H), 1.99–2.04 (t, 2H), 2.45–2.84 (m, 16H), 3.27–3.33 (m, 2H), 6.99 (s, 2H), 7.18–7.30 (m, 10H), 7.90–7.93 (t, 1H), 12.16 (s, 1H);

Analysis: Found; C,65.65; H,7.02; N,4.17; S,13.71%,

C$_{37}$H$_{46}$N$_2$O$_4$S, requires: C,65.48; H,6.78; N,4.12; S,14.15%.

b) 4-Hydroxy-7-[2-[6-(2-phenylethylthio)hexyl]aminoethyl]-1,3-benzothiazol-2(3H)-one hydrochloride Prepared by the method of Example 1b) using the compound from step a).

mp 226.5°–227.5°;

$^1$H NMR (D$_6$-DMSO) δ:1.25–1.4 (m, 4H), 1.45–1.65 (m, 4H), 2.7–2.95 (m, 8H), 3.0–3.1 (m, 2H), 3.34 (brs, 2H), 6.75+6.88 (2×d, 2H), 7.17–7.30 (m, 5H), 8.84 (brs, 2H), 10.14 (s, 1H), 11.77 (s, $^1$H);

Analysis: Found; C,59.46; H,6.85; N,6.08; S,13.35%,

C$_{23}$H$_{30}$N$_2$O$_2$S$_2$.HCl requires: C,59.14; H,6.69; N,6.00; S,13.73%.

EXAMPLE 10

N-[2-Hydroxy-5-[2-N'-[6-(2-phenylethoxy)hexyl]aminoethyl]phenyl]formamide oxalate salt a) N-[2-(3-Nitro-4-phenylmethoxyphenyl)ethyl]trifluoroacetamide Benzyl bromide (7.86 g) was added to a stirred solution of N-[2-(3-nitro-4-phenol)ethyl]trifluoroacetamide (11.66 g) and anhydrous potassium carbonate (6.3 g) in dimethylformamide (100 ml), cooled in an ice bath. Stirring was continued for 5 hours and the mixture poured into ice/water. The solid produced was dissolved in ethyl acetate and the aqueous phase extracted with ethyl acetate. The organic extracts were washed with brine, dried and the solvent removed under reduced pressure. The residue was purified by column chromatography to give the subtitled compound as a white crystalline solid.

mp 85°–86°;

Mass Spectrum: RbI 453/5 [(M+Rb)$^+$];

$^1$H NMR (CDCl$_3$) δ:2.87 (t, 2H), 3.58 (m, 2H), 5.20 (s, 2H), 6.56 (br, 1H), 7.07 (d, 1H), 7.3–7.5 (m, 6H), 7.69 (d, 1H);

Analysis: Found; C,55.95; H,4.28; N,7.63; F,15.98%,

C$_{17}$H$_{15}$F$_3$N$_2$O$_4$ requires: C,55.43; H,4.10; N,7.65; F,15.47%.

b) 3-Nitro-4-(phenylmethoxy)benzeneethanamine hydrochloride

The compound from step a) (9.8 g), and anhydrous potassium carbonate (4.03 g) in water (10 ml) and ethanol (100 ml) were heated to reflux for 2 hours. The ethanol was evaporated under reduced pressure, water was added and the mixture extracted with ethyl acetate. The organic extracts were dried and the solvent removed under reduced pressure and the residue converted to the hydrochloride salt.

mp 190°–193°;

Mass Spectrum: FAB 272 [(M+H)⁺];

¹H NMR (D₆-DMSO) δ:2.92 (t, 2H), 3.04 (t, 2H), 5.30 (s, 2H), 7.3–7.5 (m, 6H), 7.57 (dd, 1H), 7.83 (d, 1H), 8.15 (brs, 3H);

Analysis: Found; C,56.68; H,5.43; N,8.84; Cl,11.14%,

C₁₅H₁₆N₂O₃.HCl requires: C,56.68; H,5.72; N,8.79; Cl,11.13%.

c) N-2-[3-Nitro(4-phenylmethoxy)phenyl]ethyl-6-(2-phenylethoxy)hexanamide

Carbonyldiimidazole (0.33 g) was added to a solution of 6-(2-phenylethoxy)hexanoic acid (0.47 g) in dichloromethane, the mixture was stirred at room temperature for 1 hour. A solution of the compound from step b) (0.54 g) was then added and the mixture stirred for 1 hour. Water was added and the organic layer separated and washed with dilute HCl and brine, dried (MgSO₄) and the solvent removed under reduced pressure. The residue was purified by column chromatography.

Mass Spectrum: FAB 491 [(M+H)⁺];

¹H NMR (CDCl₃) δ:1.33 (m, 2H), 1.59 (m, 4H), 2.1 (t, 2H), 2.82/2.86 (t, 2×2H), 3.41–3.61 (m, 3×2H), 5.21 (s, 2H), 7.04 (d, 1H), 7.15–7.6 (m, 11H), 7.66 (d, 1H).

d) 3-Nitro-4-phenylmethoxy-N-[6-(2-phenylethoxy)hexyl]benzeneethanamine hydrochloride Prepared by the method of Example 1b) using the compound from step c).

mp 142°–143°;

Mass Spectrum: FAB 477 [(M+H)⁺];

¹H NMR (D₆-DMSO) δ:1.45 (brm, 4H), 1.47 (brt, 2H), 1.60 (brt, 2H), 2.80 (t, 2H), 2.85 (brm, 2H), 3.00 (m, 2H), 3.12 (brm, 2H), 3.37 (t, 2H), 3.55 (t, 2H), 5.30 (s, 2H), 7.15–7.45 (m, 11H), 7.57 (dd, 1H), 7.84 (d, 1H), 8.97 (brs, 2H);

Analysis: Found; C,67.52; H,7.44; N,5.71; Cl,6.90%,

C₂₉H₃₆N₂O₄.HCl requires: C,67.88; H,7.27; N,5.46; Cl,6.91%.

e) 3-Nitro-N-[6-(2-phenylethoxy)hexyl]-4-(phenylmethoxy)-N-(phenylmethoxy-carbonyl)benzeneethanamine Triethylamine (0.165 g) was added to a stirred suspension of the compound from step d) (0.25 g) in dichloromethane (20 ml) cooled in ice. Benzylchloroformate (0.1 g) was added and the mixture allowed to warm to room temperature. The mixture was stirred until TLC indicated the reaction was complete then a further equivalent of benzylchloroformate was added and the mixture stirred for 2 hours. Water was added, the organic layer was separated, dried and the solvent removed under reduced pressure to give the subtitled compound as a yellow oil which was used without further purification.

Mass Spectrum: TSP with NH₄⁺ 628 [(M+NH₄)⁺];

¹H NMR (CDCl₃) δ:1.28–1.52 (m, 6H), 2.8–2.89 (m, 6H), 3.17 (m, 2H), 3.41 (m, 4H), 3.60 (t, 2H), 4.59 (s, 2H), 5.07–5.20 (m, 2H), 7.20–7.60 (m, 18H).

f) 3-Amino-4-(phenylmethoxy)-N-[6-(2-phenylethoxy)hexyl]-N-(phenylmethoxy-carbonyl)benzeneethanamine Prepared by the method of Example 4b), and the resulting oil purified by column chromatography (SiO₂) using diethyl ether:petrol (1:1) as eluant.

Mass Spectrum: FAB 581 [(M+H)⁺];

¹H NMR (CDCl₃) δ:1.25 (m, 4H), 1.51 (m, 4H), 2.70 (m, 2H), 2.87 (t, 2H), 3.17 (m, 2H), 3.40 (m, 4H), 3.60 (t, 2H), 5.04 (m, 2H), 5.12 (m, 2H), 6.4–6.8 (m, 3H), 7.15–7.50 (m, 15H).

g) N-5-[2-N'-[6-(2-Phenylethoxy)hexyl]aminoethyl]-N'-[(phenylmethoxycarbonyl)-2-(phenylmethoxy)phenyl]formamide The compound from step f) (0.58 g) was heated under reflux for 21 hours in neat ethylformate. The reaction was evaporated to dryness and the residual oil purified by column chromatography using ethyl acetate:petrol (1:3) as eluant.

Mass Spectrum: FAB 609 [(M+H)⁺];

¹H NMR (CDCl₃) δ:1.25 (m, 4H), 1.51 (m, 4H), 2.78 (m, 2H), 2.87 (t, 2H), 3.2–3.4 (m, 6H), 3.6 (t, 2H), 5.06 (s, 2H), 5.12 (d, 2H), 6.85 (m, 2H), 7.15–7.45 (m, 16H), 7.6–7.75 (brs, 1H), 8.26–8.38 (d, 1H).

h) N-[2-Hydroxy-5-[2-N'-[6-(2-phenylethoxy)hexyl]aminoethyl]phenyl]formamide oxalate salt A mixture of the compound from step g) (0.3 g), ammonium formate (0.3 g) and 10% Pd/C (0.3 g) in methanol (30 ml) was heated at reflux for 30 min. The mixture was filtered (Hyflo Supergel) and the solvent evaporated under reduced pressure. The resulting solid was purified by column chromatography (SiO₂) using dichloromethane:methanol (4:1) as eluant. The free base of the title compound was then converted to the oxalate salt.

mp 207°–209°;

Mass Spectrum: FAB 385 [(M+H)⁺];

¹H NMR (D₆-DMSO) δ:1.28 (m, 4H), 1.47 (m, 2H), 1.55 (m, 2H), 2.79 (m, 4H), 2.85 (m, 2H), 3.00 (m, 2H), 3.37–3.55 (m, 4H+H₂O), 6.82 (m, 2H), 7.23 (m, 6H), 7.99 (br, 1H), 8.27 (br, 1H), 8.6 (brs, 2H), 9.6 (brs, 1H);

Analysis: Found; C,57.94; H,6.93; N,6.02%,

C₂₃H₃₂N₂O₃.C₂H₂O₄ (0.9M oxalate) requires: C,57.94; H,6.45; N,6.04%.

EXAMPLE 11

7-[2-[6-[2-(4-Aminophenyl)ethoxy]hexyl]aminoethyl]-4-hydroxy-1,3-benzothiazol-2(3H)-one dihydrochloride a) N-[2-(4-Hydroxy-2-oxo-3H-1,3-benzothiazol-7-yl)ethyl]-6-[2-(4-nitrophenyl)-ethoxy]hexanamide Prepared by the method of Example 1a), using 6-[2-(4-nitrophenyl)ethyl]hexanoic lo acid and 7-(2-aminoethyl)-4-hydroxy-1,3-benzothiazol-2(3H)-one hydrobromide.

Mass Spectrum: FAB 474 [(M+H)⁺];

¹H NMR (D₆-DMSO) δ:1.2 (m, 2H), 1.45 (m, 4H), 2.0 (t, 2H), 2.55 (t, 2H), 2.95 (t, 2H), 3.25 (m, 2H), 3.35 (t, 2H), 3.62 (t, 2H), 6.70 (d, 1H), 6.79 (d, 1H), 7.50–8.15 (m, 4H);

Analysis: Found; C,58.18; H,5.99; N,9.01; S,6.57%,

C₂₃H₂₇N₃O₆S requires: C,58.33; H,5.75; N,8.87; S,6.77%.

b) 6-[2-(4-Aminophenyl)ethoxy]-N-[2-(4-hydroxy-2-oxo-3H-1,3-benzothiazol-7-yl)-ethyl]hexanamide The compound of step a) (0.5 g), hydrazine hydrate (5 ml) and 10% Pd/C (0.05 g) in ethanol (50 ml) were heated at reflux for 2 hours. The mixture was filtered (Hyflo Supergel), the solvent removed under reduced pressure and the residue purified by chromatography using dichloromethane:methanol (9:1) as eluant.

Mass Spectrum: FAB 444 [(M+H)$^+$];

$^1$H NMR (D$_6$-DMSO) δ:1.2 (m, 2H), 1.45 (m, 4H), 2.0 (t, 2H), 2.6 (m, 4H), 3.25 (m, 2H), 3.3–3.45 (t, 2×2H), 4.82 (brs, 2H), 6.45–6.85 (dd, 4H), 6.7–6.8 (dd, 2H), 7.84 (t, 1H), 9.89 (brs, 1H), 11.6 (brs, 1H);

Analysis: Found; C,62.45; H,6.70; N,9.64; S,6.76%.

C$_{23}$H$_{29}$N$_3$O$_4$S requires: C,62.28; H,6.59; N,9.47; S,7.22%.

c) 7-[2-[6-[2-(4-Aminophenyl)ethoxy]hexyl]aminoethyl]-4-hydroxy-1,3-benzothiazol-2(3H)-one dihydrochloride Prepared by the method of Example 1b), using the compound from step b).

mp 154°–157°;

Mass Spectrum: FAB 430 [(M+H)$^+$];

$^1$H NMR (D$_6$-DMSO) δ:1.25 (m, 4H), 1.45 (m, 2H), 1.58 (m, 2H), 2.6–2.9 (m, 6H), 3.05 (m, 2H), 3.35 (t, 2H), 3.55 (t, 2H), 6.78–6.88 (dd, 2H), 7.3 (m, 4H), 9.05 (brs, 2H), 10.15 (s, 1H), 10.3 (br, 1H), 11.8 (brs, 1H);

Analysis: Found; C,53.80; H,6.64; N,8.22; Cl,13.77; S,5.82%.

CH$_{23}$H$_{31}$N$_3$O$_3$S.2HCl (0.83M H$_2$O) requires: C,53.38; H,6.75; N,8.12; Cl,13.70; S,6.19%.

EXAMPLE 12

4-Hydroxy-7-[2-[6-[2-(2-pyridyl)ethoxy]hexyl]aminoethyl]-1,3-benzothiazol-2(3H)-one oxalate salt A mixture of 4-hydroxy-7-(2-aminoethyl)-1,3-benzothiazol-2(3H)-one (0.945 g), 2-(6-bromohexyloxyethyl)pyridine (0.863 g) and diisopropylethylamine (0.66 ml) in dry dimethylformamide (25 ml) was heated at 100° for 2.5 hours. The solvent was removed under reduced pressure and the residue purified by column chromatography (SiO$_2$) using dichloromethane:methanol (9:1) as eluant. The resulting free base was then converted is to the title oxalate salt.

mp 182°–183° (decomposes);

Mass Spectrum: FAB 416 [(M+H)$^+$];

$^1$H NMR (D$_6$-DMSO) δ:1.25 (m, 4H), 1.50 (m, 4H), 2.85 (m, 6H), 3.1 (m, 2H), 3.38 (m, 2H), 3.65 (m, 2H), 6.75–6.85 (dd, 2H), 7.2 (dd, 1H), 7.35 (d, 1H), 7.70 (m, 1H), 8.45 (d, 1H), 8.70 (brs, 1H), 11.75 (brs, 1H);

Analysis: Found; C,53.70; H,5.98; N,7.60; S,5.56%.

C$_{22}$H$_{29}$N$_3$O$_3$S.(0.5M H$_2$O, 0.5M excess oxalic acid) requires: C,53.54; H,5.88; N,7.48; S,5.70%.

EXAMPLE 13

7,7'-[1,6-Hexanediylbis(imino-2,1-ethanediyl)]bis[4-hydroxy-1,3-benzothiazol-2(3H)-one]difluoroacetate a) Bis-N,N'-[(2,4-dimethoxy-1,3-benzothiazol-7-yl)ethyl]hexan-1,6-diamide

Adipoyl chloride (1.15 g) in dichloromethane was added dropwise over 30 min to a stirred solution of 2-(2,4-dimethoxy-1,3-benzothiazol-7-yl)ethanamine (3.0 g, *J. Med. Chem.*, 1987, 30, 1166) and triethylamine (3.5 ml) in dichloromethane (150 ml). The mixture was stirred at room temperature for 60 hours, filtered and the filtrate washed with dilute HCl, aqueous sodium bicarbonate and brine. The solvent was removed under reduced pressure and the residue stirred with dilute HCl. The solid was filtered, dissolved in chloroform, washed with brine, dried (MgSO$_4$) and the solvent removed under reduced pressure. Purification by chromatography (SiO$_2$) gave the subtitled compound which was used without further purification in the next step.

Mass Spectrum: FAB 587 [(M+H)$^+$].

b) N,N'-[2-(2,4-Dimethoxy-1,3-benzothiazol-7-yl)ethyl]-hexan-1,6-diamine dihydrochloride Prepared by the method of Example 1b) using the compound from step a).

Mass Spectrum: FAB 559 [(M+H)$^+$].

c) 7,7'-[1,6-Hexanediylbis(imino-2,1-ethanediyl)bis[4-hydroxy-1,3-benzothiazol-2(3H)-one] difluoroacetate The compound from step b) was dissolved in aqueous hydrobromic acid (48%) to which several drops of hypophosphorous acid had been added. The solution was refluxed for 3 hours. The solvent was removed under reduced pressure and the residue purified by preparative reverse phase HPLC to give the title salt.

mp 231°–233°;

Mass Spectrum: FAB 517 [(M+H)$^+$];

$^1$H NMR (D$_6$-DMSO) δ:1.32 (brs, 4H), 1.58 (brs, 4H), 2.83 (brt, 4H), 2.93 (bt, 4H), 3.10 (brt, 4H), 6.74–6.90 (m, 4H), 8.56 (brs, 2H), 10.16 (s, 2H), 11.76 (brs, 2H);

Analysis: Found; C,43.11; H,4.28; N,6.78; S,8.66%.

C$_{24}$H$_{30}$N$_4$O$_4$S$_2$ requires: C,43.11; H,3.97; N,6.77; S,7.75%.

EXAMPLE 14

7-[2-[1,1-Dimethyl-6-(2-phenylethoxy)hexyl]aminoethyl]-4-hydroxy-1,3-benzothiazol-2(3H)-one hydrochloride a) 1,1-Dimethyl-6-(2-phenylethoxy)hexanamide hydrochloride

Diphenylphosphoryl azide (6.81 g) was added to a stirred solution of 2,2-dimethyl-6-(2-phenylethoxy)hexanoic acid (6.13 g) and triethylamine (2.5 g) in toluene (100 ml) and the reaction stirred at 80° for 3 hours. The organic layer was washed with water and evaporated under reduced pressure to give a yellow oil. The residue was taken up in dioxan (100 ml), diluted with water (50 ml), and acidified to pH 1 with conc. hydrochloric acid. The solution was heated on a steam bath for 3 hours, heated under reflux for 30 min and the solvent evaporated under reduced pressure. The residue was dried by azeotropic distillation with 2-propanol and recrystallised from petroleum ether 60°–80°:ethyl acetate.

mp 111°–112°;

Mass Spectrum: FAB 250 [(M+H)$^+$];

$^1$H NMR (CDCl$_3$) δ:1.37–1.40 (brm, 4H), 1.40 (s, 6H), 1.54–1.61 (quin, 2H), 1.67–1.69 (brm, 2H), 2.85–2.89 (t, 2H), 3.39–3.42 (t, 2H), 3.58–3.62 (t, 2H), 7.17–7.30 (m, 5H), 8.33 (brs, 3H);

Analysis: Found; C,67.20; H,9.86; N,5.13; Cl,12.79%.

$C_{16}H_{27}NO.HCl$ requires: C,67.22; H,9.87; N,4.90; Cl,12.40%.

b) (2,4-Dimethoxy-1,3-benzothiazol-7-yl)acetic acid

A solution of (2,4-dimethoxy-1,3-benzothiazol-7-yl)-acetonitrile (3.61 g, *J. Med. Chem.*, 1987, 30, 1166) and potassium hydroxide (3.45 g) in methanol:water (2:1, 150 ml) was heated to reflux for 6.5 hours. The reaction was cooled and the solvents evaporated under reduced pressure. Water (50 ml) was added and the aqueous layer extracted with diethyl ether. The aqueous layer was then acidified to $pH_{4/5}$ with acetic acid and extracted with ethyl acetate. The combined organic layers were washed (water and brine), dried ($MgSO_4$) and the solvent evaporated under reduced pressure to yield the subtitled compound which was used in the next step without further purification.

c) (4-Hydroxy-2(3H)-oxo-1,3-benzothiazol-7-yl) acetic acid

Prepared by the method of Example 14c) using the compound from step b).

mp 170°–175°;

Mass Spectrum:225 [(M+H)$^+$];

$^1$H NMR (d$_6$-DMSO) δ:3.47 (s, 2H), 6.71 (d, 1H), 6.86 (d, 1H), 10.02 (brs, 1H), 11.68 (brs, 1H), 12.44 (brs, 1H);

Analysis: Found; C,48.07; H,3.23; N,6.13; S,13.90%.

$C_9H_7NO_4S$ requires: C,47.99; H,3.13; N,6.22; S,14.20%.

d) 2-(4-Hydroxy-2-oxo-3H-1,3-benzothiazol-7-yl)-N-[1,1-dimethyl]-[6-(2-phenylethoxy)]hexyl] acetamide Prepared by the method of Example 1a) using the compounds from steps a) and c).

Mass Spectrum: TSP 457 [(M+H)$^+$];

$^1$H NMR (CDCl$_3$) δ:1.20–1.80 (m, 8H), 1.38 (s, 6H), 2.90 (s, 2H), 3.42 (s, 2H), 3.46 (t, 2H), 3.66 (t, 2H), 5.70 (s, 1H), 6.40 (d, 1H), 6.70 (d, 1H), 7.20–7.30 (m, 5H), 8.77 (s, 1H).

e) 7-[2-[1,1-Dimethyl-6-(2-phenylethoxy)hexyl]aminoethyl]-4-hydroxy-1,3-benzothiazol-2(3H)-one hydrochloride Prepared by the method of Example 1b) using the compound from step d).

mp 183°–185°;

Mass Spectrum: FAB 443 [(M+H)$^+$];

$^1$H NMR (D$_6$-DMSO) δ:1.25 (brs, 10H), 1.45–1.60 (m, 4H), 2.79 (t, 2H), 2.90 (m, 2H), 3.00 (brs, 2H), 3.40 (m, 2H+H$_2$O), 3.56 (t, 2H), 6.76–6.92 (d, 2H), 7.2–7.3 (m, 5H), 8.79 (s, 2H), 10.13 (s, 1H), 11.77 (s, 1H);

Analysis: Found; C,61.09; H,7.84; N,5.70; S,5.69%.

$C_{25}H_{34}N_2O_3S.HCl$ (12% ethanol) requires: C,61.40; H,7.87; N,5.11; S,5.89%.

EXAMPLE 15

4-Hydroxy-7-[2-[6-[2,2-difluoro-2-phenethylamino] hexylamino]ethyl]-1,3-benzothiazol-2(3H)-one dihydrochloride a) 5-[2,2-Difluoro-2-phenyl] ethylaminocarbonylpentanoic acid, methyl ester Triethylamine (0.791 ml), 1-hydroxybenzotriazole hydrate (0.767 g) and finally dicyclohexylcarbodiimide (1.17 g) were added to a stirred solution of 2,2-difluorophenethylamine (1.0 g, *J. Org. Chem.*, 1980, 45, 5333) and mono-methyl adipate (0.91 g) in DMF (30 ml). The whole was stirred for 16 hours at room temperature. The DMF was removed under reduced pressure and the residue slurried with ethyl acetate. The suspended dicyclohexylurea was removed by filtration. The filtrate was washed with 10% aqueous HCl, saturated aqueous sodium bicarbonate and dried ($MgSO_4$). The solvent was removed under reduced pressure to yield a residue which was purified by column chromatography over silica gel to give the subtitled compound (1.3 g, 84%).

mp 60°–62°;

Mass Spectrum: EI 299 (M$^+$);

$^1$H NMR (CDCl$_3$) δ:1.56–1.60 (m, 4H), 2.22 (t, 2H), 2.31 (t, 2H), 3.67 (s, 3H), 3.93 (dt, 2H), 5.28 (brs, 1H), 7.42–7.56 (m, 5H).

b) 5-[2,2-Difluoro-2-phenyl] ethylaminocarbonylpentanoic acid

Lithium (0.158 g) was dissolved in methanol (7 ml) under argon. H$_2$O (21 ml) was 30 added and the mixture cooled to 0°. The product from step a) (1.35 g) was then added. The mixture was stirred for 24 hours at 0°. After acidification the aqueous layer was extracted with ethyl acetate. The combined organic extracts were washed with water and brine then dried ($MgSO_4$). The mixture was filtered and the solvent removed under reduced pressure to yield a pale yellow solid (1.3 g) which was used directly in step c).

Mass Spectrum: TMS derivative 357 (M)$^+$;

$^1$H NMR (CDCl$_3$) δ:1.35–1.46 (m, 4H), 2.08 (t, 2H), 2.16 (t, 2H), 3.82 (dt, 2H), 7.49 (m, 5H), 8.25 (t, 1H), 11.98 (brs, 1H).

c) N-[2,2-Difluoro-2-phenylethyl]-N'-[2-[4-hydroxy-2-oxo-3H-1,3-benzothiazol-7-yl]ethyl] hexanediamide The subtitled compound was prepared by the method outlined in step a) using the material from step b) and 7-[2-aminoethyl]-4-hydroxy-1,3-benzothiazol-2(3H)-one hydrobromide.

mp 187°–188°;

Mass spectrum: FAB (+ve) 478 [(M+H)$^+$];

$^1$H NMR (D$_6$-DMSO) δ:1.37 (brs, 4H), 1.99 (brs, 2H), 2.07 (brs, 2H), 2.59 (t, 2H), 3.23 (q, 2H), 3.82 (dt, 2H), 6.70 (d, 1H), 6.79 (d, 1H), 7.47–7.52 (m, 5H), 7.85 (t, 1H), 8.2 (t, 1H), 9.90 (s, 1H), 11.62 (s, 1H);

Analysis: Found; C,56.46; H,5.55; N,8.50; S,5.98%.

$C_{23}H_{25}F_2N_3O_4S$ requires: C,57.85; H,5.26; N,8.80; S,6.71%.

d) 4-Hydroxy-7-[2-[6-[2,2-difluoro-2-phenylethylanino]hexylamino]ethyl]-1,3-benzothiazol-2(3H)-one dihydrochloride Borane-tetrahydrofuran solution (1.0M in THF, 7.2 ml) was added dropwise to a stirred solution of the product from step c) (0.70 g) in dry tetrahydrofuran. The reaction was refluxed under an inert atmosphere for 3 hours at which point thin layer chromatography indicated no more starting material remained. The reaction was cooled and methanol (5 ml) was added cautiously. The solvents were removed under reduced pressure and the residue dissolved in methanol (50 ml) to which concentrated hydrochloric acid (sg. 1.18, 2 ml) was added. This solution was refluxed for 15 min. The mixture was cooled and the methanol removed under reduced pressure to yield an off-white solid. Portions of the title compound were purified by preparative reverse phase HPLC using methanol and 0.1% aqueous trifluoroacetic acid as eluant. Finally preparation of the dihydrochloride salt gave the title salt as a white powder (0.34 g).

mp 236°–238°;

Mass Spectrum: FAB (+ve) 450 [(M+H)$^+$];

$^1$H NMR (D$_6$-DMSO) δ:1.33 (brs, 4H), 1.59–1.68 (m, 2H), 1.68–1.79 (m, 2H), 2.86–2.96 (m, 4H), 2.94–3.11 (m, 4H), 3.85–4.15 (m, 2H+H$_2$O), 6.79 (d, 1H), 6.89 (d, 1H), 7.56–7.68 (m, 5H), 9.13 (brs, 2H), 9.60 (brs, 2H), 10.20 (brs, 1H), 11.82 (s, 1H);

Analysis: Found; C,51.26; H,5.71; N,7.61; S,5.41; Cl,13.19%.

C$_{23}$H$_{29}$F$_2$N$_3$O$_2$.2HCl requires: C,52.87; H,5.98; N,8.04; S,6.14; Cl,13.57%.

EXAMPLE 16

7-[2-[2,2-Difluoro-6-[2-phenylethoxy]hexylamino]ethyl]-4-hydroxy-1,3-benzothiazol-2(3H)-one hydrochloride a) 4-[2-Phenylethoxy]butene

To a solution of 4-[2-phenylethoxy]butanol (3.16 g) and 2-nitrophenyl selenocyanate (4.0 g) in THF (50 ml) under argon was added tributylphosphine (4.5 ml) in THF (2 ml) dropwise over 30 min. After a further 2 hours at room temperature the solvent was removed under reduced pressure. A further 50 ml of THF was added and the mixture cooled to 0° at which point H$_2$O$_2$ (17 ml, 30% aqueous v/v) was added to the stirred solution over 1 hour. The mixture was allowed to warm to room temperature and stirring continued overnight. The solvent was removed under reduced pressure and the residue taken up in ether, washed with 1 molar aqueous hydrochloric acid, sodium bicarbonate solution and brine. The solution was dried, filtered and the solvent removed under reduced pressure to yield a yellow oil which was purified by chromatography using diethyl ether in petroleum ether (bp 60°–80°) as eluant to yield the subtitled compound (2.63 g, 92%).

Mass Spectrum: EI 176 (M$^+$);

$^1$H NMR (CDCl$_3$) δ:2.31–2.37 (m, 2H), 2.89 (t, 2H), 3.50 (t, 2H), 3.64 (t, 2H), 5.02–5.11 (m, 2H), 5.76–5.87 (m, 1H), 7.19–7.43 (m, 5H).

b) 2,2-Difluoro-6-[2-phenylethoxy]hexanoic acid, ethyl ester

The subtitled compound was prepared according to the procedure outlined in *J. Chem. Soc. Chem. Comm.*, 1992, 233 using the compound from step a) (0.422 g), ethyl difluoroiodoacetate (0.3 g), zinc (0.157 g) and NiCl$_2$.6H$_2$O (0.029 g) to yield the sub-titled compound (0.16 g, 22%).

Mass Spectrum: EI 300 (M$^+$);

$^1$H NMR (CDCl$_3$) δ:1.33 (t, 3H), 1.50–1.65 (m, 4H), 2.00–2.14 (m, 2H), 2.87 (t, 2H), 3.44 (t, 2H), 3.62 (t, 2H), 4.32 (q, 2H), 7.19–7.31 (m, 5H).

c) 2,2-Difluoro-6-[2-phenylethoxy]hexanoic acid

The product from step b) was hydrolysed according to the method outlined in Example 15b), to yield the subtitled compound as a yellow oil (0.18 g) which was used without further purification.

Mass Spectrum: EI TMS derivative 344 (M$^+$);

$^1$H NMR (CDCl$_3$) δ:1.52–1.66 (m, 4H), 2.02–2.16 (m, 2H), 2.89 (t, 2H), 3.51 (t, 2H), 3.68 (t, 2H), 7.19 –7.31 (m, 5H).

d) 2,2-Difluoro-N-[2-[4-hydroxy-2-oxo-3H-1,3-benzothiazol-7-yl]ethyl]-6-[2-phenylethoxy]hexanamide The subtitled compound was prepared by the method outlined in Example 15a) using the material from step c) and 7-[2-aminoethyl]-4-hydroxy-1,3-benzothiazol-2(3H)-one hydrobromide.

mp 167°–172°;

Mass Spectrum: FAB (+ve) 465 [(M+H)$^+$];

$^1$H NMR (D$_6$-DMSO) δ:1.25–1.29 (m, 2H), 1.43–1.49. (m, 2H), 1.88–2.04 (m, 2H), 2.65 (t, 2H), 2.77 (t, 2H), 3.30–3.40 (m, 4H+H$_2$O), 3.54 (t, 2H), 6.68 (d, 1H), 6.77 (d, 1H), 7.14–7.27 (m, 5H), 8.76 (t, 1H), 9.93 (s, 1H), 11.64 (s, 1H).

e) 7-[2-[2,2-Difluoro-6-[2-phenylethoxy]hexylamino]ethyl]-4-hydroxy-1,3-benzothiazol-2(3H)-one hydrochloride The title salt was prepared using the method outlined in Example 15d).

mp 23°0–232°;

Mass Spectrum: FAB (+ve) 451 [(M+H)$^+$];

$^1$H NMR (D$_6$-DMSO) δ:1.46–1.56 (m, 4H), 1.95–2.08 (m, 2H), 2.80 (t, 2H), 2.91–2.97 (m, 2H), 3.11–3.19 (brm, 2H), 3.41 (t, 2H+H$_2$O), 3.55–3.62 (m, 4H), 6.78 (d, 1H), 6.84 (d, 1H), 7.19–7.30 (m, 5H), 9.48 (brs, 2H), 10.19 (1H, s), 11.79 (s, 1H);

Analysis: Found; C,56.31; H,5.86; N,5.84; S,6.43; Cl,7.59%.

C$_{23}$H$_{28}$F$_2$N$_2$O$_4$S.HCl requires: C,56.72; H,6.00; N,5.75; S,6.58; Cl,7.28%.

EXAMPLE 17

7-[2-[3,3-Difluoro-6-[2-phenylethoxy]hexylamino]ethyl]-4-hydroxy-1,3-benzothiazol-2(3H)-one hydrochloride a) [2,4-Dimethoxy-1,3-benzothiazol-7-yl]acetic acid

A solution of [2,4-dimethoxy-1,3-benzothiazol-7-yl]acetonitrile (3.61 g, *J. Med. Chem.*, 1987, 30, 1166) and potassium hydroxide (3.45 g) in methanol:water (2:1, 150 ml) was refluxed for 6½ hours. The reaction was cooled and the solvents evaporated under reduced pressure. Water (50 ml) was added and the aqueous layer extracted with diethyl ether (the ethereal layer was discarded). The aqueous layer was acidified with acetic acid to pH 4/5 and this was extracted several times with ethyl acetate. These combined organic extracts were washed with water and brine, dried (MgSO$_4$) and the solvent evaporated under reduced pressure to yield the crude subtitled compound, (2.978 g) which was used in step b) without further purification.

b) 4-Hydroxy-2-oxo-3H-1,3-benzothiazole-7-acetic acid

The material from step a) (2.978 g) was dissolved in concentrated hydrobromic acid (48% aqueous, 60 ml) to which hypophosphorous acid was added (2 drops). The whole was refluxed and the course of the reaction followed by reverse phase HPLC. After 2 hours hydrobromic acid (10 ml) was added and refluxing was continued for 4½ hours. The reaction was allowed to cool and the precipitate was filtered off and washed with small portions of cold water and cold i-PrOH. This yielded the subtitled compound as a greyish solid (2.67 g, 77%). A sample was purified by reverse phase HPLC chromatography.

mp 170°–175°;

$^1$H NMR (D$_6$-DMSO) δ:3.47 (s, 2H), 6.69 (d, 1H), 6.86 (d, 1H), 10.00 (brs, 1H), 11.66 (s, 1H).

c) 1,3-Dihydro-2-[3-oxo-6-[2-phenylethoxy]hexyl]-2H-isoindal-1,3-dione

Sodium methoxide (0.01 g) was added to a stirred solution of 6-[2-phenylethoxy]-1-hexen-3-one (prepared by the oxidation of the alcohol formed by reaction between 4-[2-phenylethoxy]butanal and vinyl magnesium bromide, 1.0 g) and phthalimide (0.674 g) in DMSO (15 ml) at room temperature under argon. The mixture was stirred overnight, diluted with water and extracted with ether. The combined organic extracts were washed with water and brine and dried (MgSO$_4$). After filtration the solvent was removed under reduced pressure and the residual oil further purified by flash chromatography using diethyl ether in petroleum ether (bp 60°–80°) as eluant to yield the subtitled compound as a colourless oil (0.97 g, 58%).

Mass Spectrum: FAB (+ve) 366 [(M+H)$^+$];

$^1$H NMR (CDCl$_3$) δ:1.81 (quintet, 2H), 2.47 (t, 2H), 2.81 (t, 2H), 2.85 (t, 2H), 3.42 (t, 2H), 3.60 (t, 2H), 3.94 (t, 2H) 7.17–7.29 (m, 5H), 7.69–7.73 (m, 2H), 7.81–7.86 (m, 2H).

d) 1,3-Dihydro-2-[3,3-difluoro-6-[2-phenylethoxy]hexyl]-2H-isoindol-1,3-dione

The product from step c) (0.30 g) was stirred with diethylaminosulphur trifluoride (1 ml) under argon for 7 days. The mixture was then carefully poured into water and neutralised with sodium bicarbonate. The aqueous mixture was extracted with ether and washed with water and brine. The ether layer was dried (MgSO$_4$), filtered and the solvent removed under reduced pressure to leave the crude product which was purified by chromatography using diethyl ether in petroleum ether (bp 60°–80°) as eluant to provide the subtitled compound as a colourless oil (0.210 g, 66%).

Mass Spectrum: FAB (+ve) 388 [(M+H)$^+$];

$^1$H NMR (CDCl$_3$) δ:1.60–1.69 (m, 2H), 1.78–2.01 (m, 2H), 2.24 (t, 2H), 2.87 (t, 2H), 3.46 (t, 2H), 3.62 (t, 2H), 3.90 (t, 2H), 7.17–7.33 (m, 5I), 7.70–7.76 (m, 2H), 7.84–7.90 (m, 2H).

e) 3,3-Difluoro-6-[2-phenylethoxy]hexyamine hydrochloride

The product from step d) (1.6 g) was refluxed with hydrazine hydrate (0.265 ml) in methanol (50 ml) under an inert atmosphere for 2 hours. The solvent was removed under reduced pressure and the residue taken up in ether. The mixture was filtered and the solvent removed under reduced pressure. Formation of the hydrochloride provided is the subtitled compound (0.998 g) which was used without further purification.

Mass Spectrum: TSP 258 [(M+H)$^+$];

$^1$H NMR (D$_6$-DMSO) δ:1.58–1.64 (m, 2H), 1.82–1.96 (m, 2H), 2.18–2.31 (m, 2H), 2.80 (t, 2H), 2.88–2.94 (m, 2H), 3.42 (t, 2H), 3.58 (t, 2H), 7.15–7.43 (m, 5H), 8.17 (s, 3H).

f) N-3,3-Difluoro-6-[2-phenylethoxy]hexyl-2-[4-hydroxy-2-oxo-3H-1,3-benzothiazole-7-yl] acetamide The subtitled compound was prepared using the method outlined in Example 15a) using 4-hydroxy-2-oxo-3H-1,3-benzothiazole-7-acetic acid [this example steps a) and b)].

Mass Spectrum: FAB (+ve) 465 [(M+H)$^+$];

$^1$H NMR (D$_6$-DMSO) δ:1.56–1.61 (m, 2H), 1.81–1.86 (m, 2H), 1.97–2.02 (m, 2H), 2.79 (t, 2H), 3.18 (q, 2H), 3.31 (s, 2H), 3.38 (t, 2H), 3.56 (t, 2H), 6.70 (d, 1H), 6.84 (d, 1H), 7.17–7.29 (m, 5H), 8.10 (brt, 1H), 9.96 (s, 1H), 11.62 (s, 1H).

g) 7-[2-[3,3-Difluoro-6-[2-phenylethoxy]hexylamino]ethyl]-4-hydroxy-1,3-benzothiazol-2 (3H)-one hydrochloride The title salt was prepared using the method outlined in Example 15d) using the material from step f).

mp 240°–243°;

Mass Spectrum: FAB (+ve) 451 [(M+H)$^+$];

$^1$H NMR (D$_6$-DMSO) δ:1.60–1.66 (m, 2H), 1.82–1.97 (m, 2H), 2.26–2.39 (m, 2H), 2.81–2.94 (m, 4H), 3.05–3.19 (brs, 4H), 3.42 (t, 2H), 3.58 (t, 2H), 6.77 (d, 1H), 6.87 (d, 1H), 7.17–7.30 (m, 5H), 9.06 (brs, 2H), 10.16 (s, 1H), 11.79 (s, 1H);

Analysis: Found; C,56.63; H,6.27; N,5.98; S,6.33%.

C$_{23}$H$_{28}$F$_2$N$_2$O$_3$S.HCl requires: C,56.72; H,6.00; N,5.75; S,6.58%.

EXAMPLE 18

2-[3-[2-[4-Hydroxy-2-oxo-3H-1,3-benzothiazol-7-yl]ethylamino]propyl]-2-[2-phenylethoxy] ethylpropanedinitrile hydrochloride a) 2-[2-Phenylethoxy]ethylidene propanedinitrile β-Alanine (0.6 g) was added to a solution of [2-phenylethoxy]acetaldehyde (8.0 g) and malononitrile (3.5 g) in ethanol (100 ml). The mixture was stirred at room temperature for 3 hours. The solid was filtered off, washed with fresh ethanol and dried to yield the subtitled compound (5.85 g, 54%).

mp 135°–136°;

Mass Spectrum:212 (M$^+$).

b) 2-[2-Phenylethoxy]ethylpropanedinitrile

Sodium borohydride (0.19 g) was added to a solution of the compound from step a) (2.12 g) in dry tetrahydrofuran. The mixture was stirred for 4 hours at room temperature and partitioned between dilute hydrochloric acid and ether. The ether layer was separated off, washed with water and brine, dried (MgSO$_4$) and evaporated under reduced pressure to yield the subtitled compound (1.53 g, 71.5%).

Mass Spectrum: TSP (–ve) 213 [(M–H)]$^+$;

$^1$H NMR (CDCl$_3$) δ:2.23 (m, 2H), 2.88 (t, 2H), 3.64 (t, 2H), 3.70 (t, 2H), 3.77 (t, 1H), 7.25 (m, 5H).

c) 2-[1,3-Dioxolan-2-yl]ethyl-2-[2-phenylethoxy] ethylpropanedinitrile

A solution of the compound from step b) (1.53 g) in dry dimethyl sulphoxide (20 ml) was added to a suspension of sodium hydride (prewashed with diethyl ether) in dimethyl sulphoxide (20 ml). The mixture was stirred for 2 hours at room temperature. 2-[2-Bromoethyl]-1,3-dioxolane (0.920 ml) was then added and the whole heated at 60° for a further 2 hours. The cooled mixture was then quenched with water, acidified with dilute aqueous hydrochloric acid and extracted with ethyl acetate. The combined organic extracts were washed with water and brine, dried (MgSO$_4$) and evaporated under reduced pressure to yield the crude final product. This material was purified by flash chromatography over silica using ethyl acetate in dichloromethane as eluant to yield a pure sample of the subtitled compound (0.56g, 25%).

Mass Spectrum: FAB (+ve) 315 [(M+H)]+;

1H NMR (CDCl$_3$) δ:2.08 (m, 4H), 2.20 (t, 2H), 2.91 (t, 2H), 3.70 (t, 2H), 3.74 (t, 2H), 3.93 (t, 4H), 4.96 (t, 1H), 7.24 (m, 5H).

d) 4,4-Dicyano-6-[2-phenylethoxy]hexanal

The material from step c) (0.500 g) was dissolved in 80% formic acid (5 ml) and left to stand at room temperature until TLC analysis indicated that the reaction had gone to completion (17 hours). The reaction mixture was partitioned between aqueous sodium bicarbonate solution and ethyl acetate. The combined organic extracts were washed with aqueous sodium bicarbonate solution and brine, dried and evaporated to yield the subtitled compound as a colourless oil (0.349 g, 70%). This was used without further purification.

Mass Spectrum: EI 270 (M$^+$);

$^1$H NMR (CDCl$_3$) δ:2.22 (t, 2H), 2.29 (t, 2H), 2.86 (t, 2H), 2.91 (t, 2H), 3.73 (m, 4H), 7.26 (m, 5H), 9.79 (s, 1H).

e) 2-[3-[2-[4-Hydroxy-2-oxo-3H-1,3-benzothiazol-7-yl]ethylamino]propyl]-2-[2-phenylethoxy] ethylpropanedinitrile hydrochloride To a solution of the material from step d) (0.35 g) in methanol (10 ml) was added 7-[2-aminoethyl]-4-hydroxy-1,3-benzthiazol-2(3H)-one hydrobromide (0.271 g) followed by sodium cyanoborohydride (0.044 g) and 15 drops of 6% aqueous acetic acid. The suspension was stirred at room temperature for 3 hours at which point TLC analysis indicated that no starting aldehyde remained. The reaction mixture was made basic with concentrated aqueous ammonium hydroxide and the methanol removed under reduced pressure. Purification by flash chromatography over silica using methanol in dichloromethane as eluant gave a crude sample of the title compound (0.180 g). This material was purified by reverse phase HPLC chromatography using a 35% solution of acetonitrile in 0.1% aqueous trifluoroacetic acid as eluant. After evaporation of the solvents the solid residue was dissolved in isopropyl alcohol and ethanolic hydrochloric acid was added. The solvents were removed under reduced pressure and the residual hydrochloric acid salt was triturated with diethyl ether.

mp 130° (softens);

Mass Spectrum: TSP 465 [(M+H)$^+$];

$^1$H NMR (D$_6$-DMSO) δ:1.5–2.2 (m, 4H), 2.2–2.5 (t, 2H), 2.81 (m, 4H), 3.25 (brt, 2H), 3.5–3.8 (m, 6H), 6.77 (d, 1H), 6.93 (d, 1H), 7.23 (m, 5H), 9.33 (s, 1H), 9.51 (s, 1H), 10.16 (s, 1H), 11.79 (s, 1H);

Analysis: Found; C,57.21; H,6.21; N,10.27; S,5.18%,

C$_{25}$H$_{28}$N$_4$O$_3$S.HCl.1.5 H$_2$O requires: C,56.68; H,6.11; N,10.62; S,6.07%.

EXAMPLE 19

N-[2-[2-[4-Hydroxy-2-oxo-3H-1,3-benzothiazole-7-yl]ethylamino]ethyl]-N-methyl-3-[2-phenylethoxy] propanamide hydrochloride a) 3-[2-Phenylethoxy]propanoic acid Pyridinium dichromate (100 g) was added to a solution of 3-[2-phenylethoxy]-propanol (13.6 g) (prepared from 2-phenylmethyl-1,3-dioxane following the method described in Can. J. Chem., 1974, 52, 888) in DMF (400 ml). The whole was rapidly stirred for 6 hours at which point water was added. This was then extracted with ether (×3). The combined ethereal layers were extracted with 10% aqueous sodium hydroxide solution (500 ml). The basic solution was made acidic pH 1–2 with concentrated hydrochloric acid and extracted with ether. These ethereal extracts were then combined, washed with brine, dried (MgSO$_4$) and evaporated under reduced pressure to yield the subtitled compound (7.6 g).

$^1$H NMR (CDCl$_3$) δ:2.61 (t, 2H), 2.89 (t, 2H), 3.69 (t, 2H), 3.71 (t, 2H), 7.15–7.48 (m, 5H).

b) N-[2-[2,2-Dimethoxy]ethyl]-N-methyl-3-[2-phenylethoxy]propanamide

The subtitled compound was prepared by the method outlined in Example 15a) using the material from step a) (1 g), 1-hydroxybenzotriazole hydrate (0.696 ) and N-methyl-2,2-dimethoxyethylamine (0.661 ml) except that no triethylamine was employed. This yielded the subtitled compound (0.9 g).

Mass Spectrum: FAB (+ve) 296 [(M+H)$^+$];

$^1$H NMR (CDCl$_3$) δ:2.59–2.67 (m, 2H), 2.90 (t, 2H), 2.98 and 3.05 (2×s, total 3H), 3.39 and 3.40 (2×s, total 6H), 3.44 (d, 2H), 3.63–3.70 (m, 2H), 3.78 (t, 2H), 4.41 and 4.49 (2×t, total 1H), 7.18–7.41 (m, 5H).

c) N-[2-[2-[4-Hydroxy-2-oxo-3H-1,3-benzothiazole-7-yl]ethylamino]ethyl]-N-methyl-3-[2-phenylethoxy]propanamide hydrochloride The material from step b) (1.4 g) was mixed with acetic acid (20 ml) and heated at 100° for 1 hour under nitrogen. The acetic acid was removed under reduced pressure and the residue (1.38 g) was dissolved in methanol (50 ml). To this solution was added sodium cyanoborohydride (0.224 g), 7-[2-aminoethyl]-4-hydroxy-1,3-benzthiazol-2(3H)-one hydrobromide (1.4 g) and 6% aqueous acetic acid (1 ml). The whole was stirred overnight at room temperature. The mixture was made basic by the addition of concentrated aqueous ammonium hydroxide solution. The volatiles were removed under reduced pressure and the residual material purified by chromatography over silica using 10–25% methanol in chloroform as eluant. The material was further purified by reverse phase HPLC using 25% acetonitrile in 0.1% aqueous trifluoroacetic acid as eluant to yield, after preparation of the hydrochloride salt, the title compound.

mp 138°–146 (softens);

Mass Spectrum: FAB (+ve) 444 [(M+H)$^+$];

$^1$H NMR (D$^6$-DMSO) (mixture of rotamers) δ:2.56–2.63 (m, 2H), 2.77–2.87 (m, 4H), 2.97 (s, 3H), 3.08 (brm, 4H), 3.55–3.65 (m, 6H), 6.77 (m, 1H), 6.86 (m, 1H), 7.15–7.35 (m, 5H), 8.88 and 9.09 (2×brs, total 2H), 10.17 (brs, 1H), 11.78 and 11.80 (2×s), total 1H).

EXAMPLE 20

4-Hydroxy-7-[2-[3-[2-[2-phenylethoxy] ethylsulphonyl]propylamino]ethyl]-1,3-benzothiazol-2(3H)-one hydrochloride a) 3-[2-[2-Phenylethoxy]ethylthio]propanoic acid A solution of 2-[2-phenylethoxy]ethane thiol (2.13 g) in dry DMF (10 ml) was added dropwise to a cooled (0°) stirred suspension of sodium hydride (0.60 g, 80% in oil) in DMF (50 ml). The mixture was stirred at 0° for 90 min. A solution of 3-bromopropanoic acid (3.15 g) in dry DMF (10 ml) was then added dropwise and the reaction was stirred at room temperature for 16 hours. Water (250 ml) was added and the whole was acidified to pH 2/3 with concentrated hydrochloric acid. The aqueous solution was extracted several times with ether and the combined ethereal layers were washed with water and brine, dried (MgSO$_4$) and evaporated under reduced pressure. This yielded the crude acid which was purified by flash chromatography over silica using 6:1 dichloromethane:ether (1 drop acetic acid/100 ml of eluant) to give the subtitled compound (2.15 g).

$^1$H NMR (CDCl$_3$) δ:2.6–2.8 (m, 4H), 2.81 (t, 2H), 2.89 (t, 2H), 3.6–3.76 (m, 4H), 7.2–7.4 (m, 5H).

b) 3-[2-[2-Phenylethoxy]ethylsulphonyl]propanoic acid

A solution of potassium peroxymonosulphate (15.6 g, OXONE™) in water (50 ml) was added dropwise to a cooled (0°) solution of the material from step a) (2.15 g) in methanol (50 ml). After the addition was complete the ice bath was removed and the reaction stirred at room temperature for 4 hours. The whole was poured into water and extracted with chloroform (×3). The combined organic extracts were washed with water, dried (MgSO$_4$) and evaporated under reduced pressure to give the subtitled compound as a white solid (1.91 g, 79%).

Mass Spectrum: EI TMS derivative 343 [(M–15)$^+$];

$^1$H NMR (CDCl$_3$) δ:2.76 (t, 2H), 2.91 (t, 2H), 3.19 (m, 4H), 3.72 (t, 2H), 3.86 (t, 2H), 7.15–7.3 (m, 5H).

c) N-[2-[4-Hydroxy-2-oxo-3H-1,3-benzothiazol-7-yl]ethyl]-3-[2-[2-phenylethoxy]-ethylsulphonyl] propanamide Triethylamine (0.70 ml), 1-hydroxybenzotriazole hydrate (0.98 g) and finally dicyclohexylcarbodiimide (1.49 g) were added to a stirred solution of 7-[2-aminoethyl]-4-hydroxy-1,3-benzothiazol-2(3H)-one hydrobromide (1.62 g) and the material from step b) (1.75 g) in DMF (25 ml). The whole was stirred for 16 hours at room temperature. Glacial acetic acid (0.1 ml) was added and stirring continued for 15 min. The DMF was removed under reduced pressure and the residue slurried with ethyl acetate (50 ml). The suspended dicyclohexylurea was removed by filtration. The filtrate was washed with saturated aqueous sodium bicarbonate and dried (MgSO$_4$). The solvent was removed under reduced pressure to yield a residue which was purified by column chromatography over silica using 95:5 dichloromethane:ethanol to give the subtitled compound (1.89 g, 71%).

mp 142°–144°;

Mass Spectrum: FAB (+ve) 479 [(M+H)$^+$];

$^1$H NMR (D$_6$-DMSO) δ:2.50 (m, 2H), 2.61 (t, 2H), 2.81 (t, 2H), 3.2–3.4 (brm, 6H+D$_2$O), 3.64 (t, 2H), 3.75 (t, 2H), 6.70 (d, 1H), 6.80 (d, 1H), 7.15–7.30 (m, 5H), 8.14 (t, 1H), 10.0 (brs, 1H), 11.5 (s, 1H);

Analysis: Found; C,55.03; H,5.55; N,5.90; S,13.07%.

C$_{22}$H$_{26}$N$_2$O$_6$S$_2$ requires: C,55.21; H,5.48; N,5.85; S,13.39%.

d) 4-Hydroxy-7-[2-[3-[2-[2-phenylethoxy]ethylsulphonyl]propylamino]ethyl]-1,3-benzothiazol-2(3H)-one hydrochloride Borane-tetrahydrofuran solution (1.0M in THF, 15 ml) was added dropwise to a stirred solution of the product from step c) (2.06 g) in dry tetrahydrofuran (100 ml). The reaction was refluxed under an inert atmosphere until thin layer chromatography indicated that no more starting material remained. The reaction was cooled and methanol (3.5 ml) was added (CAUTION!)). The reaction was refluxed for a further 30 min. The solvents were removed under reduced pressure and the residue dissolved in methanol (100 ml) to which was added concentrated hydrochloric acid (sg. 1.18, 0.75 ml). This was refluxed for 30 min. Cooling and removal of the methanol under reduced pressure yielded an oily residue which when triturated with ether gave the crude title compound as a pale yellow solid. Portions of the title compound were purified by preparative reverse phase HPLC using methanol and 0.1% trifluoroacetic acid as eluant. Finally preparation of the hydrochloride salt, by dissolving in a small amount of ethanol and treatment with dry ethereal hydrochloric acid followed by removal of the solvents, gave the title salt as a white powder.

mp 201°–203°;

Mass Spectrum: FAB (+ve) 465 [(M+H)$^+$];

$^1$H NMR (D$_6$-DMSO) δ:2.01 (m, 2H), 2.80 (m, 4H), 2.98 (brs, 2H), 3.10 (t, 4H), 3.36 (t, 2H), 3.66 (t, 2H), 3.77 (t, 2H), 6.77 (d, 1H), 6.88 (d, 1H), 7.2–7.35 (m, 5H), 8.98 (brs, 2H), 10.13 (brs, 1H), 11.77 (s, 1H);

Analysis: Found; C,52.31; H,5.85; N,5.54; S,12.54; Cl,7.48%.

C=H$_{28}$N$_2$O$_5$S$_2$.HCl requires: C,52.73; H,5.83; N,5.90; S,12.79; Cl,7.08%.

EXAMPLE 21

4-Hydroxy-7-[2-[2-[3-[2-phenylethoxy]propoxy]ethylamino]ethyl]-1,3-benzothiazol-2(3H)-one hydrochloride a) 2-[3-[2-Phenylethoxy]propoxy]acetic acid The subtitled compound was prepared following the general method outlined in Example 20a) using 3-[2-phenylethoxy]propanol (prepared from 2-phenylmethyl-1,3-dioxane following the method described in Can. J. Chem., 1974, 52, 888).

$^1$H NMR (CDCl$_3$) δ:1.89 (m, 2H), 2.90 (q, 2H), 3.49–3.60 (m, 6H), 4.05 (s, 2H), 7.21–7.30 (m, 5H).

b) N-[2-[4-Hydroxy-2-oxo-3H-1,3-benzothiazol-7-yl]ethyl]-2-[3-[2-phenylethoxy]propoxy]acetamide The subtitled compound was prepared according to the general method outlined in Example 20c).

mp 150°–151°;

Mass Spectrum: FAB (+ve) 431 [(M+H)$^+$];

$^1$H NMR (D$_6$-DMSO) δ:1.73 (m, 2H), 2.63 (t, 2H), 2.79 (t, 2H), 3.2–3.4 (brm, 6H+D$_2$O), 3.54 (t, 2H), 3.76 (brs, 2H), 6.69 (d, 1H), 6.79 (d, 1H), 7.16–7.29 (m, 5H), 8.12 (t, 1H), 9.92 (s, 1H), 11.61 (s, 1H);

Analysis: Found; C,60.90; H,6.02; N,6.40; S,6.91%.

C$_{22}$H$_{26}$N$_2$O$_5$S requires: C,61.37; H,6.09; N,6.51; S,7.45%.

c) 4-Hydroxy-7-[2-[2-[3-[2-phenylethoxy]propoxy]ethylamino]ethyl]-1,3-benzothiazol-2(3H)-one hydrochloride The title salt was prepared according to the general method outlined in Example 20d).

mp 159°–160°;

Mass Spectrum: FAB (+ve) 417 [(M+H)$^+$];

$^1$H NMR (D$_6$-DMSO) δ:1.75 (t, 2H), 2.79 (t, 2H), 2.87 (t, 2H), 3.12 (m, 4H), 3.45 (m, 4H+D$_2$O), 3.58 (m, 4H), 6.77 (d, 1H), 6.85 (d, 1H), 7.18–7.27 (m, 5H), 8.99 (brs, 2H), 10.16 (s, 1H), 11.8 (brs, 1H);

Analysis: Found; C.58.33; H.6.54; N,6.37; S,6.79; Cl.7.96%.

C$_{22}$H$_{28}$N$_2$O$_4$S.HCl requires: C.58.33; H.6.23; N,6.18; S.7.08; Cl.7.83%.

EXAMPLE 22

4-Hydroxy-7-[2-[3-[2-[2-phenylethoxy]ethoxy]propylamino]ethyl]-1,3-benzothiazol-2(3H)-one hydrochloride a) 3-[2-[2-Phenylethoxy]ethoxy]propanenitrile

A mixture of 3-(2-phenylethoxy)ethanol (8.0 g, prepared from 2-phenylmethyl 1,3-dioxolane according to the general method in *Can. J. Chem.*, 1974, 52, 888), 3-bromopropanenitrile (5.6 ml), sodium hydroxide (50 g) and tetrabutylammonium chloride (0.5 g) in dichloromethane (100 ml) and water (100 ml) was stirred at room temperature for 72 hours. The mixture was diluted with water and the organic layer separated. The aqueous layer was extracted with a further portion of dichloromethane. The combined organic extracts were washed with dilute aqueous hydrochloric acid and water, dried (MgSO$_4$) and evaporated under reduced pressure to yield the crude product. This material was purified by flash chromatography over silica using 1:1 ether:petroleum ether (bp 60°–80°) as eluant to give the subtitled compound as an oil (9.84 g, 90%).

Mass Spectrum: EI 219 (M$^+$);

$^1$H NMR (CDCl$_3$) δ:2.55 (t, 2H), 2.90 (t, 2H), 3.61–3.74 (m, 8H), 7.18–7.36 (m, 5H).

b) 3-[2-[2-Phenylethoxy]ethoxy]propanal

Diisobutylaluminum hydride (3.3 ml, 1.5M in toluene) was added dropwise to a cooled (0°) stirred solution of 3-[2-[2-phenylethoxy]ethoxy]propanenitrile (1.0 g) from step a) in tetrahydrofuran. After 30 min the mixture was warmed to room temperature and stirred for a further 2 hours. Water and 10% aqueous hydrochloric acid were added cautiously and the reaction stirred for a further 5 min. The reaction was extracted several times with ether and the combined ethereal extracts were washed with saturated aqueous sodium bicarbonate solution and brine, dried (MgSO$_4$) and evaporated under reduced pressure to yield the subtitled compound as a yellow oil. The material was used in the next step without purification.

c) 4-Hydroxy-7-[2-[3-[2-[2-phenylethoxy]ethoxy]propylamino]ethyl]-1,3-benzothiazol-2(3H)-one hydrochloride Sodium cyanoborohydride (0.333 g) was added to a stirred solution of 3-[2-[2-phenylethoxy]ethoxy]propanal from step b) (2.2 g), 6% aqueous acetic acid (2 ml) and 7-[2-aminoethyl]-4-hydroxy-1,3-benzothiazol-2(3H)-one hydrobromide (2.05 g) in methanol (180 ml). The reaction was stirred for 2 hours at room temperature by which time HPLC analysis revealed that all the starting material had been consumed. The reaction was made basic with concentrated aqueous ammonium hydroxide solution and the methanol was removed under reduced pressure to yield the crude product. Purification by chromatography over silica using methanol in chloroform as the eluant, reverse phase preparative HPLC in methanol 0.1% aqueous trifluoroacetic acid as eluant and finally formation of the hydrochloride salt gave the title compound as a white solid.

mp 186°–190°;

Mass Spectrum: FAB (+ve) 417 [(M+H)$^+$];

$^1$H NMR (D$_6$-DMSO) δ:1.80–1.88 (m, 2H), 2.78–2.86 (m, 4H), 2.97 (t, 2H), 3.09 (t, 2H), 3.46 (t, 2H), 3.47–3.58 (m, 4H), 3.60 (t, 2H), 6.76 (d, 1H), 6.88 (d, 1H), 7.16–7.29 (m, 5H), 8.70 (brs, 2H), 10.13 (s, 1H), 11.76 (brs, 1H);

Analysis: Found; C.55.24; H.5.98; N,5.92; S,6.36; Cl.7.35%.

C$_{22}$H$_{28}$N$_2$O$_4$S.HCl.1.42 H$_2$O requires: C,55.20; H,6.41; N,5.88; S,6.70; Cl,7.41%.

EXAMPLE 23

4-Hydroxy-7-[2-[2-[2-[2-phenylethoxy]ethoxy]ethylamino]ethyl]-1,3-benzothiazol-2(3H)-one hydrochloride a) 2-[2-[2-Phenylethoxy]ethoxy]acetic acid

Sodium hydride (60% dispersion in oil, 0.86 g) was washed several times with petroleum ether and suspended in tetrahydrofuran (5 ml). A solution of 2-[2-phenylethoxy]ethanol (1.5 g, prepared from 2-phenylmethyl-1,3-dioxolane according to the general method in *Can. J. Chem.*, 1974, 52, 888) in tetrahydrofuran (10 ml) was added dropwise to the suspension and the mixture heated to 55° for 15 min and then stirred at room temperature for 2 hours. Chloroacetic acid (0.85 g) in tetrahydrofuran (5 ml) was added and stirring was continued for 17 hours at room temperature. The tetrahydrofuran was removed under reduced pressure and the residue partitioned between saturated aqueous sodium bicarbonate and diethyl ether (the ethereal layer was discarded). The separated aqueous layer was acidified using aqueous dilute hydrochloric is acid and extracted with diethyl ether. The organic extracts were washed with saturated brine, dried (MaSO$_4$) and evaporated under reduced pressure to give a pale brown oil (1.48 g). Chromatography over silica using 1:1 ether petroleum ether (bp 60°–80°) as eluant yielded the subtitled compound (1.07 g).

$^1$H NMR (CDCl$_3$) δ:2.94 (t, 2H), 3.49–3.82 (m, 6H), 4.16 (s, 2H), 7.18–7.34 (m, 5H).

b) N-[2-[4-Hydroxy-2-oxo-3H-1,3-benzothiazol-7-yl ethyl]-2-[2-[2-phenylethoxy]ethyl]acetamide The subtitled compound was prepared according to the general method outlined in Example 20c).

Mass Spectrum: FAB (+ve) 417 [(M+H)$^+$];

$^1$H NMR (D$_6$-DMSO) δ:2.61 (t, 2H), 2.79 (t, 2H), 3.31 (m, 6H), 3.60 (t, 2H), 3.82 (s, 2H), 6.69 (d, 1H), 6.79 (d, 1H), 7.15–7.29 (m, 5H), 7.72 (t, 1H), 9.91 (brs, 1H), 11.61 (brs, 1H).

c) 4-Hydroxy-7-[2-[2-[2-[2-phenylethoxy]ethoxy]ethylamino]ethyl]-1,3-benzothiazol-2(3H)-one hydrochloride The title compound was prepared using the general method outlined in Example 20d).

mp 123°;

Mass Spectrum: FAB (+ve) 403 [(M+H)$^+$];

$^1$H NMR (D$_6$-DMSO) δ:2.78 (t, 2H), 2.85 (t, 2H), 3.09 (m, 4H), 3.56 (m, 6H), 3.65 (t, 2H), 6.77 (d, 1H), 6.83 (d, 1H), 7.08–7.29 (m, 5H), 9.00 (s, 2H), 10.15 (s, 1H), 11.69 (s, 1H);

Analysis: Found; C,56.62; H,6.15; N,6.43; Cl,9.40%,
C$_{21}$H$_{26}$N$_2$O$_4$S.HCl excess 0.18 moles HCl requires:
C,56.62; H,6.14; N,6.29; Cl,9.37%.

EXAMPLE 24

4-Hydroxy-7-[2-[2-[3-[2-phenylethoxy]propylthio]
ethylamino]ethyl]-1,3-benzothiazol-2(3H)-one
hydrochloride a) 3-Mercaptopropanol

A solution of thiourea (36 g) in water (100 ml) was mixed with 3-bromopropanol (33 ml) and refluxed for 4 hours. The mixture was allowed to cool slightly and 10% aqueous sodium hydroxide solution (190 ml) added. The mixture was heated under reflux for a further 3 hours, allowed to cool and left to stand for 17 hours at room temperature. The reaction mixture was acidified to pH 4 using concentrated sulphuric acid and extracted with diethyl ether. The combined organic extracts were dried (MgSO$_4$) and concentrated under reduced pressure to give the crude product as a yellow liquid. Distillation gave the subtitled compound (14.67 g).

Mass Spectrum: EI 92 (M$^+$);

$^1$H NMR (CDCl$_3$) δ:1.40 (m, 1H), 1.91 (m, 3H), 2.63 (q, 2H), 3.75 (t, 2H).

b) 2-Phenylmethyl-1,3-oxathiane

To a solution of the thiol (14.67 g) from step a) in toluene (200 ml) was added p-toluenesulphonic acid (1 g) and phenylacetaldehyde (18.3 ml). The reaction was refluxed using a Dean and Stark apparatus. After the appropriate amount of water had been collected the reaction mixture was cooled, washed with saturated sodium bicarbonate, saturated brine and dried (K$_2$CO$_3$). The crude product was distilled (bp 100°–110°/0.3 mbars) to give a yellow liquid (19.65 g).

Mass Spectrum: EI 194 (M$^+$);

$^1$H NMR (CDCl$_3$) δ:1.66 (d, 1H), 1.95 (m, 1H), 2.7 (m, 1H), 2.94 (m, 2H), 3.10 (m, 1H), 3.53 (t, 1H), 4.14 (d, 1I), 4.90 (t, 1H), 6.69–7.32 (m, 5H).

c) 3-[2-Phenylethoxy]propanethiol

Calcium turnings (3.5 g) were added portionwise to liquid ammonia (500 ml) and the whole was stirred vigorously for 10 min. The thioacetal from step b) (10 g) in ether (7 ml) was added dropwise to the dark blue solution over a 7 min period. The mixture was stirred for 2 hours and then quenched with ammonium chloride until effervescing had ceased. Excess ammonia was allowed to evaporate by purging under nitrogen overnight. The remaining solid was acidified using dilute 10% aqueous hydrochloric acid to pH 1–2 and the product extracted with ethyl acetate. The organic layers were combined, washed with water and brine, dried (MgSO$_4$) and concentrated under reduced pressure to give the subtitled compound (8.29 g).

Mass Spectrum: EI 196 (M$^+$);

$^1$H NMR (CDCl$_3$) δ:1.29 (d, 1H), 1.86 (m, 2H), 2.56 (q, 2H), 2.87 (t, 2H), 3.49 (t, 2H), 3.64 (t, 2H), 6.97–7.31 (m, 5H).

d) 2-[3-[2-Phenylethoxy]propylthiolacetic acid

Sodium hydride (60%, 3.38 g) was washed with petroleum ether and suspended in dimethylformamide (5 ml) at 0°. A solution of the thiol from step c) in dimethylformamide (8.29 g in 10 ml) was added dropwise. Stirring was continued for 2 hours at 0°–8° at which point a solution of bromoacetic acid (5.88 g) in dimethylformamide (15 ml) was added dropwise. A further quantity of dimethylformamide (20 ml) was added to aid stirring. After 17 hours at room temperature the dimethylformamide was removed under reduced pressure. The residue was partitioned between saturated aqueous sodium bicarbonate and diethyl ether (the ethereal layer was discarded). The aqueous layer was separated, acidified with hydrochloric acid to pH 1–2 and extracted with diethyl ether. The ethereal extracts were combined, washed with water and brine, dried (MgSO,) and concentrated under reduced pressure. Chromatography of the crude material over silica using 1:1 petroleum ether (bp 60°–80°):ether as eluant gave the subtitled compound (7.10 g). $^1$H NMR (CDCl$_3$) δ:1.86 (m, 2H), 2.70 (t, 2H), 2.87 (t, 2H), 3.21 (s, 2H), 3.51 (t, 2H), 3.63 (t, 2H), 7.17–7.30 (m, 5H), 9.74 (s, 1H).

e) N-[2-[4-Hydroxy-2-oxo-3H-1,3-benzothiazol-7-yl]ethyl]-2-[3-[2-phenylethoxy]-propylthio] acetamide The subtitled compound was prepared using the general method outlined in Example 20c) using 7-[2-aminoethyl]-4-hydroxy-1,3-benzothiazol-2(3H)-one hydrobromide to yield, after purification by chromatography over silica using 9:1 dichloromethane:ethanol as eluant, the, subtitled compound (1.08 g).

Mass Spectrum: FAB (+ve) 447 [(M+H)$^+$];

$^1$H NMR (D$_6$-DMSO) δ:1.70 (m, 2H), 2.65 (t, 2H), 2.67 (t, 2H), 2.78 (t, 2H), 3.05 (s, 2H), 3.28 (q, 2H), 3.41 (t, 2H), 3.53 (t, 2H), 6.71 (d, 1H), 6.83 (d, 1H), 7.15–7.43 (m, 5H), 8.05 (s, 1H), 9.9 (s, 1H), 11.62 (s, 1H).

f) 4-Hydroxy-7-[2-[2-[3-[2-phenylethoxy]propylthio]ethylamino]ethyl]-1,3-benzothiazol-2(3H)-one hydrochloride The title compound was prepared according to the general method outlined in Example 20d). The crude product was purified by reverse phase HPLC using 0.1% aqueous trifluoroacetic acid methanol as eluant.

mp 209°–211°;

Mass Spectrum: FAB (+ve) 433 [(M+H)$^+$];

$^1$H NMR (D$_6$-DMSO) δ:1.82 (m, 2H), 2.62 (m, 4H), 2.87 (m, 4H), 2.93 (m, 2H), 3.16 (m, 2H), 3.53 (t, 2H), 3.65 (t, 2H), 6.83 (d, 1H), 6.94 (d, 1H), 7.26–7.37 (m, 5H), 9.02 (s, 2H), 10.21 (s, 1H), 11.83 (s, 1H);

Analysis: Found; C,55.36; H,6.35; N,6.12; S,13.30%,
C$_{22}$H$_{28}$N$_2$O$_3$S$_2$.HCl excess 0.46 moles H$_2$O requires:
C,55.36; H,6.32; N,5.87; S,13.41%.

EXAMPLE 25

4-Hydroxy-7-[2-[2-[3-[2-[2-phenylethoxy]
propylsulphonyl]ethylamino]ethyl]-1,3-
benzothiazol-2(3H)-one hydrochloride a) 2-[3-[2-Phenylethoxy]propylsulphonyl]acetic acid

The subtitled compound was prepared from 2-[3-[2-phenylethoxy]propanethio]-acetic acid [Example 24d)] using the general method described in Example 20b).

Mass Spectrum: FAB (+ve) 287 [(M+H)$^+$];

$^1$H NMR CDCl$_3$ δ: 2.12 (m, 2H), 2.87 (t, 2H), 3.41 (t, 2H), 3.58 (t, 2H), 3.67 (t, 2H), 3.97 (s, 2H), 7.00–7.43 (m, 5H), 8.79 (s, 1H).

b) N-[2-[4-Hydroxy-2-oxo-3H-1,3-benzothiazole-7-yl]ethyl]-2-[3-[2-phenylethoxy]-propylsulphonyl] acetamide The subtitled compound was prepared according to the general method outlined in Example 20c). The crude material was purified by flash chromatography over silica using 9:1 dichloromethane:methanol as eluant.

Mass Spectrum: FAB (+ve) 479 [(M+H)$^+$];

$^1$H NMR (D$_6$-DMSO) δ:1.92 (q, 2H), 2.62 (t, 2H), 2.81 (t, 2H), 3.27 (m, 4H), 3.49 (t, 2H), 3.58 (t, 2H), 4.04 (s, 2H), 6.70 (d, 1H), 6.83 (d, 1H), 7.17–7.29 (m, 5H), 8.47 (t, 1H), 9.96 (s, 1H), 11.66 (d ,1H).

c) 4-Hydroxy-7- [2-[2- [3-[2-phenylethoxy] propylsulphonyl]ethylamino]ethyl]-1,3-benzothiazol-2(3H)-one hydrochloride The title compound was prepared by the general method outlined in Example 20d). The crude material was purified by reverse phase HPLC using 0.1% aqueous trifluoroacetic acid methanol as eluant.

mp 217°–220°;

Mass Spectrum: FAB (+ve) 465 [(M+H)$^+$];

$^1$H (D$_6$-DMSO) δ:1.91 (quin, 2H), 2.81 (t, 2H), 2.87 (t, 2H) 3.20 (m, 4H), 3.34 (t, 2H), 3.51 (t, 2H), 3.57 (q, 4H), 6.77 (d, 1H), 6.86 (d, 1H), 7.17–7.31 (m, 5H), 9.27 (s, 2H), 10.15 (s, 1H), 11.77 (s, 1H);

Analysis: Found: C,52.57; H,6.05; N,5.73; S,12.61%,

C$_{22}$H$_{28}$N$_2$O$_5$S$_2$.HCl requires: C,52.73; H,5.83; N,5.59; S,12.79%.

EXAMPLE 26

4-Hydroxy-7-[2-[3-[2-[2-phenylethoxy]ethylthio] propylamino]ethyl-1,3-benzothiazol-2(3H)-one hydrochloride a) N-[2-[4-Hydroxy-2-oxo-3H-1,3-benzothiazol-7-yl]ethyl]-3-[2-[2-phenylethoxy]-ethylthio] propanamide The subtitled compound was prepared using the general method outlined in Example 20c). Using the compound from Example 1a).

Mass Spectrum: FAB (+ve) 447 [(M+H)$^+$];

$^1$H NMR (D$_6$-DMSO) δ:2.26–2.33 (t, 2H), 2.54–2.72 (m, 6H), 2.75–2.83 (t,2H), 3.19–3.28 (q, 2H), 3.50–3.63 (2×t, 4H), 6.68 (d, 1H), 6.78 (d, 1H), 7.15–7.3 (m, 5H), 7.95 (t, 1H), 9.89 (s, 1H), 11.60 (brs, 1H).

b) 4-Hydroxy-7-[2-[3-[2-[2-[2-phenylethoxy] ethylthio]propylamino]ethyl]-1,3-benzothiazol-2 (3H)-one hydrochloride The title compound was prepared using the general method outlined in Example 20d).

mp 211°–213°;

Mass Spectrum: FAB (+ve) 433 [(M+H)$^+$];

$^1$H NMR (D$_6$-DMSO) δ:1.85 (m, 2H), 2.59 (t, 2H), 2.65 (t, 2H), 2.81 (t, 2H), 2.85 (t, 2H), 2.97 (t, 2H), 3.08 (m, 2H), 3.56 (t, 2H), 3.61 (t, 2H), 6.76 (d, 1H), 6.87 (d, 1H), 7.17–7.30 (m, 5H), 8.9 (brs, 2H), 10.14 (s, 1H), 11.76 (s, 1H);

Analysis: Found; C,56.49; H,6.40; N,6.12; S,13.78; Cl,7.98%,

C$_{22}$H$_{28}$N$_2$O$_3$S$_2$.HCl requires: C,56.33; H,6.23; N,5.97; S,13.67; Cl,7.56%.

EXAMPLE 27

4-Hydroxy-7- [2-[3-[2-[2-phenylethoxy] ethylsulphonyl]propylamino]ethyl]-1,3-benzothiazol-2(3H)-one 4-methylbenzenesulphonate a) 4-Hydroxy-7-[2-[3-[2-[2-phenylethoxy] ethylsulphonyl]propylamino]ethyl]-1,3-benzothiazol-2(3H)-one An aqueous solution (500 ml) of the title compound from Example 20 (4.9 g) was mixed with an excess of aqueous sodium hydrogen carbonate. The free base was extracted with chloroform and the combined extracts were washed with water and dried (MgSO$_4$), filtered and the chloroform removed under reduced pressure to yield the subtitled compound as an off-white solid (4.22 g, 91%).

mp 69°–70°.

b) 4-Hydroxy-7-[2-[3-[2-[2-phenylethoxy]ethyl] sulphonyl]propylamino]ethyl]-1,3-benzothiazol-2 (3H)-one 4-methylbenzenesulphonate A portion of the free base was dissolved in methanol and one molar equivalent of 4-methylbenzenesulphonic acid was added. The solution was evaporated under reduced pressure and the solid collected was recrystallised (methanol/water) to yield the title compound as white needles.

mp 170°–171°.

EXAMPLE 28

4-Hydroxy-7-[2-[3-[2-[2-phenylethoxy] ethylsulphonyl]propylamino]ethyl]-1,3-benzothiazol-2(3H)-one hemisuccinate The title compound was prepared using the general method outlined in Example 27a) and b) using succinic acid.

mp 18°2–183°, lustrous white plates (recrystallised from methanol/water).

EXAMPLE 29

4-Hydroxy-7-[2-[3-[2-[2-phenylethoxy] ethylsulphonyl]prolamino]ethyl]-1,3-benzothiazol-2 (3H)-one hexanoate The title compound was prepared using the general method outlined in Example 27a) and b) using hexanoic acid.

mp 131°–132°, white needles (recrystallised from methanol/water).

EXAMPLE 30

4-Hydroxy-7-[2-(3-[2-[2-phenylethoxy] ethylsulphonyl]propylamino]ethyl-1,3-benzothiazol-2(3H)-one tartrate The title compound was prepared using the general method outlined in Example 27a) and b) using tartaric acid.

mp 158°–162°, (recrystallised from methanol/water).

EXAMPLE 31

4-Hydroxy-7-[2-[3-[2-[2-phenylethoxy] ethylsulphonyl]propylamino]ethyl]-1,3-benzothiazol-2(3H)-one 1-hydroxy-2-naphthoate (Xinafoate)

The title compound was prepared using the general method outlined in Example 27a) and b) using 1-hydroxy-2-naphthoic acid.

mp 176°–177°, white needles (recrystallised from methanol/water).

EXAMPLE 32

4-Hydroxy-7-[2-[3-[2-[2-[2-aminophenyl]ethoxy] ethylsulphonyl]propylamino]ethyl]-1,3-benzothiazol-2(3H)-one dihydrochloride a) Methyl 3-[2-[2-[2-nitrophenyl]ethoxy]ethylsulphonyl]propanoate

Concentrated nitric acid (3.25 ml) was added dropwise over a half hour period to a stirred cooled (ice/salt) solution of methyl 3-[2-[2-phenylethoxy]-ethylsulphonyl]propanoate (15.12 g) (prepared from the acid, which was itself prepared by the procedure outlined in Example 1b)) in trifluoroacetic acid. The reaction was allowed to warm to room temperature, stirred overnight, diluted with water and extracted several times with ethyl acetate. The combined organic extracts were washed with water and brine, dried ($MgSO_4$) and concentrated under reduced pressure to yield the crude mixture of isomeric methyl 3-[2-[2-[nitrophenyl] ethoxy]ethylsulphonyl propanoates. The subtitled compound was separated from the other isomers by normal phase preparative HPLC using 1:1 hexane:ethyl acetate as eluant.

$^1$H NMR ($CDCl_3$) δ:2.80–2.84 (t, 2H), 3.17–3.24 (m, 4H), 3.32–3.36 (m, 2H), 3.71–3.78 (m, 2H), 3.84–3.87 (t, 2H), 7.36–7.41 (m, 2H), 7.54 (t, 1H), 7.91 (d, 1H).

b) 3-[2-[2-[2-Nitrophenyl]ethoxy]ethylsulphonyl] propanoic acid

Lithium metal (0.59 g) was allowed to dissolve in methanol (200 ml). Water (100 ml) was added and then the compound from step a) (6.05 g) in methanol (50 ml) was added dropwise to the cooled (ice/salt) solution. The reaction was allowed to warm to room temperature and stirring was continued overnight. The solvent was removed under reduced pressure and the residual material diluted with water. The basic aqueous solution was washed with ethyl acetate (which was discarded), acidified to pH 2 (concentrated hydrochloric acid) and extracted with ethyl acetate. These extracts were combined, washed with water and brine, dried ($MgSO_4$) and the solvents evaporated under reduced pressure to yield the crude product which was further purified by flash chromatography over silica using 9:1 dichloromethane:methanol as eluant to yield the subtitled compound.

Mass Spectrum: TSP 349 [$(M+NH_4)^+$].

c) N-[2-[4-Hydroxy-2-oxo-3H-1,3-benzothiazol-7-yl]ethyl]-3-[2-[2-nitrophenyl]-ethoxyethylsulphonyl] propanamide The subtitled compound was prepared using the general method outlined in Example 20c) using 7-[2-aminoethyl]-4-hydroxy-1,3-benzothiazol-2(3H)-one hydrobromide and the product from step b) to yield, after purification by chromatography over silica using 6% ethanol in chloroform as eluant the subtitled compound.

Mass Spectrum: FAB (+ve) 524 [$(M+H)^+$];

$^1$H NMR ($D_6$-DMSO) δ:2.5 (m, 4H), 2.60 (t, 2H), 3.09 (t, 2H), 3.24 (m, 4H), 3.68 (t, 2H), 3.74 (t, 2H), 6.70 (d, 1H), 6.80 (d, 1H), 7.47 (t, 1H), 7.55 (d, 1H), 7.62 (t, 1H), 7.91 (d, 1H), 8.14 (t, 1H), 9.91 (s, 1H), 11.62 (s, 1H).

d) N-[2-[4-Hydroxy-2-oxo-3H-1,3-benzothiazol-7-yl]ethyl]-3-[2-[2-[2-aminophenyl]-ethoxy] ethylsulphonyl]propanamide Hydrazine hydrate (10 ml) was added dropwise to a stirred suspension of freshly washed Raney Nickel, the compound from step c) (2.21 g) and ethanol (50 ml). After the reaction was complete the Raney Nickel was filtered off (CAUTION FIRE HAZARD!)) and the ethanol evaporated under reduced pressure. The residue was partitioned between water and dichloromethane and the aqueous layer further extracted with portions of dichloromethane. The combined extracts were washed with water and brine, dried ($MgSO_4$) and evaporated under reduced pressure to yield the crude product. The material was used without further purification.

Mass Spectrum: FAB (+ve) 494 [$(M+H)^+$];

$^1$H NMR ($D_6$-DMSO) δ:2.4–2.8 (t, 8H), 3.2–3.4 (m, 6H), 3.58 (t, 2H), 3.76 (t, 2H), 6.46 (t, 1H), 6.59 (d, 1H), 6.70 (d, 1H), 6.80 (d, 1H), 6.86–6.93 (m, 2H), 8.16 (t, 1H), 9.93 (brs, 1H), 11.63 (s, 1H).

e) 4-Hydroxy-7-[2-[3-[2-[2-[2-aminophenyl]ethoxy] ethylsulphonyl]propylamino]-1,3-ethyl]-1,3-benzothiazol-2(3H)-one dihydrochloride The title compound was prepared using the general method outlined in Example 20d) using the product from step d). The crude reaction product was purified by preparative reverse phase HPLC using acetonitrile 0.1% aqueous trifluoroacetic acid as eluant.

mp 65° (softens);

Mass Spectrum: FAB (+ve) 480 [$(M+H)^+$];

$^1$H NMR ($D_6$-DMSO) δ:2.00–2.08 (m, 2H), 2.8–3.3 (m, 10H) 3.39–3.45 (m, 2H), 3.71 (t, 2H), 3.81 (t, 2H), 4.5 (brs, 3H), 6.77 (d, 1H), 6.89 (d, 1H)$_2$ 7.28–7.36 (m, 4H), 9.04 (brs, 2H), 10.15 (s, 1H), 11.6 (s, 1H).

EXAMPLE 33

4-Hydroxy-7-[2-[3-[2-[2-[4-nitrophenyl)ethoxy] ethylsulphonyl]propylamino[-ethyl]-1,3-benzothiazol-2(3H)-one hydrochloride a) N-[2-[4-Hydroxy-2-oxo-3H-1,3-benzothiazol-7-yl]ethyl]-3-[2-[2-[4-nitrophenyl]-ethoxy] ethylsulphonyl]propanamide Following the general method outlined in Example 20c) using 7-[2-aminoethyl]-4-hydroxy-1,3-benzothiazol-2(3H)-one hydrobromide and 3-[2-[2-[4-nitrophenyl]-ethoxy] ethylsulphonyl]propanoic acid [Example 13a)]gave the subtitled compound after purification by chromatography over silica using 8% ethanol in dichloromethane as eluant.

Mass Spectrum: FAB (+ve) 524 [$(M+H)^+$];

$^1$H NMR ($D_6$-DMSO) δ:2.45 (t, 2H), 2.60 (t, 2H), 2.97 (t, 2H), 3.2–3.4 (m, 6H), 3.69–3.77 (m, 4H), 6.70 (d, 1H), 6.80 (d, 1H), 7.53 (d, 2H), 8.12 (d, 3H), 9.91 (brs, 1H), 11.6 (brs, 1H).

b) 4-Hydroxy-7-[2-[3-[2-[2-[4-nitrophenyl]ethoxy] ethylsulphonyl]propylamino]-ethyl]-1,3-benzothiazol-2(3H)-one hydrochloride The title compound was prepared using the general method outlined in Example 20d). The crude reaction product was purified by preparative reverse phase HPLC using acetonitrile in 0.1% aqueous trifluoroacetic acid as eluant.

mp 75°–78°;

Mass Spectrum: FAB (+ve) 510 [$(M+H)^+$];

$^1$H NMR ($D_6$-DMSO) δ:2.01 (quin, 2H), 2.83 (t, 2H), 2.98 (t, 4H), 3.12 (t, 4H), 3.39 (t, 2H), 3.70–3.79 (m, 4H), 6.76 (d, 1H), 6.88 (d, 1H), 7.55 (d, 2H), 8.16 (d, 2H), 8.83 (brs, 2H), 10.13 (s, 1H), 11.76 (s, 1H).

EXAMPLE 34

7-[2-[2-[3-[2-[4-Fluorophenyl]ethoxy]
propylsulphonyl]ethylamino]ethyl]-4-hydroxy-1,3-
benzothiazol-2(3H)-one hydrochloride a) 2-[4-Fluorophenyl]ethyl allyl ether 2-[4-Fluorophenyl]ethanol (7.0 g) was added slowly to a stirred suspension of sodium hydride (1.25 g, 60% as dispersion in oil prewashed with petroleum ether bp 60°–80°) in DMF (50 ml). The mixture was stirred for 30 min at room temperature. Allyl bromide (6.0 g) was then added slowly and the whole allowed to stir overnight. The reaction was partitioned between water and ether. The aqueous layer was further extracted with ether and the combined ethereal extracts were washed with water and dried (MgSO$_4$). The ether was removed under reduced pressure to yield the crude subtitled compound as a colourless oil (8.7 g, 96%).

Mass Spectrum: EI 180 (M$^+$);

$^1$H NMR (CDCl$_3$) δ:2.9 (t, 2H), 3.6 (t, 2H), 4.0 (t, 2H), 5.2 (m, 2H), 5.9 (m, 1H), 6.95 (m, 2H), 7.2 (m, 2H).

This reaction was successfully repeated on a ×5 scale.

b) 2-[3-[2-[4-Fluorophenyl]ethoxy]propylthio]acetic acid

The compound from step a) (15 g) and thioglycolic acid (6.8 ml) were stirred together at room temperature in a conical flask exposed to the atmosphere for 2 hours at which point more thioglycolic acid (3.4 ml) was added. After a further ½ hour stirring the reaction was complete. The crude material was chromatographed over silica using 99:1 dichloromethane:acetic acid as eluant to yield the subtitled compound as a colourless oil (19.69 g, 87%).

Mass Spectrum: FAB (+ve) 273 [(M+H)$^+$];

$^1$H NMR (CDCl$_3$) δ:1.87 (m, 2H), 2.71 (t, 2H), 2.85 (t, 2H), 3.31 (d, 2H), 3.51 (t, 2H), 3.65 (t, 2H), 6.98 (m, 2H), 7.18 (m, 2H).

c) 2-[3-[2-[4-Fluorophenylethoxy]propylsulphonyl] acetic acid

A solution of potassium hydrogen carbonate (150 g) in water (500 ml) was added over a 20 min period to a stirred mixture of the acid from step b) (39.5 g) in water (50 ml). An aqueous solution of OXONE™ (278 g in 400 ml) was added in portions and the reaction left to stir overnight. Water (1 L) was then added and the whole extracted with ether (to remove non acidic material). The aqueous layer was then acidified with 20% aqueous sulphuric acid and extracted with ether (×3). The ethereal layers were combined, washed with water and brine, dried (MgSO$_4$) and concentrated under reduced pressure to yield a pale yellow oil (41.7 g). A white solid precipitated out from the oil on standing. The solid was removed by filtration and washed with small amounts of 1:1 ether:pentane to yield the subtitled compound.

mp 47°–48°;

Mass Spectrum: FAB (+ve) 305 [(M+H)$^+$];

$^1$H NMR (CDCl$_3$) δ:2.12 (m, 2H), 2.84 (t, 2H), 3.32 (m, 2H), 3.58 (t, 2H), 3.65 (t, 2H), 4.00 (s, 2H), 6.98 (m, 2H), 7.16 (m, 2H), 8.80 (brs, 1H).

d) N-[2-[4-Hydroxy-2-oxo-3H-1,3-benzothiazol-7-yl]ethyl]-2-[3-[2-[4-fluorophenyl]-ethoxy]propylsulphonyl]acetamide Carbonyl diimidazole (1.94 g) was added to a stirred solution of the acid from step c) (3.64 g) in DMF (15 ml). Stirring was continued for 40 min at room is temperature. To this solution was added 7-[2-aminoethyl]-4-hydroxy-1,3-benzothiazol-2(3H)-one hydrobromide (3.48 g) followed by triethylamine (1.7 ml). The whole was left overnight. The reaction mixture was then added slowly to a rapidly stirred mixture of 10% aqueous hydrochloric acid and ether (100 ml each). A pale yellow solid gradually settled out and was filtered off, washed with pentane and dried in vacuo. This provided the subtitled compound as a buff coloured material which was used in the next step without further purification.

Mass Spectrum: FAB (+ve) 497 [(M+H)$^+$];

$^1$H NMR (D$_6$-DMSO) δ:1.91 (m, 2H), 2.61 (t, 2H), 2.80 (t, 2H), 3.30 (m, 4H), 3.48 (t, 2H), 3.56 (t, 2H), 4.03 (s, 2H), 6.70 (d, 1H), 6.82 (d, 1H), 7.10 (t, 2H), 7.28 (m, 2H), 8.46 (t, 1H), 9.95 (s, 1H), 11.66 (s, 1H).

e) 7-[2-[2-[3-[2-[4-Fluorophenyl]ethoxy]
propylsulphonyl]ethylamino]ethyl]-4-hydroxy-1,3-
benzothiazol-2(3H)-one hydrochloride The title compound was prepared using the general method outlined in Example 20d) using the compound from step d). The crude reaction product was purified by preparative reverse phase HPLC using 35% THF in 0.1% aqueous trifluoroacetic acid as eluant.

mp 240°–245°;

Mass Spectrum: FAB (+ve) 483 [(M+H)$^+$];

$^1$H NMR (D$_6$-DMSO) δ:1.91 (m, 2H), 2.80 (t, 2H), 2.85 (t, 2H), 3.14 –3.21 (m, 4H), 3.24 (2H+D$_2$O), 3.49 (t, 2H), 3.54 (q, 4H), 6.76 (d, 1H), 6.87 (d, 1H), 7.10 (t, 2H), 7.27 (t, 2H), 9.14 (s, 2H), 10.15 (s, 1H), 11.78 (s, 1H);

Analysis: Found; C,50.58; H,5.62; N,5.61; S,12.26%.

C$_{22}$H$_{27}$N$_2$FO$_5$S$_2$.HCl requires: C,50.91; H,5.44; N,5.40; S,12.36%.

EXAMPLE 35

4-Hydroxy-7-[2-[2-[3-[2-[2-thienyl]ethoxy]
propylthiolethylamino]ethyl-1,3-benzothiazol-2(3H)
-one hydrochloride The title compound was prepared according to the procedure outlined in Example 34 employing 2-thienylethanol, except that for the oxidation of Example 15c) the general procedure described in Example 1b) was employed.

mp 220°–221°;

Mass Spectrum: FAB (+ve) 471 [(M+H)$^+$];

$^1$H NMR (D$_6$-DMSO) δ:1.90–1.98 (m, 2H), 2.53 (m, 2H), 2.85 (t, 2H), 3.03 (t, 2H), 3.16 (m, 2H), 3.25 (m, 2H), 3.37 (m, 2H), 3.53 (m, 2H), 3.60 (t, 2H), 6.76 (d, 1H), 6.88 (m, 2H), 6.94 (m, 1H), 7.33 (dd, 1H), 9.09 (brs, 2H), 10.14 (s, 1H), 11.78 (brs, 1H);

Analysis: Found; C,46.67; H,5.51; N,5.68; S,18.42%.

C$_{20}$H$_{26}$N$_2$O$_5$S$_3$.HCl requires: C,47.37; H,5.37; N,5.52; S,18.97%.

EXAMPLE 36

4-Hydroxy-7-[2-[3-[2-[2-[2-pyridyl]ethoxy]
ethylthiolpropylamino]ethyl]-1,3-benzothiazol-2
(3H)-one dihydrochloride a) 2-[2-[2-Bromoethylthiolethyl]-1,3-dioxolane To a stirred cooled (<0°) solution of 2-[2-[1,3-dioxolan-2-yl]ethylthio]ethanol (13.6 g, prepared by the condensation between mercaptoethanol and 2-[2-bromoethyl]-1,3- dioxolane employing sodium hydride) in dry acetonitrile (150 ml) was added triphenylphosphine (20 g) and carbon tetrabromide (38 g). The solution was stirred for 4 hours. The solvent was removed under reduced pressure and the residue pre-absorbed onto silica. The material was flash chromatographed over silica using 10% ethylacetate/petroleum ether as eluant to afford the subtitled compound as a clear oil (4.45 g). The material was used in the next step without further purification.

b) 2-[2-[2-[2-[2-Pyridyl]ethoxy]ethylthio]ethyl]-1,3-dioxolane

The material from step a) (6.12 g), tetra-n-butylammonium hydrogen sulphate (1 g) and 2-pyridylethanol (2.85 ml) were stirred together with dichloromethane and 20% aqueous sodium hydroxide each (20 ml) until gas chromatographic analysis indicated that the reaction had stopped. The organic layer was separated, washed with water and dried (MgSO$_4$). Removal of the solvents under reduced pressure yielded an oil. This material was further purified by flash chromatography over silica using 4:1 ethyl acetate:petroleum ether (bp 60°–80°) as eluant to yield the subtitled compound as a yellow oil (0.770 g).

$^1$H NMR (CDCl$_3$) δ:1.92 (m, 2H), 2.65 (m, 4H), 3.07 (t, 2H), 3.62 (t, 2H), 3.85 (m, 4H), 3.95 (m, 2H), 4.94 (t, 1H), 7.13 (m, 1H), 7.22 (d, 1H), 7.60 (td, 1H), 8.53 (d, 1H).

c) 3-[2-[2-[2-Pyridyl]ethoxy ethylthio]propanal

The material from step b) (0.850 g) was dissolved in 80% formic acid (10 ml) and left to stand at room temperature for 22 hours. The mixture was partitioned between ether and water. The layers were separated and the aqueous layer extracted with ether. The ethereal extracts were combined, washed with brine, dried (MgSO$_4$) and evaporated is under reduced pressure to yield the subtitled compound as an oil (0.70 g).

$^1$H NMR (CDCl$_3$) δ:2.69 (m, 4H), 2.87 (t, 2H), 3.06 (t, 2H), 3.64 (t, 2H), 3.85 (t, 2H), 7.13 (td, 1H), 7.21 (d, 1H), 7.60 (td, 1H), 8.53 (d, 1H), 9.74 (s, 1H).

d) 4-Hydroxy-7-[2-[3-[2-[2-[2-pyridyl]ethoxy] ethylthio]propylamino]ethyl]-1,3-benzothiazol-2 (3H)-one dihydrochloride The material from step c) (0.700 g) was dissolved in methanol (20 ml). To this solution was added 7-[2-aminoethyl]-4-hydroxy-1,3-benzothiazol-2(3H)-one hydrobromide (0.655 g), sodium cyanoborohydride (0.100 g) and aqueous 6% acetic acid (to adjust the pH to 6). The solution was stirred at room temperature overnight and then made basic with concentrated ammonium hydroxide solution. The solvent was removed under reduced pressure and the residual material purified by column chromatography over silica using methanol in dichloromethane as eluant. The resultant combined fractions were further purified by reverse phase HPLC using acetonitrile in 0.1% aqueous trifluoroacetic acid as eluant which after preparation of the hydrochloride salt yielded a pure sample of the title compound.

mp 50°–60° (softens);

Mass Spectrum: FAB (+ve) 434 [(M+H)$^+$];

$^1$H NMR (D$_6$-DMSO) δ:1.86 (m, 2H), 2.55 (t, 2H), 2.62 (t, 2H), 2.88 (m, 2H), 2.91 (m, 2H), 2.95 (m, 2H), 3.28 (t, 2H), 3.58 (t, 2H), 3.85 (t, 2H), 6.78 (d, 1H), 6.88 (d, 1H), 7.85 (t, 1H), 7.96 (d, 1H), 8.45 (t, 1H), 8.78 (d, 1H), 9.17 (brs, 2H), 10.17 (brs, 1H), 11.78 (brs, 1H);

Analysis: Found; C,47.69; H,6.08; N,7.79; S,10.88; Cl,12.84%.

C$_{21}$H$_{27}$O$_3$S$_2$.2HCl.1.5H$_2$O requires: C,47.27; H,6.05; N,7.88; S,12.02; Cl,13.29%.

What is claimed is:

1. A method for the preparation of a compound of formula I, or a pharmaceutically acceptable derivative thereof

in which

Ar represents a group:

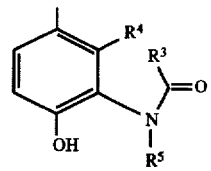

X represents a C$_{1-12}$ alkylene chain interrupted or terminated by one or more groups selected from the group consisting of —SO$_n$—, —O—, —C(Z)—, CR$^6$R$^7$, phenylmethyne, —NR$^8$—, —CONH—, —NHCO— and —NHCONH—;

Y represents an optionally substituted aryl or cycloalkyl group:

Z represents O or S:

R$^1$, R$^2$, R$^5$ and R$^9$ each independently represent hydrogen or C$_{1-6}$ alkyl);

R$^3$ and R$^4$ together represent —S—, —NR$^9$— or —CH$_2$—;

R$^6$ and R$^7$ each independently represent hydrogen, C$_{1-6}$ alkyl, fluoro, cyano, or CF$_3$, provided that at least one of R$^6$ and R$^7$ is other than hydrogen;

R$^8$ represents hydrogen or C$_{1-6}$ alkyl or when X is interrupted or terminated by more than one —NR$^8$— group may together with another R$^8$ group form the chain —CH$_2$—CH$_2$—; and n represents 0, 1 or 2;

a) alkylation of a compound of formula II, or a derivative thereof,

in which Ar is as defined above, with an alkylating agent of formula III,

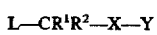

in which R$^1$, R$^2$, X and Y are as defined above and L represents a leaving group, b) alkylation of a compound of formula II with a compound of formula IV,

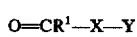

in which R$^1$, X and Y are as defined above, in the presence of a reducing agent, c) selective reduction of a compound of formula V,

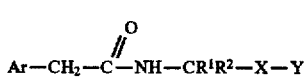

in which Ar, X, Y, R$^1$ and R$^2$ are as defined above, or for the production of compounds of formula I in which R$^1$ and R$^2$ represent hydrogen, selective reduction of a compound of formula Va,

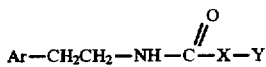

in which Ar, X and Y are as defined above, d) removal of a protecting group from a corresponding protected compound of formula I in which one or more of the functional groups is protected, and where desired or necessary converting a compound of formula I to a pharmaceutically acceptable derivative thereof, or vice versa.

2. Compounds of formula Va,

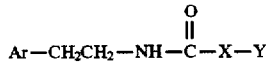

in which Ar, X and Y are as defined in claim 1.

3. A method of treatment or prophylaxis of reversible obstructive airways disease in a patient in need of such treatment, which method comprises administering to said patient a therapeutically effective quantity of a compound of formula I:

in which

Ar represents a group:

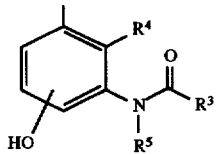

X represents a $C_{1-12}$ alkylene chain interrupted or terminated by one or more groups selected from —$SO_n$—, —O—, —C(Z)—, $CR^6R^7$, phenylmethyne, —NR—, —CONH—, —NHCO— and —NHCONH—, Y represents a 5- or 6-membered carbocyclic or heterocyclic group optionally substituted by one or more groups selected —OH, halogen, alkyl $C_{1-6}$, αO, —$NH_2$ or $NO_2$, Z represents O or S, $R^1$, $R^2$, $R^5$ and $R^9$ each independently represent hydrogen or alkyl $C_{1-6}$, and $R^3$ and $R^4$ represent hydrogen, or $R^3$ and $R^4$ together form a group —S—, —$NR^9$— or —$CH_2$—, $R^6$ and $R^7$ independently represent hydrogen, alkyl $C_{1-6}$; fluoro, cyano, or $CF_3$, provided that at least one of $R^6$ and $R^7$ is other than hydrogen, $R^8$ represents hydrogen or alkyl $C_{1-6}$, or when X is interrupted or terminated by more than one —$NR^8$— group may together with another $R^8$ group form the chain —$CH_2$—$CH_2$—, and n represents 0, 1 or 2.

4. A method according to claim 3, wherein $R^3$ and $R^4$ together represent the group —S—.

5. A method according to claim 3, wherein $R^5$ represents hydrogen.

6. A method according to claim 3, wherein the —OH is positioned ortho to the —$NR^2$—C(O)$R^3$ group.

7. A method according to claim 3, wherein Y represents phenyl optionally substituted by one or more groups selected from —OH, halogen, alkyl $C_{1-6}$, alkoxy $C_{1-6}$, =O, —$NH_2$ or $NO_2$.

8. A method according to claim 7, wherein Y represents unsubstituted phenyl.

9. A method according to claim 3, wherein Ar represents the group:

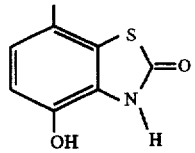

and —$CR^1R^2$—X—Y represents —$(CH_2)_p$—W—$(CH_2)_q$—Q—$(CH_2)_r$—R, wherein W and Q independently represent —$S(O)_n$— or —O—, n represents 0, 1 or 2, p, q and r independently represent 2 or 3, R represents phenyl optionally substituted by halogen, —$OR^1$, $NO_2$ or $NR^2R^3$; or a 5, or 6-membered N, O, or S-containing heterocycle, and $R^1$, $R^2$ and $R^3$ independently represent hydrogen or alkyl $C_{1-6}$.

10. A method according to claim 9, wherein r represents 2.

11. A method according to claim 9, wherein p+q represents 5.

12. A method according to claim 9, wherein Q represents O.

13. A method according to claim 3, wherein W represents —S— or —$SO_2$—.

14. A method according to claim 3, wherein the compound of formula I is:

4-Hydroxy-7-[2-[2-[3-[2-phenylethoxy]propylsulphonyl]ethylamino]ethyl]-1,3-benzothiazol-2(3H)-one, or a pharmaceutically acceptable derivative thereof.

15. A method according to claim 3, wherein the compound of formula I is:

7-[2-[6-[2-(2,3-Dihydro-1H-indenyloxy)hexyl]aminoethyl]-4-hydroxy-1,3-benzothiazol-2(3H)-one, 4-Hydroxy-7-[2-[6-(2-phenylethoxy)hexyl]aminoethyl]-1,3-benzothiazol-2(3H)-one, 4-Hydroxy-7-[2-[5-(3-phenylpropoxy)pentyl]aminoethyl]-1,3-benzothiazo-2(3H)-one, 4-Hydroxy-7-[2-[7-(2-phenylethoxy)heptyl]aminoethyl]-1,3-benzothiazol-2(3H)-one, 4-Hydroxy-7-[2-[4-(2-phenylethoxy)butyl]aminoethyl]-1,3-benzothiazol-2(3H)-one, 4-Hydroxy-7-[2-[5-(2-phenylethoxy)pentyl]aminoethyl]-1,3-benzothiazol-2(3H)-one, 4-Hydroxy-7-[2-[6-(phenylmethoxy)hexyl]aminoethyl]-1,3-benzothiazol-2(3H)-one, 4-Hydroxy-7-[2-[4(4-phenylbutoxy)butyl]aminoethyl]-1,3-benzothiazol-2(3H)-one, 4-Hydroxy-7-[7-[2-(6-phenoxyhexyl)aminoethyl]-1,3-benzothiazol-2(3H)-one, 4-Hydroxy-7-[2-[6-(3-phenylpropoxy)hexyl]aminoethyl]-1,3-benzothiazol-2(3H)-one, 4-Hydroxy-7-[2-[2,2-dimethyl-6-(2-phenylethoxy)hexyl]aminoethyl]-1,3-benzothiazol-2(3 H)-one, 4-Hydroxy-7-[2-[6-(2-phenylethylsulphonyl)hexyl]aminoethyl]-1,3-benzothiazol-2(3H)-one, N-[6-[2-(4-Hydroxy-2-oxo-3H-1,3-benzothiazol-7-yl)ethylamino]hexyl]-N'-phenyl urea, 4-Hydroxy-7-[2-[6-[2-(4-nitrophenyl)ethoxy]hexyl]aminoethyl]-1,3-benzothiazol-2(3H)-one, 4-Hydroxy-7-[2-[6-[2-(4-hydroxyphenyl)ethoxy]-2,2-dimethylhexyl]aminoethyl]-1,3-benzothiazol-2(3H)-one, 7-Hydroxy-4-[2-[6-[2-(1-naphthyl)ethoxy]hexyl]aminoethyl]-1,3-benzothiazol-2(3H)-one, 7-[2-[6-(2-Cyclohexylethoxy)hexyl]aminoethyl]-4-hydroxy-1,3-benzothiazol-2(3H)-one, 7-[2-[6-[2-(4-Bromophenyl)ethoxy]hexyl]aminoethyl]-4-hydroxy-1,3-benzothiazol-2(3H)-one, 4-Hydroxy-7-[2-[6-[2-(2-thienyl)ethoxy]hexyl]aminoethyl]-1,3-benzothiazol-2(3H)-one, (R,S)-4-Hydroxy-7-[2-[2-methyl-6-(2-phenylethoxy)hexyl]aminoethyl]-1,3-benzothiazol-2(3H)-one, 1,3-Dihydro-4-hydroxy-7-[2-[6-(2-phenylethoxy)hexyl]aminoethyl]-2H-benzimidazol-2-one, 4-Hydroxy-7-[2-[6-[2(4-hydroxyphenyl)ethoxy]hexyl]aminoethyl]-1,3-benzothiazol-2(3H)-one, 2,3-Dihydro-7-hydroxy-4-[2-[6(phenylethoxy)hexyl]aminoethyl]-indol-2-one, 4-Hydroxy-7-[2-[3-[2-(2-phenylethyl)aminoethyl]sulphonylpropyl]aminoethyl]-1,3-benzothiazol-2(3H)-one, (R,S)-4-Hydroxy-7-[2-[7-(2-phenylethoxy)-hept-2-yl]aminoethyl]-1,3-benzothiazol-2(3H)-one, 6-[2-[(4-Hydroxy-2-oxo-3H-1,3-benzothiazol-7-yl)ethyl]amino]-N-(2-phenylethyl)-hexanamide, 4-Hydroxy-7-[2-[6-(2-phenylethylthio)hexyl]aminoethyl]-1,3-benzothiazol-2(3H)-one, N-(2-Hydroxy-5-[2-N'-[6-(2-phenylethoxy)hexyl]aminoethyl]phenyl]formamide, 7-[2-[6-[2-(4-Aminophenyl)ethoxy]hexyl]aminoethyl]-4-hydroxy-1,3-benzothiazol-2(3H)-one, 4-Hydro-7-[2-[6-[2-(2-pyridyl)ethoxy]hexyl]aminoethyl]-1,3-benzothiazol-2(3H)-one, 7,7'-[1,6-Hexanediylbis(imino-2,1-ethanediyl)]bis[4-hydroxy-1,3-benzothiazol-2(3H)-one], 7-[2-[1,1-Dimethyl-6-(2-phenylethoxy)hexyl]aminoethyl]-4-hydroxy-1,3-benzothiazol-2(3H)-one, 4-Hydroxy-7-[2-[6-[2,2-difluoro-2-phenethylamino]hexylamino]ethyl]-1,3-benzothiazol-2(3H)-one, 7-[2-[2,2-Difluoro-6-[2-phenylethoxy]hexylamino]ethyl]-4-hydroxy-1,3-benzothiazol-2(3H)-one, 7-[2-[3,3-Difluoro-6-[2-phenylethoxy]hexylamino]ethyl]-4-hydroxy-1,3-benzothiazol-2(3H)-one, 2-[3-[2-[4-Hydroxy-2-oxo-3H-1,3-benzothiazol-7-yl]ethylamino]propyl]-2-[2-phenylethoxy]ethylpropanedinitrile, N-[2-[2-[4-Hydroxy-2-oxo-3H-1,3-benzothiazole-7-yl]ethylamino]ethyl]-N-methyl-3-[2-phenylethoxy]propanamide, 4-Hydroxy-7-[2-[3-[2-[2-phenylethoxy]ethylsulphonyl]propylamino]ethyl]-1,3-benzothiazol-2(3H)-one, 4-Hydroxy-7-[2-[2-[3-[2-phenylethoxy]propoxy]ethylamino]ethyl]-1,3-benzothiazol-2(3H)-one, 4-Hydroxy-7-[2-[3-[2-[2-phenylethoxy]ethoxy]propylamino]ethyl]-1,3-benzothiazol-2(3H)-one, 4-Hydroxy-7-[2-[2-[2-[2-phenylethoxy]ethoxy]ethylamino]ethyl]-1,3-benzothiazol-2(3H)-one, 4-Hydroxy-7-[2-[2-[3-[2-phenylethoxy]propylthio]ethylamino]ethyl]-1,3-benzothiazol-2(3H)-one, 4-Hydroxy-7-[2-[3-[2-[2-phenylethoxy]ethylthio]propylamino]ethyl]-1,3-benzothiazol-2(3H)-one, 3-Hydroxy-7-[2-[3-[2-[2-aminophenyl]ethoxy]ethylsulphonyl]propylamino]ethyl]-1,3-benzothiazol-2(3H)-one, 4-Hydroxy-7-[2-[3-[2-[4-nitrophenyl]ethoxy]ethylsulphonyl]propylamino]-ethyl]-1,3-benzothiazol-2(3H)-one, 7-[2-[2-[3-[2-[4-Fluorophenyl]ethoxy]propylsulphonyl]ethylamino]ethyl]-4-hydroxy-1,3-benzothiazol-2(3H)-one, 4-Hydroxy-7-[2-[2-[3-[2-[2-thienyl]ethoxy]propylthio]ethylamino]ethyl]-1,3-benzothiazol-2(3H)one, or 4-Hydroxy-7-[2-[3-[2-[2-pyridyl]ethoxy]ethylthio]propylamino]ethyl]-1,3-benzothiazol-2(3H)-one, or a pharmaceutically acceptable derivative of any one thereof.

16. A pharmaceutical composition comprising a compound of formula I, as defined in claim 3, or a pharmaceutically acceptable derivative thereof, in association with a pharmaceutically acceptable diluent or carrier.

17. A pharmaceutical composition comprising a compound of formula I, as defined in claim 9, or a pharmaceutically acceptable derivative thereof, in association with a pharmaceutically acceptable diluent or carrier.

* * * * *